(12) United States Patent
Chand et al.

(10) Patent No.: US 10,513,497 B2
(45) Date of Patent: Dec. 24, 2019

(54) PROCESS FOR PREPARING AG-10, ITS INTERMEDIATES, AND SALTS THEREOF

(71) Applicant: EIDOS THERAPEUTICS, INC., San Francisco, CA (US)

(72) Inventors: Pooran Chand, San Francisco, CA (US); Yogesh Kumar Gupta, San Francisco, CA (US); Rakesh Kumar Kumawat, San Francisco, CA (US); Mamoun Alhamadsheh, San Francisco, CA (US); Robert Zamboni, San Francisco, CA (US)

(73) Assignee: EIDOS THERAPEUTICS, INC., San Francisco, CA (US)

(*) Notice: Subject to any disclaimer, the term of this patent is extended or adjusted under 35 U.S.C. 154(b) by 0 days.

(21) Appl. No.: 15/932,327

(22) Filed: Feb. 16, 2018

(65) Prior Publication Data
US 2018/0237396 A1    Aug. 23, 2018

Related U.S. Application Data

(60) Provisional application No. 62/460,576, filed on Feb. 17, 2017.

(51) Int. Cl.
*C07D 231/12* (2006.01)
*C07C 309/04* (2006.01)
*C07C 309/30* (2006.01)

(52) U.S. Cl.
CPC .......... *C07D 231/12* (2013.01); *C07C 309/04* (2013.01); *C07C 309/30* (2013.01); *C07B 2200/13* (2013.01)

(58) Field of Classification Search
None
See application file for complete search history.

(56) References Cited

U.S. PATENT DOCUMENTS

| | | |
|---|---|---|
| RE28,819 E | 5/1976 | Thompson |
| 4,232,161 A | 11/1980 | Diana et al. |
| 4,234,725 A | 11/1980 | Diana et al. |
| 4,255,329 A | 3/1981 | Ullman |
| 4,261,928 A | 4/1981 | Diana et al. |
| 4,328,245 A | 5/1982 | Yu et al. |
| 4,358,603 A | 11/1982 | Yu |
| 4,409,239 A | 10/1983 | Yu |
| 4,410,545 A | 10/1983 | Yu et al. |
| 4,522,811 A | 6/1985 | Eppstein et al. |
| 4,657,914 A | 4/1987 | Bernardi et al. |
| 4,668,640 A | 5/1987 | Wang et al. |
| 5,315,015 A | 5/1994 | Hui et al. |
| 5,521,202 A | 5/1996 | Yano et al. |
| 5,709,874 A | 1/1998 | Hanson et al. |
| 5,759,542 A | 6/1998 | Gurewich |
| 5,840,674 A | 11/1998 | Yatvin et al. |
| 5,860,957 A | 1/1999 | Jacobsen et al. |
| 5,900,252 A | 5/1999 | Calanchi et al. |
| 5,948,433 A | 9/1999 | Burton et al. |

(Continued)

FOREIGN PATENT DOCUMENTS

| | | |
|---|---|---|
| DE | 2834322 A1 | 2/1979 |
| WO | 1995012815 | 5/1995 |

(Continued)

OTHER PUBLICATIONS

National Center for Biotechnology Information. PubChem Compound Database; CID=71464713, https://pubchem.ncbi.nlm.nih.gov/compound/71464713 (accessed Jan. 17, 2019).*
Adamski-Werner, et al., Diflunisal Analogues Stabilize the Native State of Transthyretin. Potent Inhibition of Amyloidogenesis, J Med Chem , 2004 , pp. 355-374, vol. 47, No. 2.
Aldred , The cerebral expression of plasma protein genes in different species, Comp Biochem Physiol B Biochem Mol Biol., 1995, pp. 1-15, vol. 1, No. 1.
Alhamadsheh, et al., Potent Kinetic Stabilizers that Prevent Transthyretin-Mediated Cardiomyocyte Proteotoxicity, Sci. Transl. Med. , 2011, pp. 1-9, vol. 3, No. 97.

(Continued)

*Primary Examiner* — Alicia L Otton
(74) *Attorney, Agent, or Firm* — Mintz, Levin, Cohn, Ferris, Glovsky and Popeo, P.C.

(57) ABSTRACT

Provided herein are improved processes for the preparation of a compound of Formula IX (AG-10). Also provided herein are pharmaceutically acceptable salts of Formula I and Formula Ib

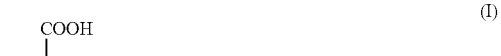
(I)

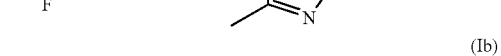

(Ib)

as well as crystalline types of Formula IX (AG-10). The processes described herein provide improved yields and efficiency, while the pharmaceutically acceptable salts and crystalline forms provide unexpected pharmacokinetic properties. Other features and aspects of the present disclosure will be apparent to a person of skill in the art upon reading the remainder of the specification.

10 Claims, 53 Drawing Sheets

(56) References Cited

U.S. PATENT DOCUMENTS

| | | | |
|---|---|---|---|
| 5,972,366 | A | 10/1999 | Haynes et al. |
| 5,983,134 | A | 11/1999 | Ostrow |
| 5,985,307 | A | 11/1999 | Hanson et al. |
| 5,985,317 | A | 11/1999 | Venkateshwaran et al. |
| 6,004,534 | A | 12/1999 | Langer et al. |
| 6,010,715 | A | 1/2000 | Wick et al. |
| 6,024,975 | A | 2/2000 | D et al. |
| 6,039,975 | A | 3/2000 | Shah et al. |
| 6,048,736 | A | 4/2000 | Kosak |
| 6,060,082 | A | 5/2000 | Chen et al. |
| 6,071,495 | A | 6/2000 | Unger et al. |
| 6,120,751 | A | 9/2000 | Unger |
| 6,131,570 | A | 10/2000 | Schuster et al. |
| 6,139,865 | A | 10/2000 | Friend et al. |
| 6,167,301 | A | 12/2000 | Flower et al. |
| 6,253,872 | B1 | 7/2001 | Neumann |
| 6,256,533 | B1 | 7/2001 | Yuzhakov et al. |
| 6,261,595 | B1 | 7/2001 | Stanley et al. |
| 6,267,983 | B1 | 7/2001 | Fujii et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 7,763,747 | B2 | 7/2010 | Snow et al. |
| 8,143,424 | B2 | 3/2012 | Chhipa et al. |
| 8,378,118 | B2 | 2/2013 | Chhipa et al. |
| 8,877,795 | B2 | 11/2014 | Graef et al. |
| 9,169,214 | B2 | 10/2015 | Graef et al. |
| 9,308,209 | B2 | 4/2016 | Graef et al. |
| 10,039,726 | B2 | 8/2018 | Graef et al. |
| 2006/0160796 | A1 | 7/2006 | Pfahl et al. |
| 2006/0183792 | A1 | 8/2006 | Fobare et al. |
| 2008/0319077 | A1 | 12/2008 | Suzuki et al. |
| 2009/0247547 | A1 | 10/2009 | Shultz et al. |
| 2010/0249094 | A1 | 9/2010 | Yeung et al. |
| 2014/0179751 | A1* | 6/2014 | Graef .................. C07D 231/12 514/406 |
| 2017/0029390 | A1 | 2/2017 | Butler et al. |
| 2018/0237396 | A1 | 8/2018 | Chand et al. |

FOREIGN PATENT DOCUMENTS

| | | | |
|---|---|---|---|
| WO | 2004096808 | A1 | 11/2004 |
| WO | 2006009826 | A1 | 1/2006 |
| WO | 2008077597 | A1 | 7/2008 |
| WO | 2008141020 | A1 | 11/2008 |
| WO | 2008145616 | A1 | 12/2008 |
| WO | 2008154241 | A1 | 12/2008 |
| WO | 2010010190 | A1 | 1/2010 |
| WO | 2010030592 | A1 | 3/2010 |
| WO | 2010059658 | A1 | 5/2010 |
| WO | 2011046771 | A1 | 4/2011 |
| WO | 2011053948 | A1 | 5/2011 |
| WO | 2011140333 | A1 | 11/2011 |
| WO | 2012082566 | A1 | 6/2012 |
| WO | 2016025129 | A1 | 2/2016 |

OTHER PUBLICATIONS

Arkin, et al., Small-molecule inhibitors of protein—protein interactions: progressing towards the dream, Nat Rev Drug Disco., 2004, pp. 301-317, vol. 3, No. 4.

Bartalena, et al., Thyroid hormone transport proteins, Clin Lab Med, 1993, pp. 583-598, vol. 13, No. 3.

Baures, STN International Hcaplus database, (Columbus, Ohio), Accession No. 1998:617889, 1998.

Blake, et al., Structure of prealbumin: Secondary, tertiary and quaternary interactions determined by Fourier refinement at 1.8 A, J Mol Biol, 1978, pp. 339-356, vol. 121, No. 3.

Buxbaum, et al., Significance of the Amyloidogenic Transthyretin Val 122 ile allele in African Americans in the Arteriosclerosis Risk in Communities (ARIC) and Cardiovascular Health (CHS) Studies, Am Heart J, 2010, pp. 864-870, vol. 159.

Buxbaum, et al., Transthyretin protects Alzheimer's mice from the behavioral and biochemical effects of A. toxicity, Proc Natl Acad Sci., 2008, pp. 2681-2686, vol. 105, No. 7.

Chang, et al., Evolution of thyroid hormone binding by transthyretins in birds and mammals, Eur J Biochem., 1999, pp. 534-542, vol. 259.

Choi, et al., "Accelerated AB Deposition in APPswe/PS1 delta E9 Mice with Hemizygous Deletions of TTR (Transthyretin)", J Neurosci, 2007, pp. 7006-7010, 27(26).

Choi, et al., Antidiabetic actions of a non-agonist PPARy ligand blocking Cdk5-mediated phosphorylation, Nature, 2011, pp. 477-481.

Coelho, Familial amyloid polyneuropathy: new developments in genetics and treatment, Current opinion opinion in neurology, 1996, pp. 355-359, vol. 9, No. 5.

Connelly, et al., Structure-based design of kinetic stabilizers that ameliorate the transthyretin amyloidosis, Current Opinion in Structural Biology, 2010, pp. 54-62, vol. 20, No. 1.

Connors, et al., Cardiac amyloidosis in African Americans: Comparison of clinical and laboratory features of transthyretin V122I amyloidosis and immunoglobulin light chain amyloidosis, Am Heart J, 2009, pp. 607-614, vol. 158, No. 4.

Diana, et al., Synthesis and antiherpetic activity of some 4-[(aryloxy)alkyl]pyrazoles, Journal of Medicinal Chemistry, 1981, pp. 731-735, vol. 24, No. 6.

Emerson, et al., NMR characterization of interleukin-2 in complexes with the IL-2Ralpha receptor component, and with low molecular weight compounds that inhibit the IL-2/IL-Ralpha interaction, Protein Sci., 2003, pp. 811-822, vol. 12, No. 4.

Falk, et al., The Systemic Amyloidoses, N. Eng. J. Med., 1997, pp. 898-909, vol. 337.

Farr, et al., STN International HCAPLUS database, Accession No. 2001:338762, 2007.

Gell, et al. The Detection and Quantitation of Protein Oligomerization, Adv Exp Med Biol., 2012, pp. 19-41, vol. 747.

Haigis, et al., The Aging Stress Response, Mol Cell, 2010, pp. 333-344, vol. 40, No. 2.

He, et al., Small-molecule inhibition of TNF-alpha, Science, 2005, pp. 1022-1025, vol. 310, No. 5750.

Hull, et al., Islet amyloid: a critical entity in the pathogenesis of type 2 diabetes, J. Clin. Endocrinol & Metab, 2004, pp. 3629-3643, vol. 89, No. 8.

Jacobson, et al., Variant-Sequence Transthyretin (Isoleucine 122) in Late-Onset Cardiac Amyloidosis in in Black Americans, N. Engl J Med, 1997, pp. 466-473, vol. 336.

Jiang, et al., The V122I cardiomyopathy variant of transthyretin increases the velocity of rate-limiting tetramer dissociation, resulting in accelerated amyloidosis, Proc Natl Acad Sci USA, 2001, pp. 14943-14948, vol. 98, No. 26.

Joao, et al., Transthyretin mutations in health and disease, Hum Mutat, 1995, pp. 191-196, vol. 5.

Johnson, et al., Native State Kinetic Stabilization as a Strategy to Ameliorate Protein Misfolding Diseases: A on the Transthyretin Amyloidoses, Ace Chem Res, 2005, pp. 911-921, vol. 38, No. 12.

Katritzky, et al., Mannich reactions of carbonyl compounds and enamines with benzotriazole as the NH component, Journal of Heterocyclic Chemistry, 1994, pp. 917-923, vol. 31, No. 4.

Koehler, et al., Discovery of an inhibitor of a transcription factor using small molecule microarrays and diversity-oriented synthesis, J Am Chem Soc, 2003, pp. 8420-8421, vol. 125, No. 28.

Maher, et al., Synthesis of some new 3-(2'-heterocyclicethyl)-2-methyl-3,4-dihydroquinazolin-4-one derivatives as antimicrobial agents, J Chem Tech & Biotech, 1992, pp. 209-215, vol. 55, No. 3.

Miller, et al., Enthalpy-Driven Stabilization of Transthyretin by AG10 Mimics a Naturally Occurring Genetic Variant That Protects from Transthyretin Amyloidosis, Journal of Medicinal Chemistry, Aug. 22, 2018, pp. 7862-7876, vol. 61, No. 17.

Miyawaki, Development of Probes for Cellular Functions Using Fluorescent Proteins and Fluorescence Resonance Energy Transfer, Annu Rev Biochem., 2011, pp. 357-373, vol. 7, No. 80.

Monaco, et al., Structure of a complex of two plasma proteins: transthyretin and retinol-binding protein, Science, 1995, pp. 1039-1047, vol. 268, No. 5231.

(56) References Cited

OTHER PUBLICATIONS

Ouyang, et al., Syntheses of 4-(2-Hydroperoxy-2,2- diarylethyl)-3,5-dimethylpyrazoles, 4-(2Hydroxy-2,2-diarylethyl)-3,5-dimethylpyrazoles, and the Related Compounds, Journal of Heterocyclic Chemistry, 1996, pp. 1291-1302, vol. 33, No. 4.
Penchala, et al., A Biomimetic Approach for Enhancing the in Vivo Half-Life of Peptides, Nature Chemical Biology, 2015, vol. 11, No. 10.
Penchala, et al., AG10 inhibits amyloidogenesis and cellular toxicity of the familial amyloid cardiomyopathy-asssociated V122I transthyretin, Proc Natl Acad Sci USA, Jun. 11, 2013, pp. 9992-9997, vol. 110, No. 24.
Peterson, et al., Inhibiting transthyretin conformational changes that lead to amyloid fibril formation, Proc Natl Acad Sci USA, 1998, pp. 12956-12960, vol. 95, No. 22.
Prapunpoj, et al., Change in structure of the N-terminal region of transthyretin produces change in affinity of transthyretin to T4 and T3, FEBS J, 2006, pp. 4013-4023, vol. 273, No. 17.
Ran, et al., Non-Conjugated Small Molecule FRET for Differentiating Monomers from Higher Molecular Weight Amyloid Beta Species, PLoS One, Apr. 2011, pp. 1-6, vol. 6, No. 4.
Reixach, et al., Tissue damage in the amyloidoses: Transthyretin monomers and nonnative oligomers are the major cytotoxic species in tissue culture, PNAS, Mar. 2, 2004, pp. 2817-2822.
Rickert, et al., The Structure of Interleukin-2 Complexed with its Alpha Receptor, Science, 2005, pp. 1477-1480, vol. 308, No. 5727.
Saraiva, et al., Transthyretin mutations in hyperthyroxinemia and amyloid diseases, Hum Mut., 2001, pp. 493-503, vol. 17, No. 6.
Sekijima, et al., Pathogenesis of and Therapeutic Strategies to Ameliorate the Transthyretin Amyloidoses, Curr Pharm Des, 2008, pp. 3219-3230, vol. 14, No. 30.
Selkoe, et al., Cell Biology of protein misfolding: The examples of Alzheimer's and Parkinson's diseases, diseases, Nat Cell Biol 6, 2004, pp. 1054-1061.
Selkoe, et al., Folding proteins in fatal ways, Nature, 2003, pp. 900-904, vol. 426.
Stefani, Protein misfolding and aggregation: new examples in medicine and biology of the dark side of the protein world, Biochimica et biophysica acta, 2004, pp. 5-25, vol. 1739.
Suhr, et al., Liver Transplantation for Hereditary Transthyretin Amyloidosis, Transpl, 2000, pp. 263-276, vol. 6, No. 3.
Wiseman, et al., Kinetic Stabilization of an Oligomeric Protein by a Single Ligand Binding Event, Am Chem Soc, 2005, pp. 5540-5551, vol. 127.
Wojtczak, et al., Structures of Human Transthyretin Complexed with Thyrixine at 2.0 A Resolution and 3', 5'-Dinitro-N-aceytyl-L-thyronine at 2,2 A Resolution, Acta Cryst., 1996, pp. 758-765, vol. D52.
Yamauchi, et al., STN International HAPLUS database, (Columbus, Ohio), Accession No. 2003:155526.
Zefirov, et al., Ring-Opening Reactions of 1,1-diacetylcyclopropane with Hydrazine and Hydroxylamine Derivatives as the Novel Synthesis of p-X-ethyl Substituted Pyrazoles and Isoxazoles, Tetrahedron, 1982, pp. 1693-1697, vol. 38, No. 11.

* cited by examiner

| Rat | | |
|---|---|---|
| IV 1mg/kg | | |
| T$_{1/2}$ | Vd$_{SS}$ | Cl |
| (h) | (L/kg) | (mL/min/kg) |
| 11.92 ± 1.75 | 0.41 ± 0.02 | 0.49 ± 0.11 |
| PO 5mg/kg | | |
| %F | | |
| (%) | | |
| 60.5 | | |

| Mouse | | |
|---|---|---|
| IV 1mg/kg | | |
| T$_{1/2}$ | Vd$_{ss}$ | Cl |
| (h) | (L/kg) | (mL/min/kg) |
| 5.32 ± 0.62 | 0.47 ± 0.13 | 1.13 ± 0.26 |
| PO 5mg/kg | | |
| %F | | |
| (%) | | |
| 30.4 | | |

| PRS Dog 1 Day | | |
|---|---|---|
| C_max | C_min (24h) | AUC (24hr) |
| (ng/mL) | (ng/mL) | ng·hr/mL |
| n=4, ± SD | n=4, ± SD | n=4 |
| PO 5mg/kg | | |
| 3143 ± 257.7 | 1490 ± 352.4 | 44785 ± 5078.4 |
| PO 20mg/kg | | |
| 7903 ± 3511.5 | 1573 ± 323.9 | 63343 ± 5387.8 |
| PO 20mg/kg Capsule | | |
| 10288 ± 3171.2 | 1853 ± 264.6 | 79043 ± 10019.9 |

*AUC does not include expected $T_{max}$ at 1 hr
AUC calculated by MS Excel

| PRS Dog 1 Day Male | | |
|---|---|---|
| $C_{max}$ | $C_{min}$ (24h) | AUC (24hr) |
| (ng/mL) | (ng/mL) | ng·hr/mL |
| n=2, ± SD | n=2, ± SD | n=2 |
| PO 5mg/kg | | |
| 3140 ± 198.0 | 1540 ± 99.0 | 46940 ± 1244.5 |
| PO 20mg/kg | | |
| 7490 ± 2474.9 | 1735 ± 289.9 | 65060 ± 6010.4 |
| PO 20mg/kg Capsule | | |
| 11090 ± 4963.9 | 1750 ± 396.0 | 70925 ± 5805.3 |

*AUC does not include expected $T_{max}$ at 1 hr
AUC calculated by MS Excel

| PRS Dog 1 Day Female | | |
|---|---|---|
| $C_{max}$ | $C_{min}$ (24h) | AUC (24hr) |
| (ng/mL) | (ng/mL) | ng·hr/mL |
| n=2, ± SD | n=2, ± SD | n=2 |
| PO 5mg/kg | | |
| 2945 ± 63.6 | 1440 ± 594.0 | 42630 ± 7566.0 |
| PO 20mg/kg | | |
| 8315 ± 5494.2 | 1410 ± 353.6 | 61625 ± 6257.9 |
| PO 20mg/kg Capsule | | |
| 9485 ± 1718.3 | 1955 ± 106.1 | 871603 ± 1979.9 |

*AUC does not include expected $T_{max}$ at 1 hr
AUC calculated by MS Excel

PROCESS FOR PREPARING AG-10, ITS INTERMEDIATES, AND SALTS THEREOF

CROSS-REFERENCES TO RELATED APPLICATIONS

This application claims the benefit of priority under 35 U.S.C § 119(e) to U.S. Provisional Application Ser. No. 62/460,576 filed Feb. 17, 2017, the disclosure of which is incorporated herein by reference in its entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Aberrant protein interaction and aggregation, either through protein misfolding or over activation of a signaling pathway is the underlying cause of a large number of human degenerative diseases. As such, targeting protein protein interactions (PPIs) is of therapeutic interest.

To date approved inhibitors of PPIs are proteins rather than small-molecules inhibitors. For example, therapeutic monoclonal antibodies (mAbs) are use in treating cancer, autoimmune, infectious, and neuodegenerative diseases. Therapeutic mAbs are costly to manufacture, they require administration by injection, and can illicit an immune-response in the patient. For these reasons the development of small-molecule inhibitors of PPIs is of interst.

One such example of aberrant protein aggregation is the soluble protein transthyretin (TTR or prealbumin). TTR is a 55 kDa homotetrameric protein present in blood and cerebrospinal fluid. When dissociated from its homoterameric form, TTR dimers can misfold into amyloidogenic monomers. This has been observed with the wild type TTR as well as more than 100 different mutated variants. Research has shown that stabilizing the tetrameric form of TTR inhibits the misfolding of amyloidogenic monomers and subsequent TTR amyloid formation.

Recent work has identified 3-(3-(3,5-dimethyl-1H-pyrazol-4-yl)propoxy)-4-fluorobenzoic acid (AG-10) as a promising candidate to treat TTR amyloid related diseases such as TTR amyloid cardiomyopathy. This compound has been disclosed in WO 2014/100227. Notably, the disclosure does not provide any additional forms of AG-10 and the method of synthesis described would not be suitable for industrial manufacturing.

As such, there exists a need to produce improved methods of synthesizing AG-10 and to provide additional forms of AG-10 that offer advantageous pharmacokinetic properties. The present disclosure addresses these needs and provides related advantages as well.

BRIEF SUMMARY

In one aspect, the present disclosure provides an improved method for preparing a compound of Formula IX

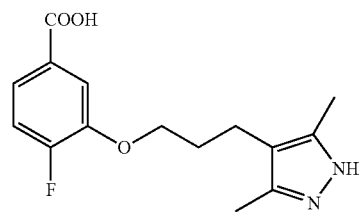

comprising
(a) contacting a compound of Formula II

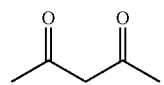

with a compound of Formula III

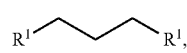

a first base, and a first organic solvent to provide a compound of Formula IV

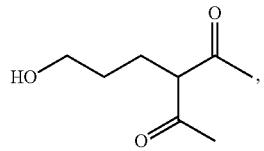

wherein each $R^1$ is independently a halogen or a sulfonate ester;
(b) contacting a compound of Formula IV with hydrazine and a second organic solvent to provide a compound of Formula V

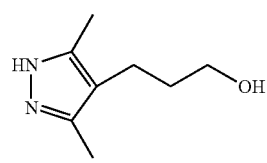

(c) contacting a compound of Formula V with a sulfonating agent or halogenating agent to provide a compound of Formula VI

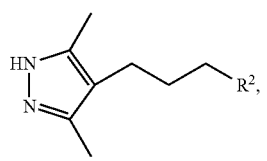

wherein $R^2$ is a halogen or a sulfonate ester;

(d) contacting a compound of Formula VI with a compound of Formula VII

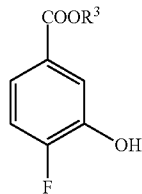

(VII)

a second base, and an third organic solvent to provide a compound of Formula VIII

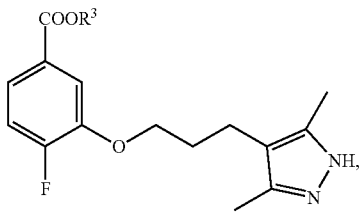

(VIII)

wherein $R^3$ is selected from the group consisting of an $C_{1-12}$ alkyl, $C_{2-12}$ alkenyl, $C_{1-12}$ alkynyl, $C_{3-8}$cycloalkyl, heterocycloalkyl, aryl, and heteroaryl, each of which is optionally substituted.

(e) contacting a compound of Formula VIII with a third base to provide a compound of Formula IX.

In a second aspect, the present disclosure provides a phamraceutically acceptable salt respresented by Formula I or Ib

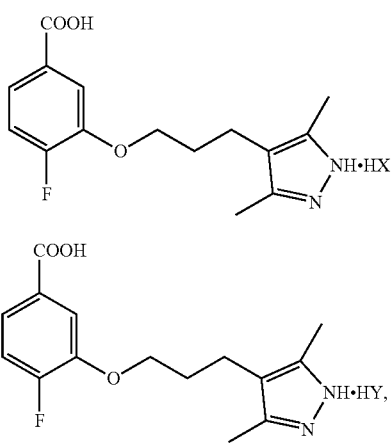

(I)

(Ib)

wherein X is a pharmaceutically acceptable anion of a protic acid, and Y is a multiprotic acid.

In a third aspect, the present disclosure provides crystalline types A-K of Formula IX.

Other features, elements, and aspects of the present disclosure will be apparent from the accompanying drawings and from the detailed description that follows.

DETAILED DESCRIPTION

I. General

The present disclosure, in part, provides an improved process for the preparation of a compound of Formula IX (AG-10) and intermediates thereof. The newly described process provides high yields and improved efficiency.

Figure 1:
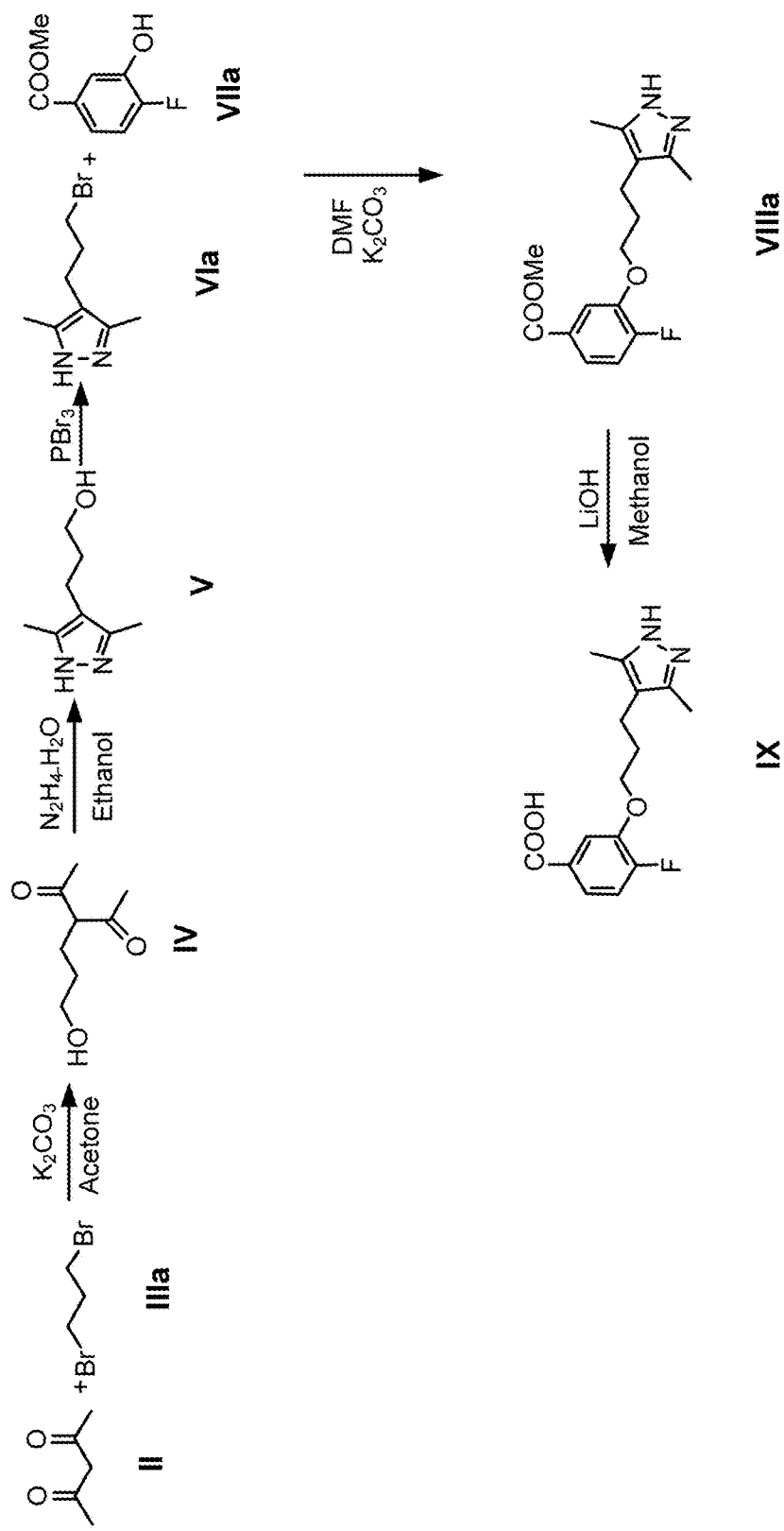
FIG. 1 provides a scheme as described herein for the preparation of AG-10 and its intermediates.

While a complete synthetic scheme is provided in the summary of the invention, as well as Scheme 1 (FIG. 1), one of skill in the art will appreciate that selected steps of the instant process are novel and can be performed independent of the origin of the starting material or intermediates.

Also provided herein is a pharmaceutically acceptable salt of Formula I and Formula Ib. Pharmaceutically acceptable salts of Formula I and Formula Ib possess surprising pharmacokinetic properties which improves the bioavailability of the compound of Formula IX. Without being bound to any particular theory, it is believed that the pharmaceutically acceptable salt of Formula I and Formula Ib provide a protonated pyrazole on the compound of formula IX that pairs with the anion of the protic acid or multiprotic acid. Unlike pharmaceutically acceptable salts of Formula I and Formula Ib, salts prepared from alkali hydroxides, such as NaOH, or the zwitterion of the compound of Formula DC do not provide the advantageous features described herein. In particular embodiments the compound of formula I is represented by the compound of Formula Ia, the HCl salt of Formula I.

II. Definitions

The term "compound of Formula IX" refers to 3-(3-(3,5-dimethyl-1H-pyrazol-4-yl)propoxy)-4-fluorobenzoic acid, also known as AG-10, a compound with the following structure

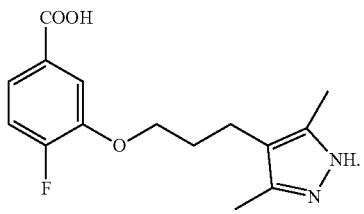 [SMILES: Cc1n[nH]c(C)c1CCCOc1cc(C(=O)O)ccc1F]

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted. Particular substituents include, hydroxyl, halogen, alkoxy and amino groups. A person of skill in the art will recognize that a number of substituents may be added to alkyl groups without departing from the teachings herein.

The term "alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups, like the alkyl groups describe above, can be substituted or unsubstituted.

The term "alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups, like the alkyl groups describe above, can be substituted or unsubstituted.

The term "cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, and cyclohexyl. Cycloalkyl groups can also be partially unsaturated, having one or more double or triple bonds in the ring. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. Cycloalkyl groups can be substituted or unsubstituted. As a person of skill in the art will recognize, many different substituents of cycloalkyl groups can be included without departing from the teachings herein.

The term "heterocycloalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. Heterocycloalkyl groups, like the cycloalkyl groups describe above, can be substituted or unsubstituted.

The term "aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups, like the cycloalkyl groups describe above, can be substituted or unsubstituted.

The term "heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine thiophene, furan, thiazole, isothiazole, oxazole, and isoxazole. Heteroaryl groups, like the cycloalkyl groups describe above, can be substituted or unsubstituted.

The term "halogen" refers to fluorine, chlorine, bromine and iodine.

The term "hydrated" refers to a chemical reagent that contains water. Hydrated, in the context of the chemical conversion of step (a) refers to a chemical reagent with a sufficient amount of water to complete the chemical conversion shown. In particular embodiments, a hydrated reagent includes at least 1%, 2%, 3%, 4%, 5%, 6%, 7%, 8%, 9%, 10%, 15%, or 20% by weight water content.

III. Embodiments of the Disclosure

A. Process for Preparing a Compound of Formula IX

In one aspect, the present disclosure provides an improved method for prepairing a compound of Formula IX

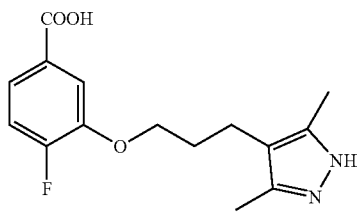

(IX)

comprising (a) contacting a compound of Formula II

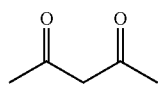

(II)

with a compound of Formula III

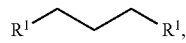

(III)

a first base, and a first organic solvent to provide a compound of Formula IV

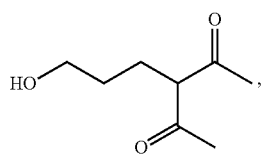

(IV)

wherein each $R^1$ is independently a halogen or a sulfonate ester;

(b) contacting a compound of Formula IV with hydrazine and a second organic solvent to provide a compound of Formula V

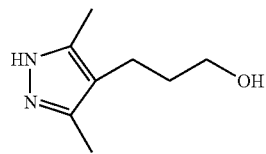

(V)

(c) contacting a compound of Formula V with a sulfonating agent or halogenating agent provide a compound of Formula VI

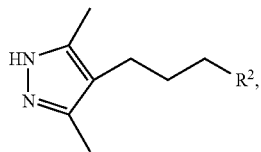

(VI)

wherein $R^2$ is a halogen or a sulfonate ester;

(d) contacting a compound of Formula VI with a compound of Formula VII

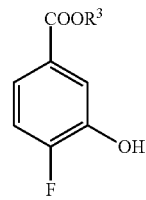

(VII)

a second base, and an third organic solvent to provide a compound of Formula VIII

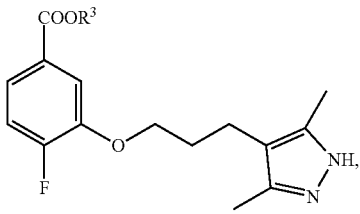

(VIII)

wherein $R^3$ is selected from the group consisting of an $C_{1-12}$ alkyl, $C_{2-12}$ alkenyl, $C_{1-12}$ alkynyl, Cmcycloalkyl, heterocycloalkyl, aryl, and heteroaryl, each of which is optionally substituted.

(e) contacting a compound of Formula VIII with a third base to provide a compound of Formula IX.

Step (a), comprises contacting a first base and an organic solvent with a compound of Formula II

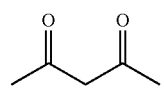

(II)

and a compound of Formula III

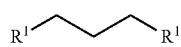
(III)

to provide a compound of Formula IV

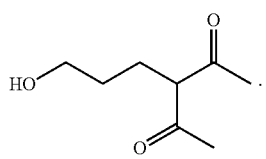
(IV)

A person of skill in the art will recognize that the compound of Formula IV has both nucleophilic and electrophilic sites and that depending on the reaction conditions intramolecular conversions are possible. For example, under some conditions, the alcohol group of Formula IV may add to one of the carbonyl carbons to form a six membered ring (Formula IVa). When the afore mentioned addition is coupled with a subsequent elimination reaction, the compound of Formula IV has the structure of Formula IVb. It is further apparent to a person of skill in the art that the compound of Formula IV can also exist as the enol tautomer of Formula IVc.

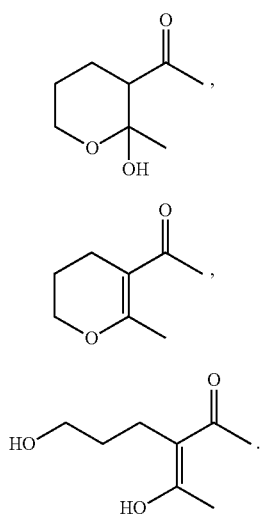

(IVa)

(IVb)

(IVc)

The compounds of Formula IV, Formula IVa, Formula IVb, Formula IVc interconvert, and depending on the reaction conditions varying concentrations of these species are present. In some embodiments, only a single species is present.

There are many suitable bases which may be used in this conversion. For example, in some embodiments, the first base is an alkali metal carbonate, an alkali metal bicarbonate or a combination thereof. Alkali metal carbonates can include, but are not limited to $Li_2CO_3$, $Na_2CO_3$, and $K_2CO_3$, and alkali metal bicarbonates can include, but are not limited to $LiHCO_3$, $NaHCO_3$, and $KHCO_3$. In some embodiments, the alkali metal carbonate is $K_2CO_3$.

The organic solvent of step (a) is one which will suitably dissolve both compounds of Formula II and Formula III in solution, and be miscible with the base being used. A person of skill in the art will recognize that there are a number of organic solvents which meet these specifications. In some embodiments, the first organic solvent is a polar organic solvent. In some embodiments, the polar organic solvent is selected from the group consisting of acetone, ethyl acetate, dichloromethane, tetrahydrofuran, dimethylformamide and acetonitrile. In some embodiments, the organic solvent is acetone.

The conversion of step (a) also includes at least 1 equivalent of water to produce the hydroxyl containing compound of Formula IV. Often, this equivalent of water is provided by the reagents or solvents in the reaction, such as the first base or the organic solvent, rather than the direct addition of water. It has been found that the use of hydrated base in the chemical conversion of step (a) provides an exceptionally efficient conversion. As such, in some embodiments, the first base in the conversion of step (a) is a hydrated base. In some embodiments, the first base is a hydrated alkali metal carbonate. In some embodiments, the first base is a hydrated $K_2CO_3$.

The compound of Formula III includes two $R^1$ groups, each of which are independently selected from the group consisting of chloride, bromide, tosylate, and mesylate.

In some embodiments, each $R^1$ is bromide.

It can be seen that each $R^1$ group acts as a leaving group in the conversion in step (a); thus, a person of skill in the art will recognize that other leaving groups are useful in the present invention and do not depart from the teachings herein.

In some embodiments, the compound of Formula IV provided in step (a) is used directly in the conversion of step (b) without purification.

Turning to step (b), the chemical conversion described comprises a compound of Formula IV

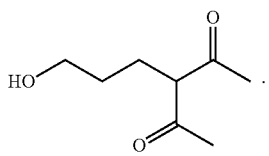
(IV)

with hydrazine ($N_2H_4$) and a second organic solvent to provide a compound of Formula V

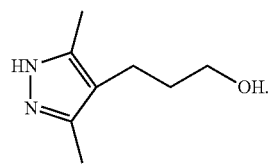
(V)

A person of skill in the art will recognize that a variety of different solvents can be used as the second organic solvent in this conversion. In some embodiments, the second organic solvent is a polar protic organic solvent. In some embodiments, the polar protic organic solvent is $C_{1-8}$—OH. In some embodiments, the polar protic organic solvent is ethanol.

In some embodiments, the compound of Formula V provided in step (b) is used directly in the conversion of step (c) without purification.

The chemical conversion of step (c) includes the replacement of the hydroxyl moiety in the compound of Formula (V) with halogen or the conversion of the hydroxyl to a sulfonate ester to provide a compound of Formula (VI)

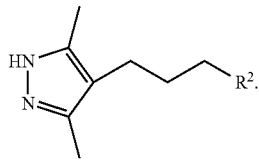
(VI)

Although sulfonating agents or halogenating agents are particularly envisioned as starting materials in this conversion, a person of skill in the art will recognized that many different leaving groups beyond halogens and sulfate esters are appropriate substituents for $R^2$. Thus, any starting material that will yield a suitable leaving group at the $R^2$ position is within the scope of this invention.

There are a number of solvents which are suitable for this conversion; however, a person of skill in the art will recognize that the solvent chosen for this chemical conversion will depend upon the sulfonating agent or halogenating agent chosen, as particular solvents might not be suitable for all starting materials. For example, when contacting the compound of Formula V with a halogenating agent, polar organic solvents are particularly useful. In some embodiments, the polar organic solvent is 1,2-dichloroethane.

Halogenating agents useful in the conversion of step (c) include, but are not limited to, $PBr_3$, $PCl_3$, $PCl_5$, $SOBr_2$, $PBr_5$, and $SOCl_2$. Sulfonating agents of the conversion of step (c) include, but are not limited to, mesyl chloride (MsCl) and tosyl chloride (TsCl). In some embodiments, the halogenating agent is $PBr_3$.

It is understood that the identity of $R^2$ is dependent upon the starting material chosen for the chemical conversion in step (c). For example, if a sulfonating agent is chosen, the identity of $R^2$ is the corresponding sulfate. In some embodiments, $R^2$ is chloride, bromide, tosylate, and mesylate. In some embodiments, $R^2$ is Br.

Focusing on step (d), the compounds of Formula VI

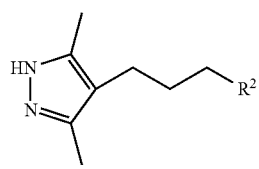
(VI)

and Formula VII

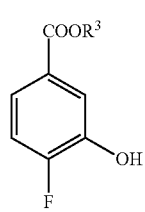
(VII)

are contacted in the presence of a base and a third organic solvent to provide a compound of Formula VIII

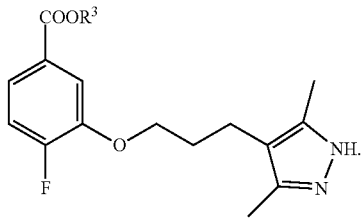
(VIII)

The chemical conversion of step (d) can be performed with a variety of different bases. For example, in some embodiments, the second base is an alkali metal carbonate, an alkali metal bicarbonate or a combination thereof. Alkali metal carbonates can include, but are not limited to $Li_2CO_3$, $Na_2CO_3$, and $K_2CO_3$, and alkali metal bicarbonates can include, but are not limited to $LiHCO_3$, $NaHCO_3$, and $KHCO_3$. In some embodiments, the alkali metal carbonate is $K_2CO_3$.

The organic solvent of step (d) is one which will suitably dissolve both compounds of Formula VI and Formula VII in solution, and be miscible with the base being used. A person of skill in the art will recognize that there are a number of organic solvents which meet these specifications. In some embodiments, the third organic solvent is a polar aprotic organic solvent. In some embodiments, the polar organic solvent is selected from the group consisting of acetone, ethyl acetate, dichloromethane, tetrahydrofuran, dimethylformamide, dimethyl sulfoxide, and acetonitrile. In some embodiments, the third organic solvent is dimethylformamide. In some embodiments, the third organic solvent is dimethyl sulfoxide.

Suitable substituents for the $R^3$ group include those which will not interfere with the chemical conversion of step (e), discussed in more detail below. Such substituents, include, but are not limited to $C_{1-8}$alkyl, $C_{3-8}$ cycloalkyl, $C_{3-12}$heterocycloalkyl, aryl, heteroaryl, etc. A person of skill in the art will recognize that many other ester substituents of $R^3$ are suitable without departing from the teachings herein. In some embodiments, $R^3$ is $C_{1-8}$alkyl. In some embodiments, $R^3$ is methyl.

In some embodiments, the process of step (d) provides a compound of Formula VIII with at least a 70% yield (mol/mol) relative to the amount of Formula VII.

With respect to step (e), a compound of Formula VIII

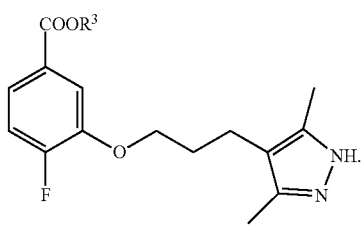
(VIII)

is contacted with a third base to provide a compound of Formula IX

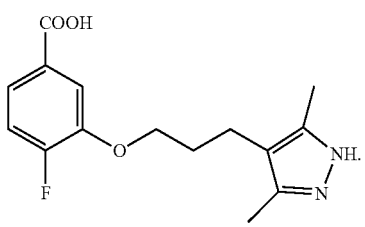

(IX)

The third base in the chemical conversion of step (e) can be a number of different bases. For example, in some embodiments, the third base is a metal hydroxide. In some embodiments, the metal hydroxide is an alkali metal hydroxide. In some embodiments, the alkali metal hydroxide is a selected from the group consisting of LiOH, NaOH, KOH, RbOH, and CsOH. In some embodiments, the alkali metal hydroxide is LiOH. In some embodiments, the alkali metal hydroxide is NaOH.

A person of skill in the art will recognize that a variety of different solvents can be used as the solvent in conversion of step (e). For instance, in some embodiments, the second organic solvent is a polar protic organic solvent or water. In some embodiments, the polar protic organic solvent is $C_{1-8}$—OH. In some embodiments, the polar protic organic solvent is methanol. In some embodiments, the solvent is water. In some embodiments, the solvent is a combination of methanol and water.

In some embodiments, the process in step (e) further comprises
(e-i) removing the solvent to provide a residue;
(e-ii) dissolving the residue in water to form a solution;
(e-iii) acidifying the solution to form a precipitate; and
(e-iv) filtering the solution to provide isolated Formula IX,
wherein steps (e-i) to (e-iv) is performed after step (e).

Step (e-i) may be performed using any suitable removal step such as reduced pressure, temperature elevation, or a combination of both. In some embodiments, the solvent is removed under reduced pressure. In some embodiments, a solid is produced in step (e) and the solvent is removed via filtration. Further, the addition of water in step (e-ii) can be performed prior to step (e-i). In such event, the removal of the solvent via reduced pressure provides a concentrated aqueous component (i.e. the water is not removed). It is understood that the re-ordering of steps (e-i) and (e-ii) does not depart from the processes described herein.

Step (e-iii) may be acidified with any suitable acid. In some embodiments, the suitable acid is HCl. In some embodiments, the solution is acidified to a pH of below 3, 0-3, or 2-3. In some embodiments the solution is acidified to a solution of about 2. In some embodiments, the solution is acidified to a pH of below 2, 0-2, or 1-2. In some embodiments, the solution is acidified to a pH of about 1.4-1.6.

The pH of the acidifying step (e-iii) determines the predominant species produced. In some embodiments, the pH of the acidifying step is in the range of 5-6 and the zwitterionic form of Formula IX is produced. In some embodiments, the pH is acidified with HCl to less than about 2 or in the range of 1.4 to 1.6 and the HCl salt of Formula IX is produced (i.e. the compound of Formula Ia).

The process described in step (e) can produce a compound of Formula IX with high yield and purity. In some embodiments, the yield of step (e) is greater than 85%, 90%, 93%, or 95% (mol/mol) relative to Formula VIII. In some embodiments the purity of the compound of Formula IX produced in step (e) is greater than 80%, 85%, 90%, 95%, or 97% pure (mol/mol).

In another aspect, provided herein is a method of preparing a compound of Formula IX

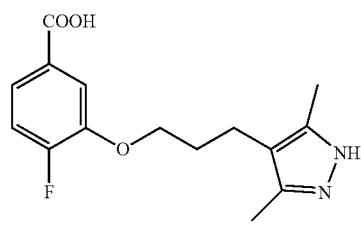

(IX)

comprising
(a) contacting a compound of Formula II

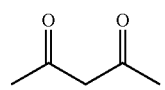

(II)

with a compound of Formula III

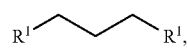

(III)

a first base, and a first organic solvent to provide an adduct
wherein each $R^1$ is independently a halogen or a sulfonate ester;
(b) contacting the adduct with hydrazine and a second organic solvent to provide a compound of Formula V

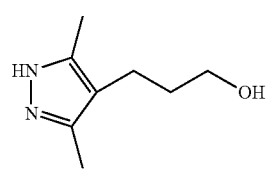

(V)

(c) contacting a compound of Formula V with a sulfonating agent or halogenating agent provide a compound of Formula VI

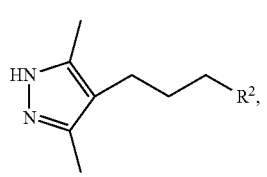

(VI)

wherein $R^2$ is a halogen or a sulfonate ester;
(d) contacting a compound of Formula VI with a compound of Formula VII

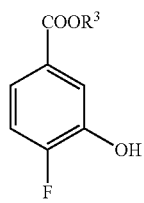
(VII)

a second base, and an third organic solvent to provide a compound of Formula VIII

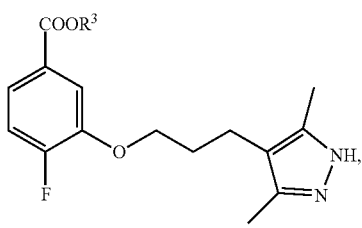
(VIII)

wherein $R^3$ is selected from the group consisting of an $C_{1-12}$ alkyl, $C_{2-12}$ alkenyl, $C_{1-12}$ alkynyl, $C_{3-8}$cycloalkyl, heterocycloalkyl, aryl, and heteroaryl, each of which is optionally substituted.

(e) contacting a compound of Formula VIII with a third base to provide a compound of Formula IX.

In some embodiments, the adduct produced in step (a) is a compound of Formula IV, Formula IVa, Formula IVb, and/or Formula IVc.

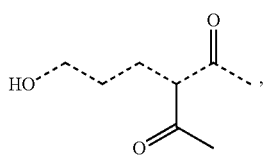
(IV)

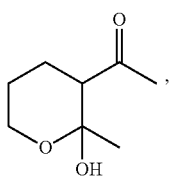
(IVa)

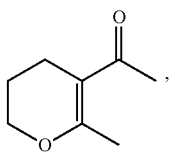
(IVb)

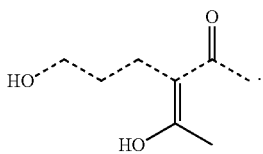
(IVc)

A person of skill in the art will recognize that the compounds shown above can interconvert and that the relative amounts of each compound are dependent on the experimental conditions.

As noted above, a person of skill in the art will appreciate that selected steps in the process may be conducted independent of the origin of starting material or intermediates.

B. Pharmaceutically Acceptable Salts of Formula I

In a second aspect, the present disclosure provides a phamraceutically acceptable salt respresented by Formula I

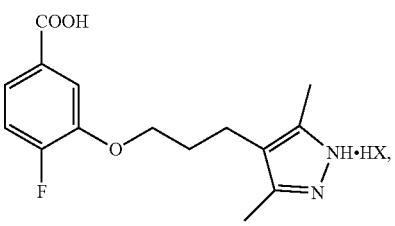
(I)

wherein X is a pharmaceutically acceptable anion of a protic acid.

A variety of protic acids are suitable for making a pharmaceutically acceptable salt of Formula I. It can be seen that the pharmaceutically acceptable anion of the protic acid is dependent upon the protic acid used. For example, protic acids useful in the present disclosure include hydrochloric acid, hydrobromic acid, sulfonic acid, tosylic acid (p-toluenesulfonic acid), methanesulfonic acid, nitric acid, or acetic acid. Thus, pharmaceutically acceptable anions of a protic acid include chloride ($Cl^-$), bromide ($Br^-$), sulfonate ($HS(O)_2O^-$), tosylate ($TsO^-$), mesylate ($MsO^-$), besylate ($BeO^-$), ethanesulfonate ($EtSO_3^-$), nitrate ($NO_3^-$), acetate ($CH_3C(O)O^-$), glycolate ($HO-CH_2-C(O)O^-$), or combinations thereof.

In some embodiments, the pharmaceutically acceptable anion of a protic acid is mesylate. In some embodiments, the mesylate salt of Formula IX characterized by an X-ray powder diffraction pattern substantially in accordance with FIG. 4.

In some embodiments, the pharmaceutically acceptable anion of a protic acid is besylate. In some embodiments, the mesylate salt of Formula IX characterized by an X-ray powder diffraction pattern substantially in accordance with FIG. 8.

In some embodiments, the pharmaceutically acceptable anion of a protic acid is tosylate. In some embodiments, the tosylate salt of Formula IX characterized by an X-ray powder diffraction pattern substantially in accordance with FIG. 10.

In some embodiments, the pharmaceutically acceptable anion of a protic acid is esylate. In some embodiments, the esylate salt of Formula IX characterized by an X-ray powder diffraction pattern substantially in accordance with FIG. 12.

In some embodiments, the pharmaceutically acceptable anion of a protic acid is bromide. In some embodiments, the bromide salt of Formula IX characterized by an X-ray powder diffraction pattern substantially in accordance with FIG. 14.

In some embodiments, the pharmaceutically acceptable anion of a protic acid is nitrate. In some embodiments, the nitrate salt is characterized by an XRPD pattern substantially in accordance with FIG. 16. In some embodiments, the nitrate salt is characterized by an XRPD pattern substantially in accordance with FIG. 18.

In some embodiments, the pharmaceutically acceptable anion of a protic acid is chloride, and the pharmaceutically acceptable salt of Formula I is represented by Formula (Ia)

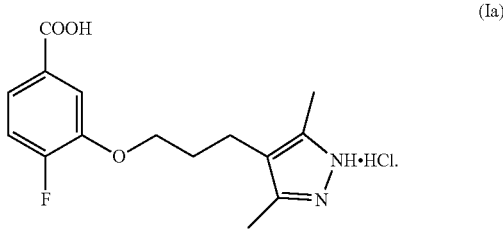

(Ia)

In some embodiments, the salt of Formula Ia is crystalline Type A. In some embodiments, crystalline Type A of Formula Ia is characterized by an X-ray powder diffraction pattern comprising peaks at 12.0, 21.8, 25.9, 26.7, and 27.9 degrees 2θ (±0.2 degrees 2θ). In some embodiments, the X-ray powder diffraction pattern further comprises one or more peaks at 7.0, 10.3, 13.9, 15.6, and/or 17. Crystalline Type A of Formula Ia characterized by an X-ray powder diffraction pattern substantially in accordance with FIG. 31.

In some embodiments, a multiprotic acid, such as a diprotic or triprotic acid, are used to make pharmaceutically acceptable salts of Formula IX. In such embodiments, the pliaimaceutically acceptable salt is represented by Formula Ib

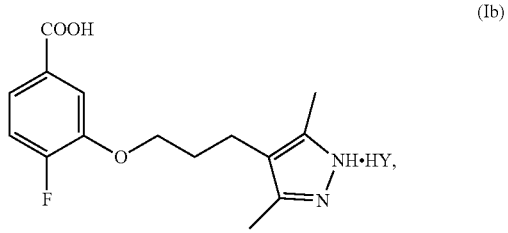

(Ib)

where Y is a multiprotic acid.

In some embodiments, Y is selected from the group consisting of ethane-1,2,-disulfonic acid, sulfuric acid, citric acid, maleic acid, malic acid, tartaric acid, and oxalic acid. In some embodiments, Y is L-malic acid or L-tartaric acid.

In some embodiments Y is ethane-1,2,-disulfonic acid. In some embodiments, the edisylate salt of Formula IX is characterized by an XRPD pattern substantially in accordance with FIG. 6.

In some embodiments Y is sulfuric acid. In some embodiments, the sulfate salt of Formula IX is characterized by an XRPD pattern substantially in accordance with FIG. 19.

In some embodiments Y is oxalic acid. In some embodiments, the oxalate salt of Formula IX is characterized by an XRPD pattern substantially in accordance with FIG. 21.

Figure 25:
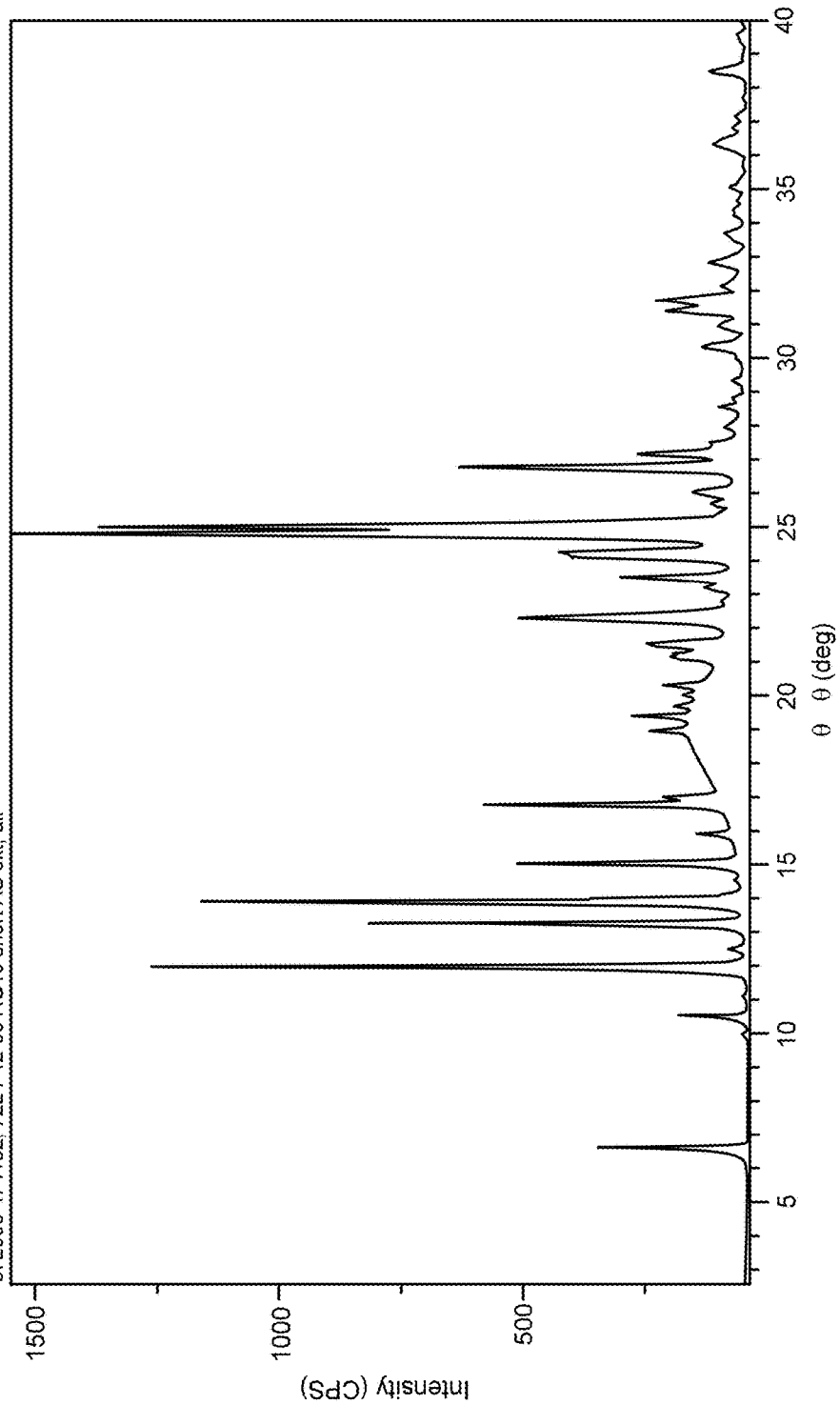
FIG. 25 shows an X-ray powder diffraction (XRPD) pattern of form b of the maleate salt of Formula IX.

In some embodiments Y is maleic acid. In some embodiments, the maleate salt of Formula IX is characterized by an XRPD pattern substantially in accordance with FIG. 23. In some embodiments, the maleate salt of Formula IX is characterized by an XRPD pattern substantially in accordance with FIG. 25.

In some embodiments Y is acetic acid. In some embodiments, the acetic acid salt of Formula IX is characterized by an XRPD pattern substantially in accordance with FIG. 27.

In some embodiments Y is L-malic acid. In some embodiments, the L-malic acid salt of Formula IX is characterized by an XRPD pattern substantially in accordance with FIG. 29.

The molar ratios of AG-10 and Y in Formula Ib can vary depending on the multiprotic acid used. For example, when Y is maleic acid, the molar ratio of AG-10 to Y is 1:1; when Y is edisylate, the molar ratio of AG-10 to Y is 2:1; and when Y is malic acid, the molar ratio of AG-10 to Y is 1.8:1.

Pharmaceutically acceptable salts of Formula I can be produced using a number of conventional means in the art. For example, the free acid form of a compound of Formula I may be contacted with a stoichiometric amount of the appropriate acid in water, an organic solvent, or a mixture of the two. In some embodiments, pharmaceutically acceptable salts of Formula I are made in nonaqueous media such as an ether, ethyl acetate, ethanol, isopropanol, or acetonitrile. In some embodiments, the pharmaceutically acceptable salts of Formula I are made by dissolving a compound of Formula IX in water, adding a suitable amount of HX to form a mixture, and adding a nonaqueous solvent, such as the nonaqueous media described above to crystallize the salt. In some embodiments, a suitable amount of HX is a stoichiometric amount. It is understood the HX comprises a hydrogen and an X is a pharmaceutically acceptable anion of a protic acid as defined above.

As with pharmaceutically acceptable salts of Formula I, pharmaceutically acceptable salts of Formula Ib can also be produced using a number of conventional means in the art. As a non-limiting example, the free acid form of a compound of Formula Ib may be contacted with a stoichiometric or sub-stoichiometric amount of the appropriate multiprotic acid in water, an organic solvent, or a mixture of the two to produce a pharmaceutically acceptable salt of Formula Ib.

C. Crystalline Forms of Formula IX

In a further aspect, provided herein are crystalline forms of Formula IX

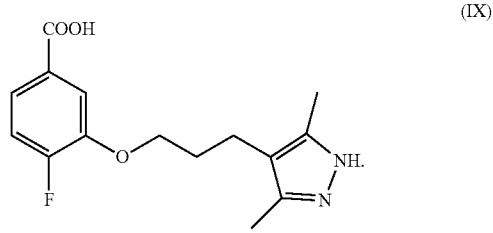 [SMILES: Cc1n[nH]c(C)c1CCCOc1cc(C(=O)O)ccc1F]

(IX)

The current disclosure describes eleven crystalline forms of Formula IX, six HCl salt forms (Type A, Type B, Type E, Type H, Type I, and Type J), three free base forms (Type K, Type C and Type G), and two unidentified forms (Type D and Type F). A summary of the properties of the identified forms are provided in Table 1 and Table 2.

In some embodiments, the crystalline forms of Formula IX provided herein are substantially free of other crystalline forms. The term "substantially free" refers to an amount of 10% or less of another form, preferably 8%, 5%, 4%, 3%, 2%, 1%, 0.5%, or less of another form.

TABLE 1

Characterization results of HCl salt crystal forms

| Crystal Form Batch No. | Weight Loss % | Endotherm (peak, °C.) | HPLC Purity (area %) | Stoichiometry (acid:FB)* | Speculated Form |
|---|---|---|---|---|---|
| Type A | 1.3 | 111.7, 212.6, 237.3 | 98.76 | 0.91 | |
| Type B | 1.2 | 161.4, 232.2, 262.3 | 97.86 | 0.86 | Anhydrate |
| Type E | 1.5 | 182.0, 242.7 | 98.60 | 0.91 | |
| Type I | 3.0 | 62.0, 158.4, 215.7 | 97.94 | 0.86 | Hydrate |
| Type H | 4.6 | 90.4, 200.5, 232.3 | 98.47 | 0.91 | MeOH solvate |
| Type J | 21.5 | 120.8, 197.8, 221.5 | 91.69 | 0.90 | DMAc solvate |

*the Stoichiometry was determined by HPLC/IC using freebase Type A (TRM-01658-2) as the standard sample. A routine method was used and no systemic development and validation was conducted.

TABLE 2

Characterization results of freebase forms

| Crystal Form Batch No. | Weight Loss % | Endotherm (peak, °C.) | HPLC Purity (area %) | Cl⁻ Content (%)* |
|---|---|---|---|---|
| Type K (monohydrate) | 6.1 | 159.3, 176.2, 278.4 | 99.12 | — |
| Type C | 3.1 | 91.2, 173.0 | — | 0.17 |
| Type G | 3.7 | 231.1 | 99.46 | 0.14 |

—: no data available.
*the theoretical Cl⁻ content of mono-HCl salt is 10.8%. Based on the results of Cl⁻ content, Type C and G were determined to be freebase forms.

In some embodiments, provided herein is crystalline Type A of Formula IX. In some embodiments, crystalline Type A of Formula IX is characterized by an X-ray powder diffraction pattern comprising peaks at 7.0, 10.4, 12.0, 13.0, and 13.9 degrees 2θ (±0.2 degrees 2θ). In some embodiments, crystalline Type A of Formula IX is characterized by an X-ray powder diffraction pattern comprising peaks at 12.0, 21.8, 25.9, 26.7, and 27.9 degrees 2θ (±0.2 degrees 2θ). In some embodiments, the X-ray powder diffraction pattern further comprises one or more peaks at 7.0, 10.3, 13.9, 15.6, and/or 17. In some embodiments, crystalline Type A of Formula IX characterized by an X-ray powder diffraction pattern substantially in accordance with FIG. 31. In some embodiments crystalline Type A of Formula IX is substantially free of other crystalline forms.

In some embodiments, crystalline Type A of Formula IX is characterized by a weight loss ranging from about 0.7% to about 1.9% upon heating to around 150° C., as measured by thermal gravimetric analysis. In some embodiments, the weight loss is about 1.3% as measured by thermal gravimetric analysis.

Figure 37:
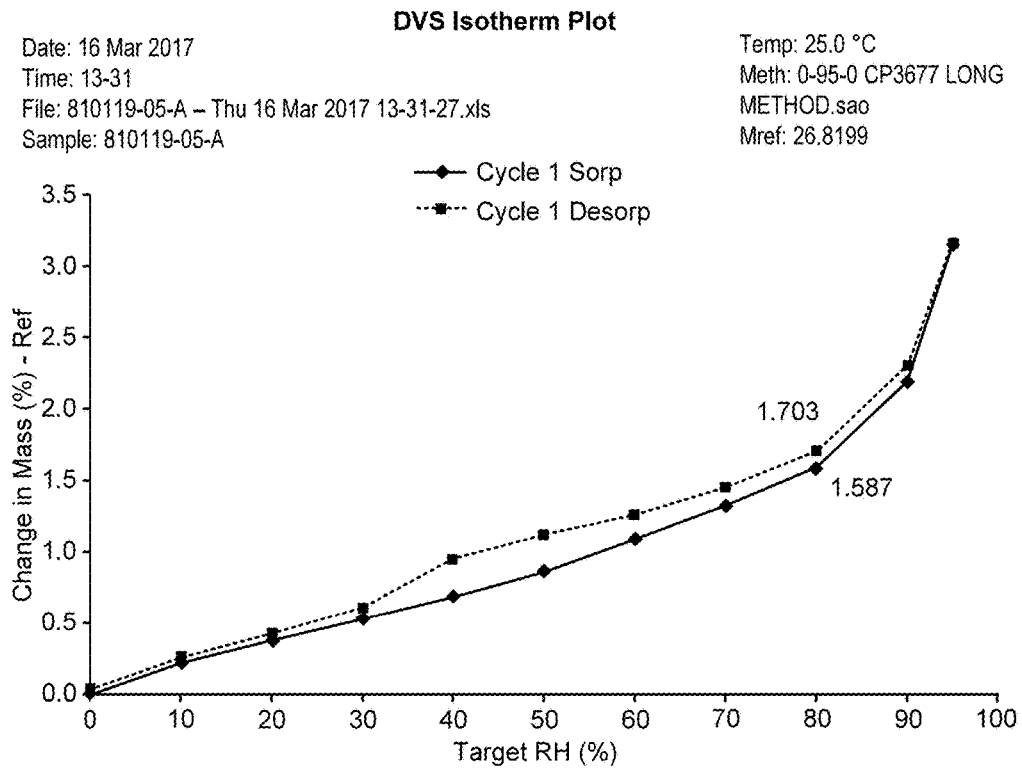
FIG. 37 shows dynamic vapor sorption (DVS) data of crystalline Type A of Formula IX.

In some embodiments, Crystalline Type A of Formula IX is characterized by water uptake of about 1.6% at 25° C./80% relative humidity (RH) after undergoing a dynamic vapor sorption cycle which includes pre-equilibration at 0% RH. In some embodiments, crystalline Type A of Formula IX characterized by gains of less than 2.5% weight after undergoing a dynamic vapor sorption cycle from about 0% relative humidity (RH) to about 90% RH. In some embodiments, crystalline Type A of Formula IX has a dynamic vapor sorption profile substantially as shown in FIG. 37.

In some embodiments, crystalline Type A of Formula IX is characterized by a differential scanning calormnetry thermogram comprising endothermic peaks at around 211-214 and 237-239° C. In some embodiments, the differential scanning calorimetry thermogram comprises endothermic peaks around 11.7, 212.6, and 237.3° C.

In some embodiments, provided herein is crystalline Type B of Formula IX. In some embodiments, crystalline Type B of Formula IX is characterized by an X-ray powder diffraction pattern comprising peaks at 12.0, 13.8, 17.2, 17.7, and 19.8 degrees 2θ (±0.2 degrees 2θ). In some embodiments, crystalline Type B of Formula IX characterized by an X-ray powder diffraction pattern comprising peaks at 12.1, 13.9, 19.8, 23.3, and 24.4 degrees 2θ (±0.2 degrees 2θ). In some embodiments, crystalline Type B of Formula IX characterized by an X-ray powder diffraction pattern substantially in accordance with FIG. 40. In some embodiments crystalline Type B of Formula IX is substantially free of other crystalline forms.

In some embodiments, crystalline Type B of Formula IX is characterized by a weight loss from about 0.6% to about 2.0% upon heating to around 150° C., as measured by thermal gravimetric analysis. In some embodiments, crystalline Type B of Formula IX is characterized by a weight loss of about 1.2% upon heating to around 150° C., as measured by thermal gravimetric analysis.

In some embodiments, crystalline Type B of Formula IX is characterized by a differential scanning calorimetry thermogram comprising endothermic peaks at around 161.4, 232.2 and 262.3° C.

In some embodiments, provided herein is crystalline Type E of Formula IX. In some embodiments, crystalline Type E of Formula IX is characterized by an X-ray powder diffraction pattern comprising peaks at 11.8, 14.0, 15.1, 19.9, and 24.0 degrees 2θ (±0.2 degrees 2θ). In some embodiments, crystalline Type E of Formula IX characterized by an X-ray powder diffraction pattern comprising peaks at 11.9, 14.0, 15.1, and 25.8 degrees 2θ (±0.2 degrees 2θ). In some embodiments, crystalline Type E of Formula IX characterized by an X-ray powder diffraction pattern substantially in accordance with FIG. 46. In some embodiments crystalline Type E of Formula IX is substantially free of other crystalline forms.

In some embodiments, crystalline Type E of Formula IX is characterized by a weight loss from about 0.5% to about 2.5% upon heating to around 150° C., as measured by thermal gravimetric analysis. In some embodiments, crystalline Type E of Formula IX is characterized by a weight loss of about 1.5% upon heating to around 150° C., as measured by thermal gravimetric analysis.

In some embodiments, crystalline Type E of Formula IX is characterized by a differential scanning calorimetry thermogram comprising endothermic peaks at around 182.0 and 242.7° C.

In some embodiments, provided herein is crystalline Type I of Formula IX. In some embodiments, crystalline Type I of Formula IX is characterized by an X-ray powder diffraction pattern comprising peaks at 11.4, 12.1, 12.4, 13.6, and 13.9 degrees 2θ (±0.2 degrees 2θ). In some embodiments, crystalline Type I of Formula IX characterized by an X-ray powder diffraction pattern comprising peaks at 12.5, 17.3, 23.4, 25.0, and 25.4 degrees 2θ (±0.2 degrees 2θ). In some embodiments, crystalline Type I of Formula IX characterized by an X-ray powder diffraction pattern substantially in accordance with FIG. 55. In some embodiments crystalline Type I of Formula IX is substantially free of other crystalline forms.

In some embodiments, crystalline Type I of Formula IX is characterized by a weight loss ranging from about 2.5% to 3.5% upon heating to around 120° C., as measured by thermal gravimetric analysis. In some embodiments, crystalline Type I of Formula IX is characterized by a weight loss of about 3.0% upon heating to around 120° C., as measured by thermal gravimetric analysis.

In some embodiments, crystalline Type I of Formula IX is characterized by a differential scanning calorimetry thermogram comprising endothermic peaks at around 62.0 and 158.4, 215.7° C.

In some embodiments, provided herein is crystalline Type H of Formula IX. In some embodiments, crystalline Type H of Formula IX is characterized by an X-ray powder diffraction pattern comprising peaks at 11.8, 12.3, 13.8, 15.7, and 16.9 degrees 2θ (±0.2 degrees 2θ). In some embodiments, Crystalline Type H of Formula IX characterized by an X-ray powder diffraction pattern comprising peaks at 11.9, 12.3, 21.7, 23.3, and 25.8 degrees 2θ (±0.2 degrees 2θ). In some embodiments, crystalline Type H of Formula IX characterized by an X-ray powder diffraction pattern substantially in accordance with FIG. 51. In some embodiments crystalline Type H of Formula IX is substantially free of other crystalline forms.

In some embodiments, Crystalline Type H of Formula IX is characterized by a weight loss ranging from about 3.5% to about 5.5% upon heating to around 150° C., as measured by thermal gravimetric analysis. In some embodiments, crystalline Type H of Formula IX is characterized by a weight loss of about 4.6% upon heating to around 150° C., as measured by thermal gravimetric analysis.

In some embodiments, crystalline Type H of Formula IX is characterized by a differential scanning calorimetry thermogram comprising endothermic peaks at around 90.4 and 200.5, 232.3° C.

In some embodiments, provided herein is crystalline Type J of Formula IX. In some embodiments, crystalline Type J of Formula IX is characterized by an X-ray powder diffraction pattern comprising peaks at 4.6, 11.8, 12.8, 13.8, and 14.6 degrees 2θ (±0.2 degrees 2θ). In some embodiments, Crystalline Type J of Formula IX characterized by an X-ray powder diffraction pattern comprising peaks at 13.8, 14.7, 22.9, 26.2, and 27.7 degrees 2θ (±0.2 degrees 2θ). In some embodiments, crystalline Type J of Formula IX characterized by an X-ray powder diffraction pattern substantially in accordance with FIG. 59. In some embodiments crystalline Type J of Formula IX is substantially free of other crystalline forms.

In some embodiments, crystalline Type J of Formula IX is characterized by a weight loss ranging from about 17.5% to about 24% upon heating to around 120° C., as measured by thermal gravimetric analysis. In some embodiments, crystalline Type J of Formula IX is characterized by a weight loss of about 21.5% upon heating to around 120° C., as measured by thermal gravimetric analysis.

In some embodiments, crystalline Type J of Formula IX is characterized by a differential scanning calorimetry thermogram comprising endothermic peaks at around 120.8 and 197.8, 221.5° C.

In some embodiments, provided herein is crystalline Type K of Formula IX. In some embodiments, crystalline Type K of Formula IX is characterized by an X-ray powder diffraction pattern comprising peaks at 7.5 9.8, 13.9, 15.9, and 19.3 degrees 2θ (±0.2 degrees 2θ). In some embodiments, crystalline Type K of Formula IX characterized by an X-ray powder diffraction pattern comprising peaks at 7.2, 7.6, 9.9, 14.0, and 19.3 degrees 2θ (±0.2 degrees 2θ). In some embodiments, crystalline Type K of Formula IX characterized by an X-ray powder diffraction pattern substantially in accordance with FIG. 59. In some embodiments crystalline Type K of Formula IX is substantially free of other crystalline forms.

In some embodiments, crystalline Type K of Formula IX is characterized by a weight loss ranging from about 5.0% to about 7.0% upon heating to around 120° C., as measured by thermal gravimetric analysis. In some embodiments, crystalline Type K of Formula IX is characterized by a weight loss of about 6.1% upon heating to around 120° C., as measured by thermal gravimetric analysis.

In some embodiments, crystalline Type K of Formula IX is characterized by a differential scanning calorimetry thermogram comprising endothermic peaks at around 159.3 and 176.2, 278.4° C.

In some embodiments, provided herein is crystalline Type C of Formula IX. In some embodiments, crystalline Type C of Formula IX is characterized by an X-ray powder diffraction pattern comprising peaks at 9.5, 11.7, 12.3, 13.4, and 14.6 degrees 2θ (±0.2 degrees 2θ). In some embodiments, Crystalline Type C of Formula IX characterized by an X-ray powder diffraction pattern comprising peaks at 14.6, 16.8, 19.5, 20.7, and 22.5 degrees 2θ (±0.2 degrees 2θ). In some embodiments, crystalline Type C of Formula IX characterized by an X-ray powder diffraction pattern substantially in accordance with FIG. 43. In some embodiments crystalline Type C of Formula IX is substantially free of other crystalline forms.

In some embodiments, crystalline Type C of Formula IX is characterized by a weight loss ranging from about 2.0% to about 4.0% upon heating to around 150° C., as measured by thermal gravimetric analysis. In some embodiments, crystalline Type C of Formula IX is characterized by a weight loss of about 3.1% upon heating to around 150° C., as measured by thermal gravimetric analysis.

In some embodiments, crystalline Type C of Formula IX is characterized by a differential scanning calorimetry thermogram comprising endothermic peaks at around 91.2 and 173.0° C.

In some embodiments, provided herein is crystalline Type G of Formula IX. In some embodiments, crystalline Type G of Formula IX is characterized by an X-ray powder diffraction pattern comprising peaks at 9.8, 12.2, 13.1, 13.4, and 14.6 degrees 2θ(±0.2 degrees 2θ). In some embodiments, crystalline Type G of Formula IX characterized by an X-ray powder diffraction pattern comprising peaks at 12.3, 13.2, 13.4, 17.8, and 26.6 degrees 2θ (±0.2 degrees 2θ). In some embodiments, crystalline Type G of Formula IX characterized by an X-ray powder diffraction pattern substantially in accordance with FIG. 43. In some embodiments crystalline Type G of Formula IX is substantially free of other crystalline forms.

In some embodiments, crystalline Type G of Formula IX is characterized by a weight loss a ranging from about 1.7% to about 2.7% upon heating to around 200° C., as measured by thermal gravimetric analysis. In some embodiments, crystalline Type G of Formula IX is characterized by a weight loss about 3.7% upon heating to around 200° C., as measured by thermal gravimetric analysis.

In some embodiments, crystalline Type G of Formula IX is characterized by a differential scanning calorimetry thermogram comprising endothermic peaks at around 231.1° C.

In some embodiments, provided herein is crystalline Type D of Formula IX. In some embodiments, crystalline Type D of Formula IX characterized by an X-ray powder diffraction pattern substantially in accordance with FIG. 45 (upper plot). In some embodiments crystalline Type D of Formula IX is substantially free of other crystalline forms.

In some embodiments, herein is crystalline Type F of Formula IX. In some embodiments, crystalline Type F of Formula IX characterized by an X-ray powder diffraction pattern substantially in accordance with FIG. 45 (lower plot). In some embodiments crystalline Type F of Formula IX is substantially free of other crystalline forms.

Methods of making the described crystalline types are further detailed in the Examples of this application. Crystallization conditions used for making types Types A-K include anti-solvent addition, slow evaporation, slow cooling, slurry conversion at room temperature (RT), slurry conversion at 50° C., solid vapor diffusion, liquid vapor diffusion.

IV. Examples

Example 1

Preparation of 3-(3-Hydroxy-propyl)-pentane-2, 4-dione (a Compound of Formula IV)

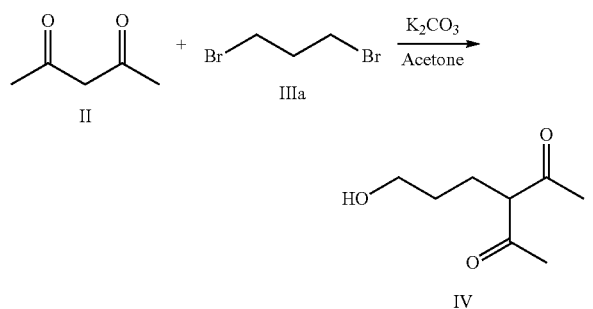

A compound of Formula IIIa (100 g, 495 mmol 1.0 equiv.) was dissolved in acetone (1 L). A compound of Formula II (49.59 g, 495 mmol, 1.0 equiv.) was added to above solution, followed by addition of $K_2CO_3$ (82.14 g, 594.38 mmol, 1.2 equiv.) and KI (41.11 g, 247 mmol, 0.5 equiv.) at room temperature with stirring. The reaction mixture was heated to 60±5° C. and stirred for 40 h at this temperature. The reaction mixture was filtered and then concentrated under reduced pressure to afford a compound of Formula IV (102 g) as viscous orange liquid.

Example 2

Preparation of 3(3, 5-Dimethyl-1H-pyrazol-4-yl)propane-1-ol (a compound of Formula V)

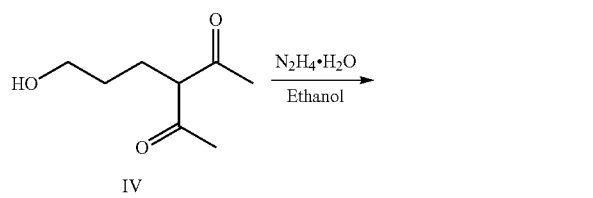

A compound of Formula IV (100 g, 632 mmol, 1.0 equiv.) was dissolved in ethanol (1 L). Hydrazine hydrate (87 g, 1738 mmol, 2.75 equiv.) and conc. HCl (4.6 mL, 0.2 equiv.) were added to above solution at room temperature. The reaction mixture was heated to 75±5° C. and stirred for 3 h at this temperature. After completion of reaction by TLC (70% ethyl acetate: n-hexane, visible in iodine) and observation of product peak in mass spectrum, the reaction mixture was concentrated under reduce pressure to afford a compound of Formula V (70 g) as a colorless liquid syrup which was used as such for next step.

Example 3

Preparation of 4-(3-Bromo-propyl)-3, 5-dimethyl-1H-pyrazole (a compound of formula VIa)

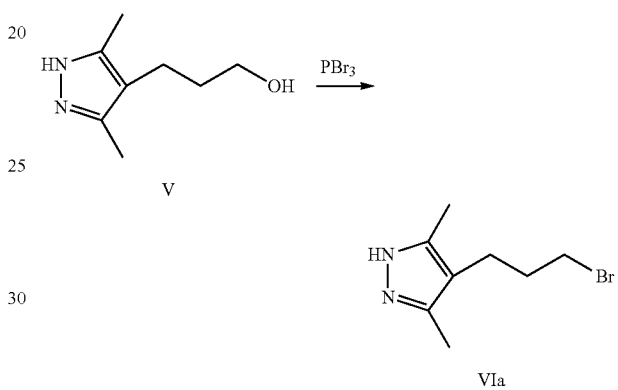

A compound of Formula V (35 g, 227 mmol, 1.0 equiv.) was dissolved in 1,2-dichloroethane (525 mL). $PBr_3$ (64.67mL, 681 mmol, 3 equiv.) was added in small portions at room temperature over 30 minutes. The reaction mixture was heated up to 75±5° C. and stirred for 3 h at this temperature. After completion of reaction by TLC (50% ethyl acetate: n-hexane, visible in iodine) and observation of product peak in Mass spectrum, the reaction mixture was diluted with dichloromethane (350 mL) and quenched with saturated solution of $NaHCO_3$ till pH=7 to 8. Both organic and aqueous layers were separated and collected. The organic layer was dried over $MgSO_4$ and filtered. Filtrate was concentrated under reduce pressure to afford a compound of Formula VIa (38 g) as a viscous orange liquid.

Example 4

Preparation of 3-[3-(3, 5-Dimethyl-1H-pyrazol-4-yl)-propoxy]-4-fluoro-benzoic acid methyl ester (a compound of Formula VIIIa)

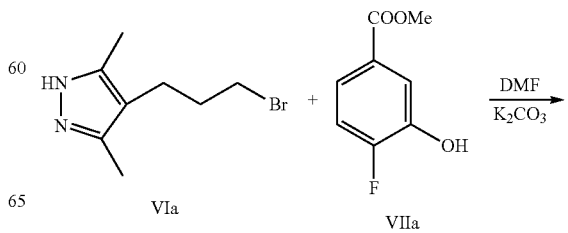

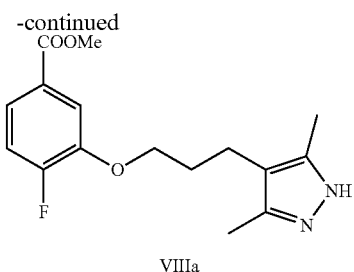

VIIIa

A compound of Formula VIIa (19 g, 111 mmol, 1.0 equiv.) was dissolved in DMF (190 mL). A compound of Formula VIa (31.5 g, 145.14 mmol, 1.3 equiv.) was added followed by K$_2$CO$_3$ (38.6 g, 279.18 mmol, 2.5 equiv.) at room temperature under stirred conditions. The reaction mixture was stirred for 16 to 18 h at room temperature. After completion of reaction in TLC (50% ethyl acetate: n-hexane), the reaction mixture was diluted with water (190 mL) and ethyl acetate (95 mL). Both organic layer and aqueous layer were separated and collected. Aqueous layer was extracted with ethyl acetate (190 mL). The combined organic extract was washed with water (95 mL), brine (95 mL), dried over Na$_2$SO$_4$ and filtered. The filtered organic layer was concentrated under reduce pressure to afford a crude viscous orange liquid (40 g). The crude was further purified by column chromatography using silica gel (285 g) and eluted with varying quantity of ethyl acetate in hexane to afford pure product, a compound of Formula VIIIa (25 g) as an off white solid.

Example 5

Preparation of 3-[3-(3,5-Dimethyl-1H-pyrazol-4-yl)-propoxy]-4-fluoro-benzoic acid methyl ester (a compound of Formula VIIIa)

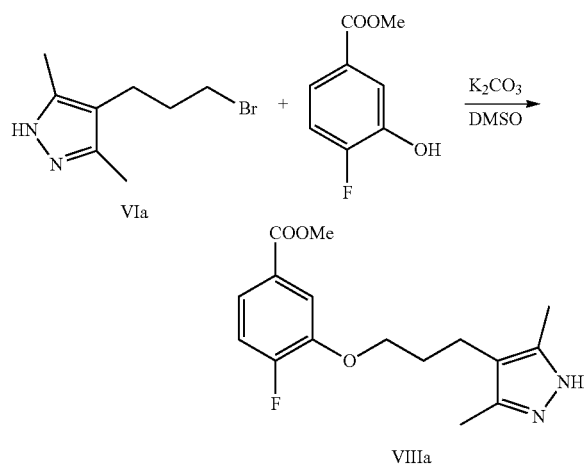

4-(3-Bromopropyl)-3,5-dimethyl-1H-pyrazole hydrobromide (VIa) and DMSO were charged into vessel and agitated at 20±10° C. for 10 minutes. The mixture was then heated to 55±5° C. with stirring. To this mixture was transferred a stirred solution containing 4-fluoro-3-hydroxy-benzoic acid methyl ester (VIIa), potassium carbonate and anhydrous DMSO. The DMSO solution of the alkyl bromide were slowly transferred in order to maintaining an internal temperature of 55.0±5° C. Addition was complete after 6 hours and the mixture was agitated at 55±5° C. for an additional hour at 55.0±5° C. The mixture was cooled to 25±5° C. over the course of 30 minutes and water added while maintaining a temperature below 25° C. The mixture was extracted with ethyl acetate and the aqueous layer back extracted with ethyl acetate. The pooled ethyl acetate solutions were washed brine. The combined ethyl acetate washes were concentrated under vacuum to a minimal volume and heptane was added, which precipitates VIIIa. The mixture was heated to 75±5° C. and aged with stirring for 1 hour. The mixture was cooled to 25±5° C. over the course of two hours and the resulting solids collected by filtration. The filter cake was washed with ethyl acetate in heptane (30%). Isolated solids were dried with a nitrogen flow. Solids are charged to vessel and combined with ethyl acetate and heptane. The resulting mixture is heated to 75±5° C. to dissolve solids. The solution was cooled to 25±5° C. over the course of two hours and the resulting solids collected by filtration. The solids were washed with a 30% ethyl acetate/heptane solvent mixture and dried in vacuum oven at 55° C. to give VIIIa in >99.5% purity.

Example 6

Preparation of 3-[3-(3, 5-Dimethyl-1H-pyrazol-4-yl)-propoxy]-4-fluoro-benzoic acid (a compound of Formula IX)

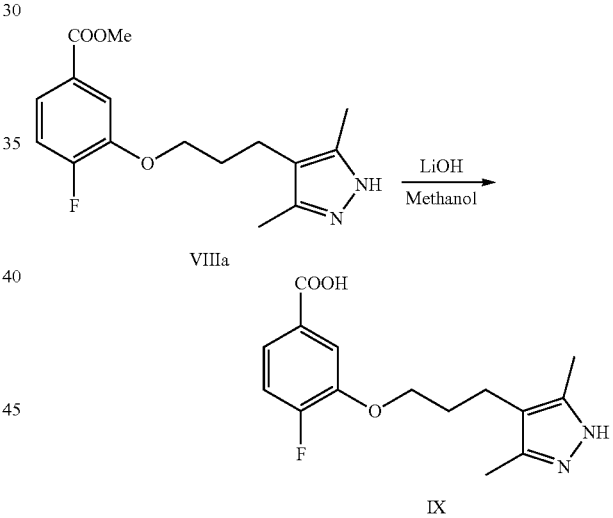

A compound of Formula VIIIa (19 g, 62 mmol, 1 equiv.) was dissolved in methanol (95 mL, 5 vol.) at room temperature. A solution of LiOH.H$_2$O (6.5 g, 155 mmol, 2.5 equiv.) in water (57 mL) was added in small portions at room temperature over 10 to 15 minutes. The reaction mixture was stirred for 2 h at room temperature. After completion of reaction by TLC (70% ethyl acetate: n-hexane), the reaction mixture is concentrated below 45° C. under reduced pressure to afford a solid residue of Formula IX.

Example 7

Preparation of a Pharmaceutically Acceptable Salt of Formula I

The solid residue of Formula IX was dissolved in water (57 mL) and stirred for 10 min and cooled to 0±5° C. The aqueous solution was acidified with conc. HCl (20-25 mL) to pH=2 and stirred for 30 minutes at 0±5° C. Precipitation was observed which was filtered and dried at room temperature to afford pure product, a compound of Formula Ia (17.5 g) as an off-white solid.

Example 8

Additional Preparation of a Pharmaceutically Acceptable Salt of Formula I

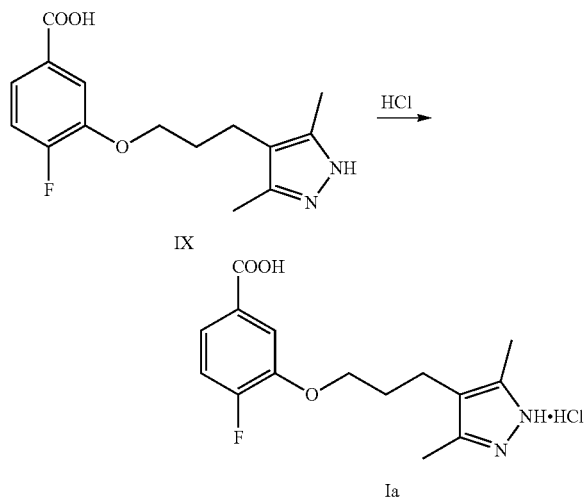

Water and concentrated HCl were charged to a vessel and cooled with stirring to 10±5° C. Compound of Formula IX and water were charged to a second vessel and cooled with stirring to 10±5° C. The HCl solution in vessel 1 was transferred to a vessel containing compound of Formula IX mixture over not less than 15 minutes, while maintaining a temperature of <25° C. The resulting slurry was aged with stirring at 20±5° C. for 44 hours. The solids were collected by filtration, washed with 0.2 N HCl (3 ×) and dried under vacuum at ≥55° C. to provide Ia as white solid, >99.8% purity.

Example 9

Preparation of 3-[3-(3,5-dimethyl-1H-pyrazol-4-yl) propoxy]-4-fluorobenzoic acid hydrochloride salt (Compound Ia) from VIIIa

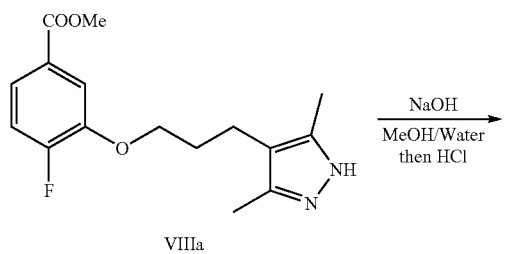

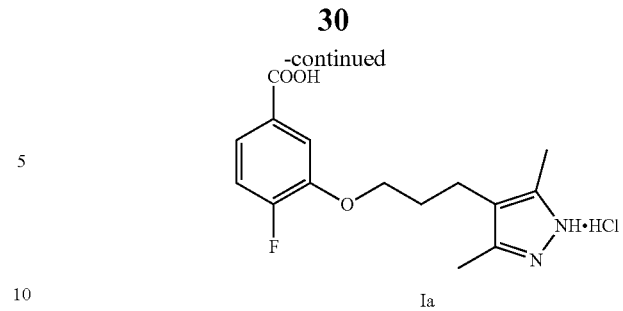

A jacketed glass vessel is charged with compound of formula VIIIa (1.0 equiv.) and methanol. The mixture is cooled with stirring to 10±5° C. and over the course of 20 minutes an aqueous solution of sodium hydroxide (3 equiv.) is charged. The mixture is aged with stirring at 20±5° C. for NLT 2 hours at which point the reaction is complete. Stirring is stopped and water is added. Methanol is then removed by vacuum distillation at an internal temperature of NMT 35° C. The resulting concentrated, clear aqueous solution is cooled to 10° C. and concentrated HCl is added until the pH was lowered to between 1.4-1.6 (pH meter) to precipitate the HCl salt. The solids are collected by filtration, washed with 0.2 N HCl and dried under vacuum at 50° C. to give a compound of Formula Ia in NLT 99.5% purity.

Example 10

Preparation of 3-[3-(3,5-dimethyl-1H-pyrazol-4-yl) propoxy]-4-fluorobenzoic acid (compound of formula IX) from VIIIa

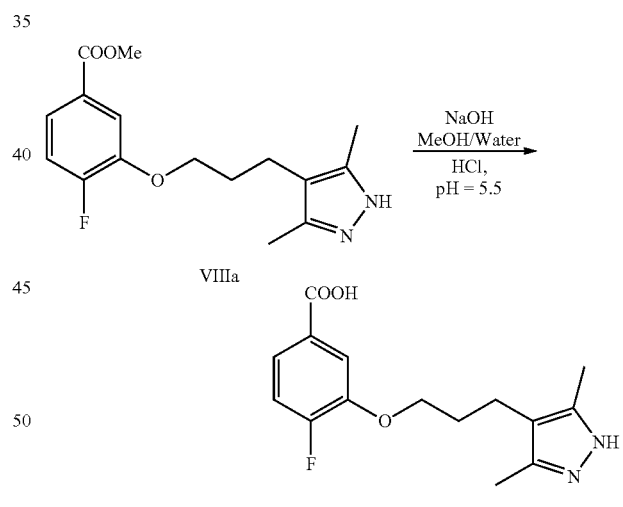

Methyl 3-(3-(3,5-dimethyl-1H-pyrazol-4-yl)propoxy)-4-fluorobenzoate (Compound of formula VIIIa) and methanol were charged into a vessel and the resulting mixture was agitated at 20±5° C. until dissolved. The solution was cooled to 10±5° C. and over the course of 20 minutes a sodium hydroxide solution was added while maintaining a temperature ≤25° C. The mixture temperature was adjusted to 25±5° C. and aged with stirring for 18 hours. The reaction mixture was filtered. Water was added to filtrate and the resulting mixture concentrated under vacuum until volume of the mixture was reduced to minimal volume. Water was again added and the resulting mixture concentrated under vacuum until volume of the mixture was reduced to minimal volume. The pH of the aqueous mixture was adjusted to 5.5±0.5 by addition of concentrated hydrochloric acid then 0.5N HCl. The temperature of the mixture was adjusted to 7±5° C. and aged with stirring for an additional hour. The solids were collected by filtration, washed with water and partially dried under vacuum at ≥55° C. to provide compound of Formula IX as white solids with >99.5% HPLC purity.

Example 11

Conversion of the Hydrochloride Salt to Free Base

3-[3-(3,5-Dimethyl-1H-pyrazol-4-yl)-propoxy]-4-fluorobenzoic acid hydrochloride (10.0 g, 30.4 mmol, 1.0 equiv.) was taken in deionized water (30.0 mL) at room temperature and was cooled to 10±5° C. To this mixture was added saturated sodium bicarbonate to pH≅6-7 and stirred for 30 minute at this temperature. The off white precipitate obtained was filtered and washed with deionized water (20 mL). Solid compound was dried at room temperature to afford 3-[3-(3,5-dimethyl-1H-pyrazol-4-yl)-propoxy]-4-fluorobenzoic acid (the compound of Formula IX) (7.40 g, 83.2%) as an off-white solid.

Example 12

Oral Dosing Using Pharmaceutical Acceptable Salt of Formula I

The following examples describes pharmacokinetic measurements of the compound of Formula IX in various salt and zwitterionic forms. The results shown herein show that compounds of Formula I possess an unexpectedly high pharmacokinetic profile.

Rats or Dogs were orally dosed with the zwitterion, Na salt, or HCl salt for of AG-10. The form of AG-10 used and dosing amount are as indicated in Table 3. Plasma samples from each rat/dog, as applicable, were measured between 0 and up to 96 hours after dosing with the specified form of AG-10. After isolation from the animal, each sample (50μL) was protein precipitated by adding 500 μL 0.1% formamide in acetonitrile to the sample. After addition for the formamide solution, the sample was vortexed and centrifuging at 1400 rpm for 15 min at 4° C. 100 μL of the supernatant was removed and diluted with 100 μL water. 5 μL of the diluted sample was injected for LC-MS/MS analysis. Pharmacokinetic data was calculated with the reported $C_{max}$ and exposure (0-24h, ng·h/mL) shown in Table 3.

TABLE 3

Oral Dosing of a pharmaceutically acceptable salt of Formula I in multiple species

| | Species | Form | Dose (mg/kg) | Cmax (ng/mL) (μM) | Exposure (0-24 h) ng · h/mL |
|---|---|---|---|---|---|
| 1 | Rat | Zwitterion | 200 | 26,373 (90.3 μM) | — |
| 2 | Rat | Na salt | 50 mg/kg daily for 28 days | 12,322 (42.2 μM) | — |
| 3 | Rat | HCl salt | 200 | 216,333 (741 μM) | 395,503 |
| 4 | Dog | Zwitterion | 25 | 17,533 (60 μM) | 89,786 |
| 5 | Dog | HCl salt | 20 | 16,075 (55.1 μM) | 69,088 |
| 6 | Dog | HCl salt | 25 | 25,067 (85.8 μM) | 128,374 |
| 7 | Dog | HCl salt | 60 | 41,800 (143.2 μM) | 155,814 |
| 8 | Dog | HCl salt | 200 | 154,333 (528.5 μM) | 1,020,640 |

As can be seen in Table 3, the HCl salt of Formula I provided a surprising and significant improvement in $C_{max}$ values in dogs and rats as compared to the zwitterion and the Na salt. Compare, row 3 to row 1, and row 6 to row 4. Thus, in order to reach the same levels of bioavailability, a significantly smaller dose of the HCl salt of Formula I is needed.

Example 13

Intravenous Dosing Pharmaceutically Acceptable Salt of Formula I

The following examples describes pharmacokinetic measurements of the compound of Formula IX in various salt and zwitterionic forms when administered intravenously to Rats and Dogs. The results shown herein show that compounds of Formula I possess an unexpectedly high pharmacokinetic profile when administered both orally and intravenously.

Mice, Rats or Dogs were intravenously dosed with the zwitterion, Na salt, or HCl salt for of AG-10. The form of AG-10 and dosing amount are as indicated in Table 4. Plasma samples from each mouse/rat/dog, as applicable, were measured between 0 and 24 hours after dosing with the specified form of AG-10. After isolation from the animal, each sample (50 μL) was protein precipitated by adding 500 μL 0.1% formamide in acetonitrile to the sample. After addition for the formamide solution, the sample was vortexed and centrifuging at 1400 rpm for 15 min at 4° C. 100 μL of the supernatant was removed and diluted with 100 μL water. 5 μL of the diluted samples was injected for LC-MS/MS analysis. Pharmacokinetic data was calculated with the reported $C_{max}$ and exposure (0-24 h, ng·h/mL) shown in Table 4.

TABLE 4

Intravenous Dosing of a pharmaceutically acceptable salt of Formula I in multiple species

| | Species | Form | Dose (mg/kg) | Cmax (ng/mL) (μM) |
|---|---|---|---|---|
| 1 | Mouse | Zwitterion | 3 | 4,485 (15.4 μM) |
| 2 | Rat | Zwitterion | 3.43 | 3,093 (10.6 μM) |
| 3 | Rat | Na salt | 10 | 3,150 (10 μM) |
| 4 | Rat | HCl salt | 1 | 4,275 (14.6 μM)* |
| 5 | Dog | HCl salt | 1 | 5,959 (20.4 μM)* |

*the $C_{max}$ reported is an extrapolated $C_0$

Example 14

High Bioavailability of AG-10 in Multiple Species

Figures 2A, 2B:
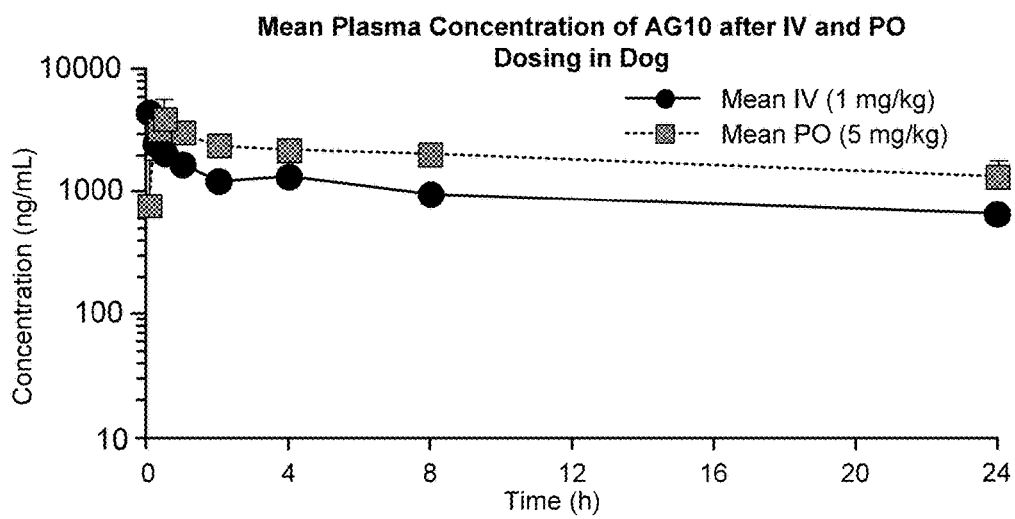
FIG. 2A, FIG. 2B, FIG. 2C, FIG. 2D, FIG. 2E, and FIG. 2F show pharmacokinetic results demonstrating the high bioavailability of AG-10 in multiple species.
Figures 2C, 2D:
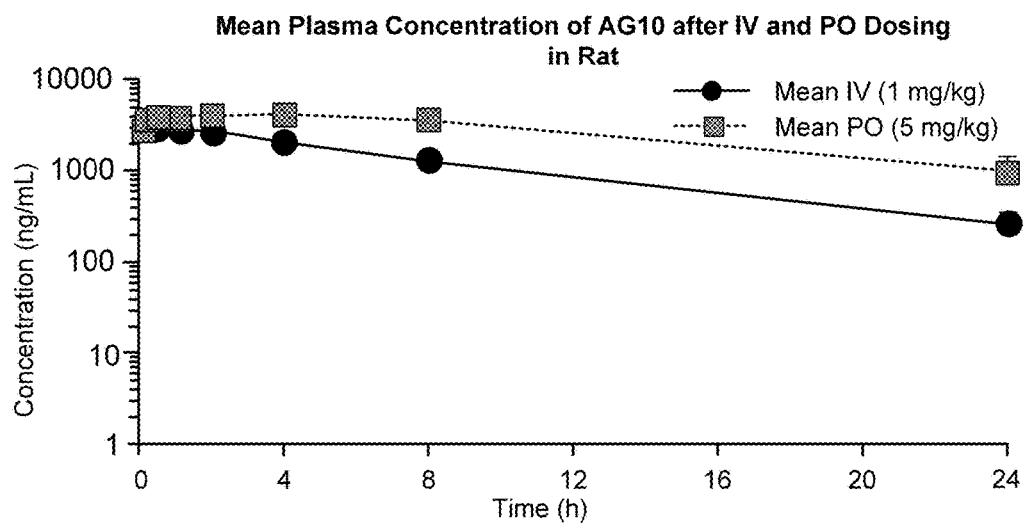
Figures 2E, 2F:
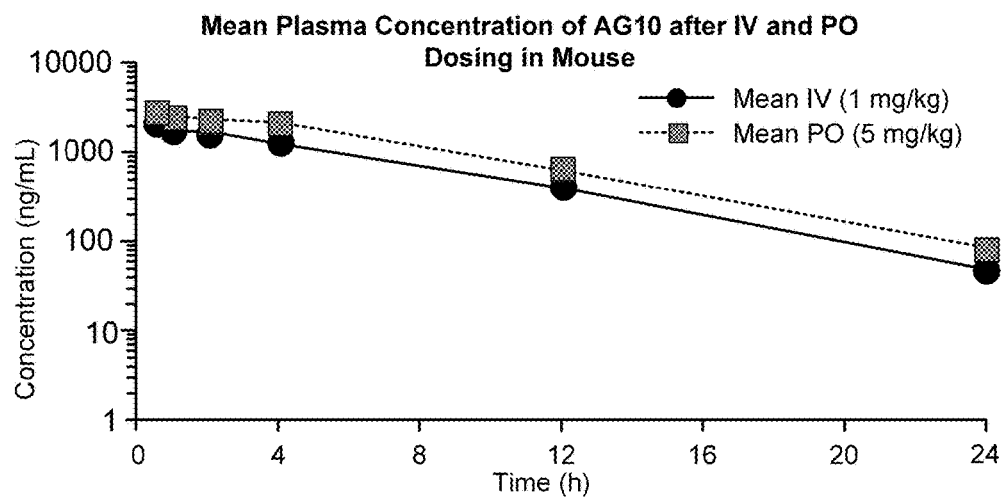

FIG. 2A, FIG. 2B, FIG. 2C, FIG. 2D, FIG. 2E, and FIG. 2F show pharmacokinetic results demonstrating the high bioavailability of AG-10 in dogs, rats, and mice. The mean plasma concentration of AG-10 was measured from 0-24 hours after dosing with 1 mg/kg of AG-10 intravenously and 5 mg/kg of AG-10 orally. The calculated pharmacokinetic data is shown in FIG. 2B, FIG. 2D, and FIG. 2F.

Example 15

High Bioavailability of AG-10 in Dogs

Figures 3A, 3B:
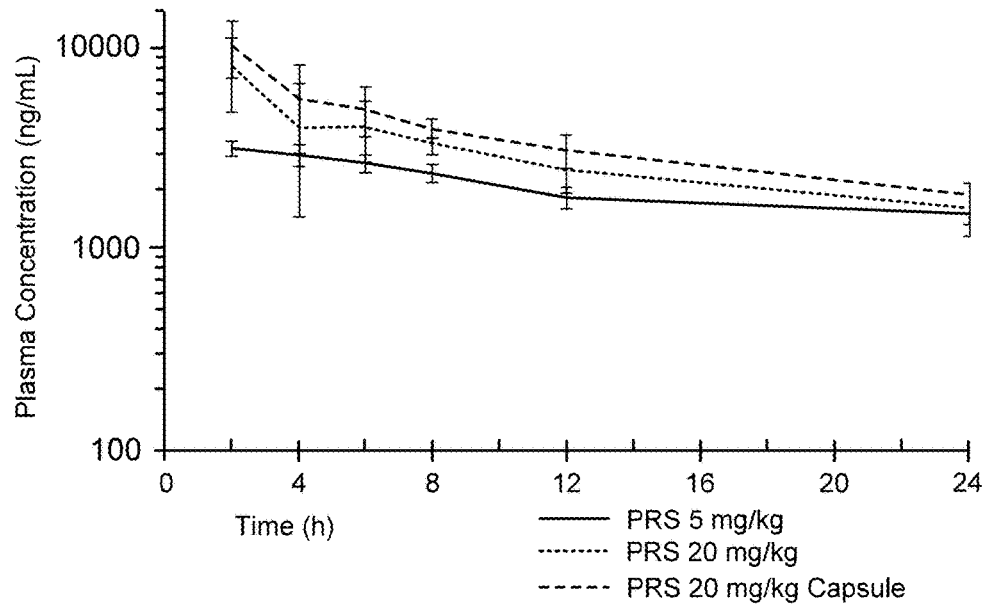
FIG. 3A, FIG. 3B, FIG. 3C, FIG. 3D, FIG. 3E, and FIG. 3F show pharmacokinetic results demonstrating the high bioavailability of AG-10 in male and female dogs at different dosing levels.
Figures 3C, 3D:
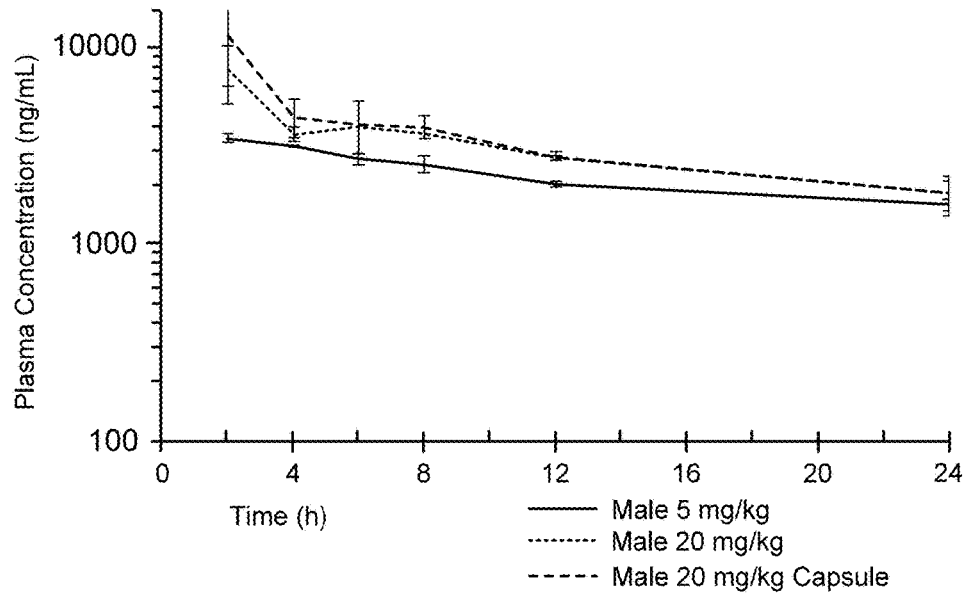
Figures 3E, 3F:
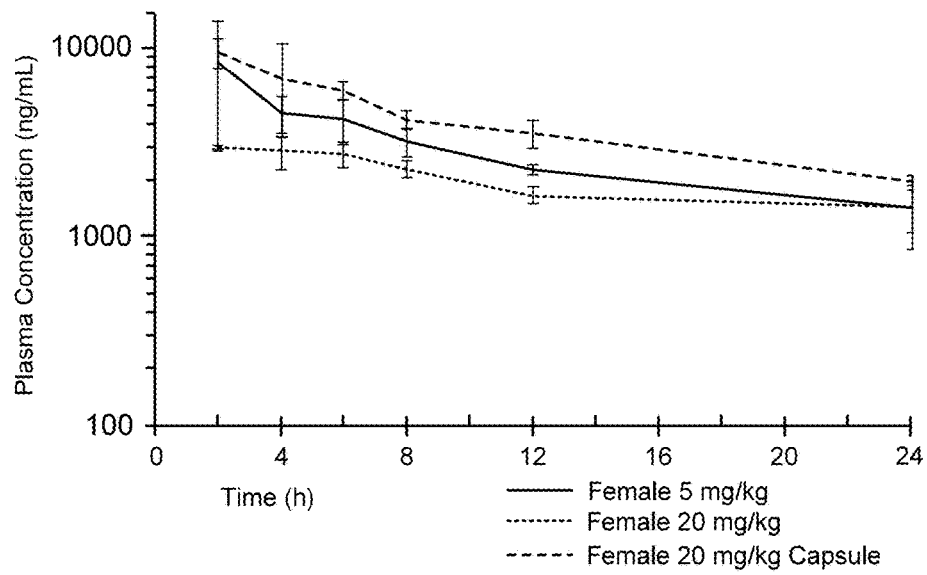

FIG. 3A, FIG. 3B, FIG. 3C, FIG. 3D, FIG. 3E, and FIG. 3F show pharmacokinetic results demonstrating the high bioavailability of AG-10 in male and female dogs at different dosing levels. The mean plasma concentration of AG-10 was measured from 2-24 hours after oral dosing with 5 mg/kg or 20 mg/kg of AG-10. The calculated pharmacokinetic data is shown in FIG. 3B, FIG. 3D, and FIG. 3F.

Example 16

Salt & Cocrystal Screen

Numerous salt and cocrystal conditions were tested targeting various pharmaceutically acceptable salts. Experimental details can be found in Table 5 and Table 6. Experiments were conducted using a variety of crystallization techniques including cooling, evaporation, slurrying, and solvent assisted grinding. Solids resulting from salt and cocrystal screening experiments were observed by polarized light microscopy (PLM) and analyzed by XRPD. XRPD patterns of isolated solids were compared to that of known forms of AG10 and counterion/coformer.

Confirmed salts of AG 10 were identified from experiments targeting salt formation with strong acids specifically methanesulfonic acid, ethane-1,2-disulfonic acid, benzenesulfonic acid, p-toluenesulfonic acid, ethanesulfonic acid, sulfuric acid, hydrogen bromide and nitric acid.

Salts or cocrystals of AG10 were also isolated from experiments targeting salt/cocrystal formation with weaker organic acids such as citric acid, acetic acid, maleic acid, oxalic acid and malic acid.

Experiments were also set up targeting L-tartaric acid, glycolic acid, and fumaric acid; however, experiments conducted aimed at isolating these materials as single crystalline phases were not successful and resulted in starting materials or a physical mixture of unique additional peaks with starting materials.

Attempts to generate salts/cocrystals of AG10 with L-aspartic acid, benzoic acid, gentisic acid, and succinic acid were not successful.

TABLE 5

Preparing Pharmaceutically Acceptable Salts of Formula I and Formula Ib

| Counterion (X:Y)[a] | Conditions[b] | Observations | Results |
|---|---|---|---|
| Benzenesulfonic acid (1:1) | 1. Added 2.0 mL THF to 94.7 mg AG-10 with stirring at 60° C. 2. Hot filtered 3. Added 52.3 mg acid to clear solution, left at ET for ~15 min 4. Cooled to RT then stirred for ~3 d | 1. Hazy solution 2. Clear solution 3. Clear solution 4. Solution with solids remain, solids collected | Fines, B/E (Birefringence and extinction), agglomerates (PLM) Crystalline, AG10 Besylate (XRPD) |
| HBr (1:1) | 1. Added 2.0 mL heated MIBK to 94.2 mg AG-10 with stirring at 60° C. 2. Added 0.4 mL heated DMSO to sample with stirring at 60° C. 3. Added 55 µL HBr to sample with stirring at 60° C. 4. Cooled to RT, then placed in VO at RT for 3 d 5. Added 1.0 mL MEK to sample with sonication and heated to 60° C., cooled × 2 | 1. Solids remain 2. Clear solution 3. Yellow solution and oil formed 4. Oil with solids 5. Solution with solids remain, solids collected | Fines, B/E, agglomerates (PLM) Crystalline, AG10 Bromide (XRPD) |
| Ethanesulfonic acid (1:1) | 1. Added 3.0 mL THF to 110.9 mg AG-10 at 50° C. with stirring 2. Hot filtered 3. Added 31 µL acid to sample with stirring at 50° C. 4. Cooled to RT | 1. Cloudy solution 2. Clear solution 3. Solids precipitated after ~1 min of stirring at ET 4. Solution with solids remain, solids collected | Crystalline, AG10 Esylate (XRPD) |
| 1,2-Ethanedisulfonic acid (1:1) | 1. Added 2.0 mL heated acetone to 101.8 mg AG-10 with stirring at 50° C. 2. Added 0.5 mL heated DMA to sample with stirring 3. Added 70 mg acid to sample with stirring at 50° C. 4. Held at ET for ~10 min, cooled to RT | 1. Solids remain 2. Clear solution 3. Solids precipitated 4. Solution with solids remain, solids collected | Fines, agglomerates (PLM) Crystalline, AG10 Edisylate + ethanedisulfonic acid (XRPD) |
| 1,2-Ethanedisulfonic acid (2:1) | 1. 36.7 mg acid was dissolved in 400 µL acetone at 60° C. 2. 106.5 mg AG-10 was dissolved in 2.0 mL DMA at 60° C. 3. Acid solution was added to AG-10 solution at ET with stirring and then cooled to RT 4. Heated to 60° C., then cooled | 1. Clear solution 2. Clear solution 3. Hazy solution 4. Solution with solids remain, solids collected | Fines, B/E, agglomerates (PLM) Crystalline, AG10 Edisylate (XRPD) |
| Methanesulfonic acid (1:1) | 1. Added 2.0 mL heated MEK to 100.7 mg AG-10 with stirring at 50° C. 2. Added 0.3 mL heated DMF to sample with stirring 3. Added 23 µL acid to sample with stirring at 50° C. 4. Held at ET for ~20 min, cooled | 1. Solids remain 2. Clear solution 3. Solids precipitated 4. Solution with solids remain, solids collected | Fines, agglomerates (PLM) Crystalline, AG10 Mesylate (XRPD) |

TABLE 5-continued

Preparing Pharmaceutically Acceptable Salts of Formula I and Formula Ib

| Counterion (X:Y)[a] | Conditions[b] | Observations | Results |
|---|---|---|---|
| p-toluenesulfonic acid (1:1) | 1. Added 3.5 mL ACN to 112.0 mg AG-10 with stirring at 60° C.<br>2. Added 74.5 mg acid to slurry at ET<br>3. Increased to 70° C. with stirring<br>4. Mixed solids back into solution, cooled to RT | 1. Solids present<br>2. Solution cleared briefly, then precipitation<br>3. Clear solution with solids on sides<br>4. Solution with solids remain, solids collected | Fines, agglomerates (PLM)<br>Crystalline, AG10 Tosylate (XRPD) |
| Nitric acid (1:1) | 1. Added 0.7 mL DMSO to 95.8 mg AG-10 with stirring at RT<br>2. Added 330 µL acid to solution at RT<br>3. Left at RT stirring for 2 d | 1. Clear solution<br>2. Clear solution<br>3. Solution with solids remain, solids collected | Crystalline, AG10 Nitrate Form A (XRPD) |
| Nitric acid (1:1) | 1. Added 3.0 mL THF to 97.2 mg AG-10 with stirring at RT<br>2. Added 330 µL acid to solution at RT<br>3. Left at RT stirring for 2 d<br>4. Placed in VO at RT | 1. Solids remain<br>2. Clear solution<br>3. Clear solution<br>4. Solids remain | Crystalline, AG10 Nitrate Form B (XRPD) |
| Sulfuric acid (1:1) | 1. Added 2.0 mL heated EtOH to 108.5 mg AG-10 with stirring at 60° C.<br>2. Hot filtered<br>3. Added 22 µL acid to sample with sitting at 60° C.<br>4. Cooled to RT and stirred for 2 d<br>5. Placed at 2-8° C. for 5 d<br>6. Evaporation at RT for 11 d<br>7. Evaporation under nitrogen for 2 d | 1. Opaque solution<br>2. Clear solution<br>3. Cloudy solution<br>4. Hazy solution<br>5. Hazy solution remains<br>6. Clear solution<br>7. Solids remain | Fan agglomerates, B/E (PLM)<br>Crystalline, AG10 Sulfate (XRPD) |

[a]X:Y = AG-10:Counterion mole ratio
[b]Temperatures and times are approximate

TABLE 6

Preparing Pharmaceutically Acceptable Salts of Formula I and Formula Ib

| Coformer (X:Y)[a] | Conditions[b] | Observations | Results |
|---|---|---|---|
| Acetic acid (1:2.2) | 1. Added 2.0 mL heated EtOH to 85.0 mg AG-10 with stirring at 70° C.<br>2. Added 37 µL acetic acid to sample with stirring at 70° C.<br>3. Cooled to RT, held overnight, and reheated to 60° C. for ~3 h<br>4. Cooled to RT and stirred for ~2 d | 1. Clear solution<br>2. Solids present<br>3. Clear solution<br>4. Solution with solids remain, solids collected | Fines, B/E, agglomerates (PLM)<br>Crystalline AG10 (Type G [2]) (XRPD) |
| Acetic acid (1:1) | 1. Milled 102.7 mg AG-10 with 40 µL acetic acid | 1. Solids turned into a paste then dried and white solids collected | Crystalline, AG10 Acetic acid Form A (XRPD) |
| Citric acid (excess) | 1. Added 3.0 mL saturated citric acid solution in IPA to 78.3 mg AG-10 with stirring at RT<br>2. Stirred at RT at 1 d<br>3. Placed at 2-8° C. for 1 d<br>4. Evaporated at RT after 10 d<br>5. Returned to evaporate at RT for 7 d and then placed in VO for ~1 d<br>6. Placed to evaporate under nitrogen for 1 d | 1. Solids present<br>2. Clear solution<br>3. Clear solution<br>4. Single crystal collected<br>5. Solids with liquid remain<br>6. Solids remain used for XRPD | AG10 citrate (SCXRD)<br>Citric acid + AG10 citrate (XRPD) |
| Citric acid (1:1) | 1. Added 1.6 mL IPA to 72.9 mg acid at 50° C.<br>2. Added acid solution to 110.1 mg AG-10 with stirring at 50° C. overnight<br>3. Cooled to RT with stirring, left overnight | 1. Clear solution<br>2. Solids remain<br>3. Solution with solids remain, solids collected | Fines, agglomerates, B/E (PLM)<br>Crystalline AG10 (XRPD) |

TABLE 6-continued

Preparing Pharmaceutically Acceptable Salts of Formula I and Formula Ib

| Coformer (X:Y)[a] | Conditions[b] | Observations | Results |
|---|---|---|---|
| L-Malic acid (1:1) | 1. Added 6.0 mL anhy. ACN to 81.1 mg AG-10 with stirring at 50° C. 2. Added 2.0 mL DCM to sample with stirring at 50° C. 3. Hot filtered 4. Added acid to solution with stirring at 50° C. 5. Cooled to RT and left stirring at RT 6. Evaporation at RT 7. Placed in VO at RT | 1. Solids remain 2. Cloudy solution 3. Clear solution 4. Clear solution 5. Clear solution 6. Solution remains 7. Solids with gel remain | Starburst, agglomerates, B/E with gel (PLM) |
| L-Malic acid (excess) | 1. Added 1.0 mL saturated L-malic acid solution in ACN to 89.3 mg AG-10 with stirring at 60° C. 2. Cooled to RT and stirred for ~3 d 3. Placed at 2-8° C. for 3 d | 1. Clear solution 2. Clear solution 3. Thick slurry, solids collected | Fines, B/E, agglomerates (PLM) Crystalline, AG10 L-malic acid (XRPD) |
| Maleic acid (1:2.2) | 1. Dissolved 85.7 mg maleic acid in 1.5 mL Nitromethane with stirring at 70° C. 2. Added acid solution to 87.8 mg AG-10 with stirring at ET 3. Cooled to RT, held overnight, and reheated to 60° C. for ~3 h 4. Cooled to RT and stirred for ~2 d | 1. Clear solution 2. Solids remain 3. Solids remain 4. Solution with solids remain, chalky solids collected | Fines, B/E, agglomerates (PLM) AG10 Maleate Form B + Material A (XRPD) |
| Maleic acid | 1. LIMS 471312 dried at 110° C. for ~7 min 2. Cooled to RT | 1. Solids became gel-like with yellow tint 2. Solids remain | Agglomerates with minor B/E (PLM) Disordered AG10 Maleate Form B + amorphous halo (XRPD) |
| Maleic acid (1:1) | 1. 2.0 mL p-dioxane was added to 49.6 mg acid was and 122.9 mg AG-10 at RT with stirring 2. Slurry was heated to 50° C. and 4.0 mL p-dioxane was added at 50° C. with stirring. 3. Stirred at 50° C. for ~2 d | 1. Solids remain 2. Solids remain 3. Solution with solids remain, solids collected | AG10 Maleate Form B (XRPD) |
| Maleic acid (1:1) | 1. Filtrate of LIMS 474152 suspension was left to evaporate at RT | 1. Solids remain | AG10 Maleate Form B + additional peak 16.4° + amorphous halo (XRPD) |
| Oxalic acid (1:1.1) | 1. Added 4.0 mL anhy Acetone and 1.0 mL DMA to 96.2 mg AG-10 with stirring at 50° C. 2. Hot filtered 3. 34.5 mg acid added to sample at 50° C. 4. Cooled to RT | 1. Cloudy solution 2. Clear solution 3. Clear solution, then precipitation of solids 4. Solution with solids remain, solids collected | Crystalline AG10 Oxalate (XRPD) |

[a]X:Y = AG-10:Counterion mole ratio
[b]Temperatures and times are approximate

Example 17

The Preparation of the Mesylate Salt of Formula IX

The mesylate salt of Formula DC was produced upon the addition of 1 molar equivalent of methanesulfonic acid to an AG-10 MEK:DMF 2:0.3 v/v solution at elevated temperature. The suspension was held at elevated temperature for ~20 minutes, cooled to room temperature and solids isolated.

Figure 4:
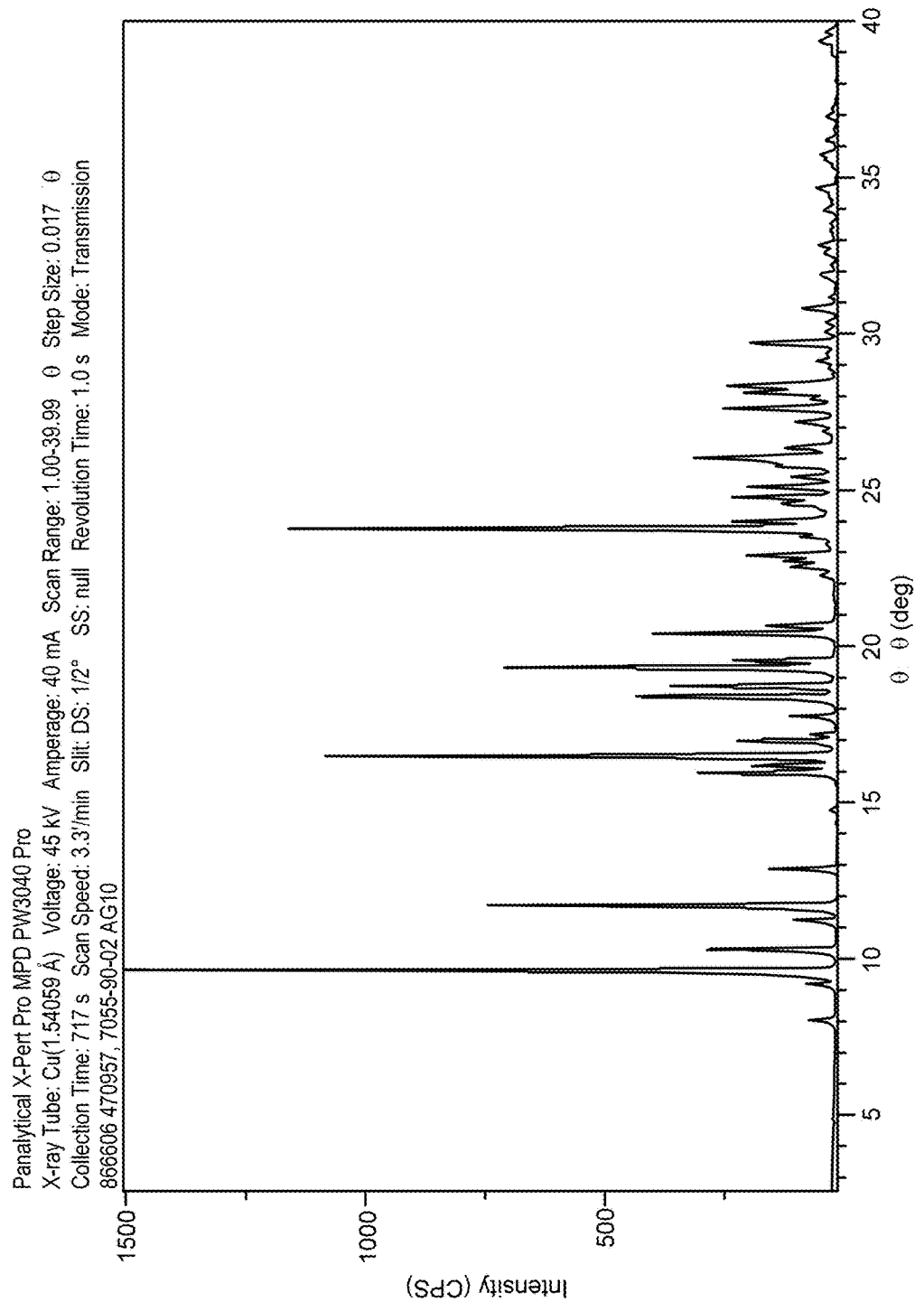
FIG. 4 shows an X-ray powder diffraction (XRPD) pattern of the mesylate salt of Formula IX.

The XRPD pattern is shown in FIG. 4 and exhibits resolution of peaks indicative of crystalline material. Indexing of the XRPD pattern was attempted; however, an indexing solution was not found, possibly due to the sample containing a mixture of crystalline phases or low peak resolution.

The $^1$H NMR spectrum was consistent with AG-10 mesylate salt in a 1:1 mole ratio based on the peak at 2.37 ppm. Trace amounts of DMF and additional unknown peaks were also observed in the spectrum.

Figure 5:
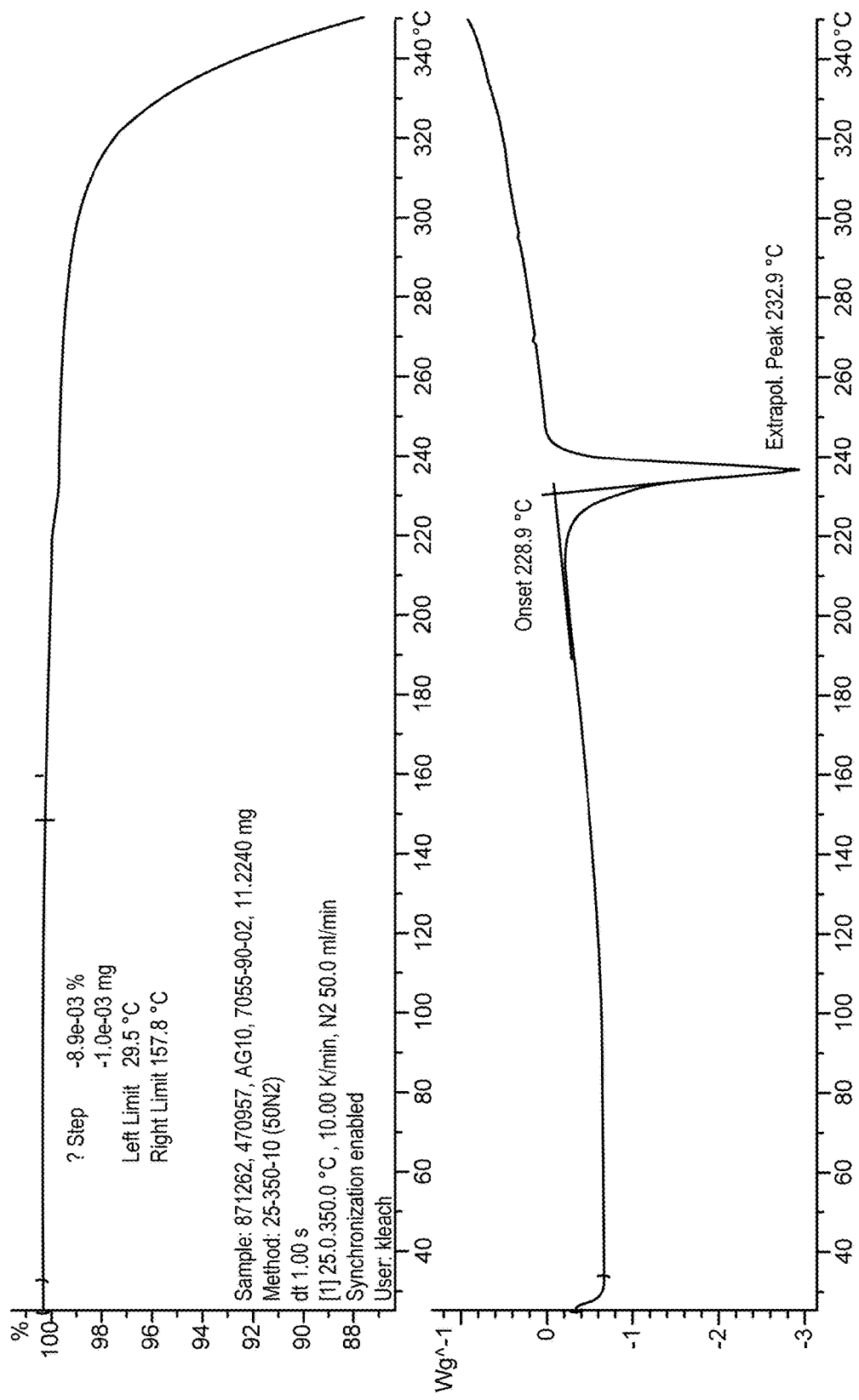
FIG. 5 shows thermo-gravimetric analysis (TGA) and differential scanning calorimetry (DSC) plots of the mesylate salt of Formula IX.

The DSC thermogram (FIG. 5) shows a single endotherm at approx. 233° C. (peak max) likely attributable to melting. No significant weight loss is observed in the TGA (FIG. 5) up to ~200° C. suggesting the material is likely unsolvated/anhydrous.

Example 18

The Preparation of the Edisylate Salt of Formula IX

The edisylate salt of Formula IX was produced upon the addition of 1 molar equivalent of 1,2-ethanedisulfonic acid to an AG10 acetone:DMA solution at elevated temperature. The suspension was cooled to ambient temperature and solids isolated.

Figure 6:
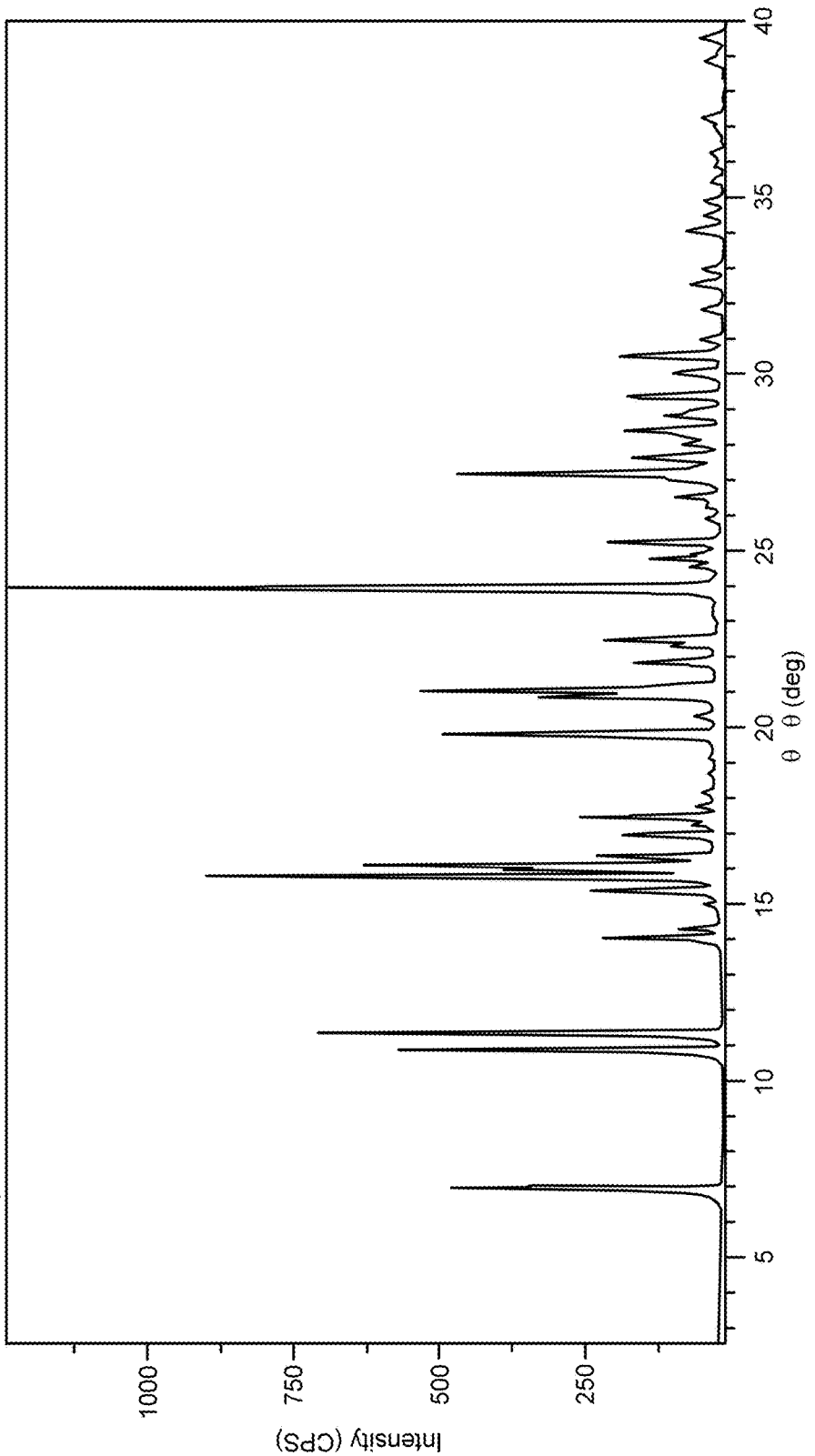
FIG. 6 shows an X-ray powder diffraction (XRPD) pattern of the edisylate salt of Formula IX.

By XRPD, the edisylate salt of Formula IX is composed of a crystalline material (FIG. 6). The ¹H NMR spectrum is consistent with AG-10 edisylate in a 2:1 mole ratio based on the peak at 2.7 ppm. Approximately one mole of DMA was also observed suggesting an AG-10 edisylate DMA (2:1:1) solvate.

Figure 7:
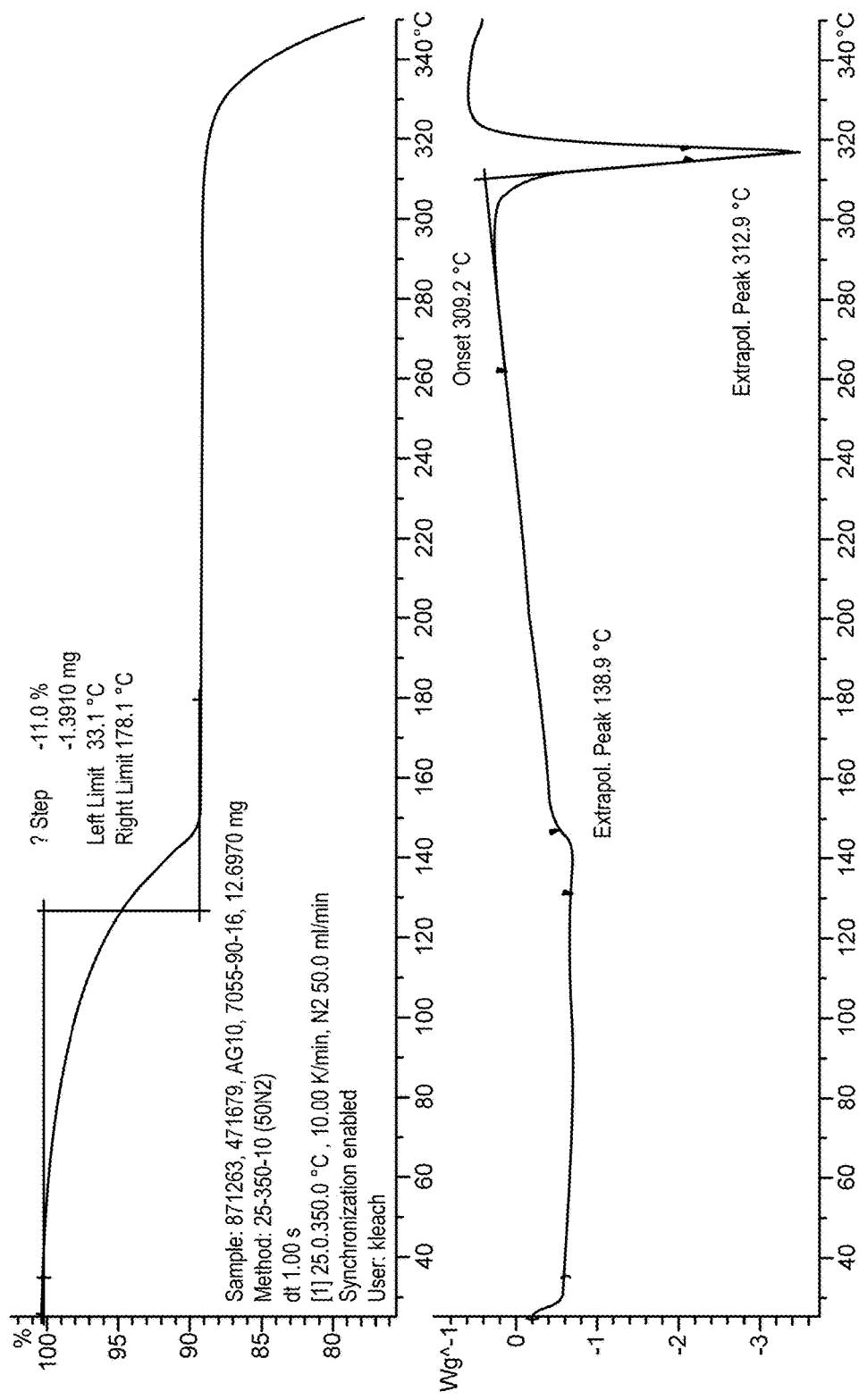
FIG. 7 shows thermo-gravimetric analysis (TGA) and differential scanning calorimetry (DSC) plots of the edisylate salt of Formula IX.

The DSC thermogram (FIG. 7) shows a broad feature at ~139° C. associated with a weight loss of 11% based on TGA (FIG. 7) data that is likely due to desolvation. A sharper endotherm at 313° C. (peak max) likely attributable to melt/decomposition of the desolvated material is observed. Hot stage microscopy is suggested to further understand the behavior of the material with heating.

A sample of the edisylate salt of Formula IX was dried at 180° C. for 10 minutes and no change in physical form resulted based on XRPD.

Example 19

The Preparation of the Besylate Salt of Formula IX

The besylate salt of Formula IX was prepared from cooling a THF solution containing equimolar equivalents of AG-10 and benzenesulfonic acid.

Figure 8:
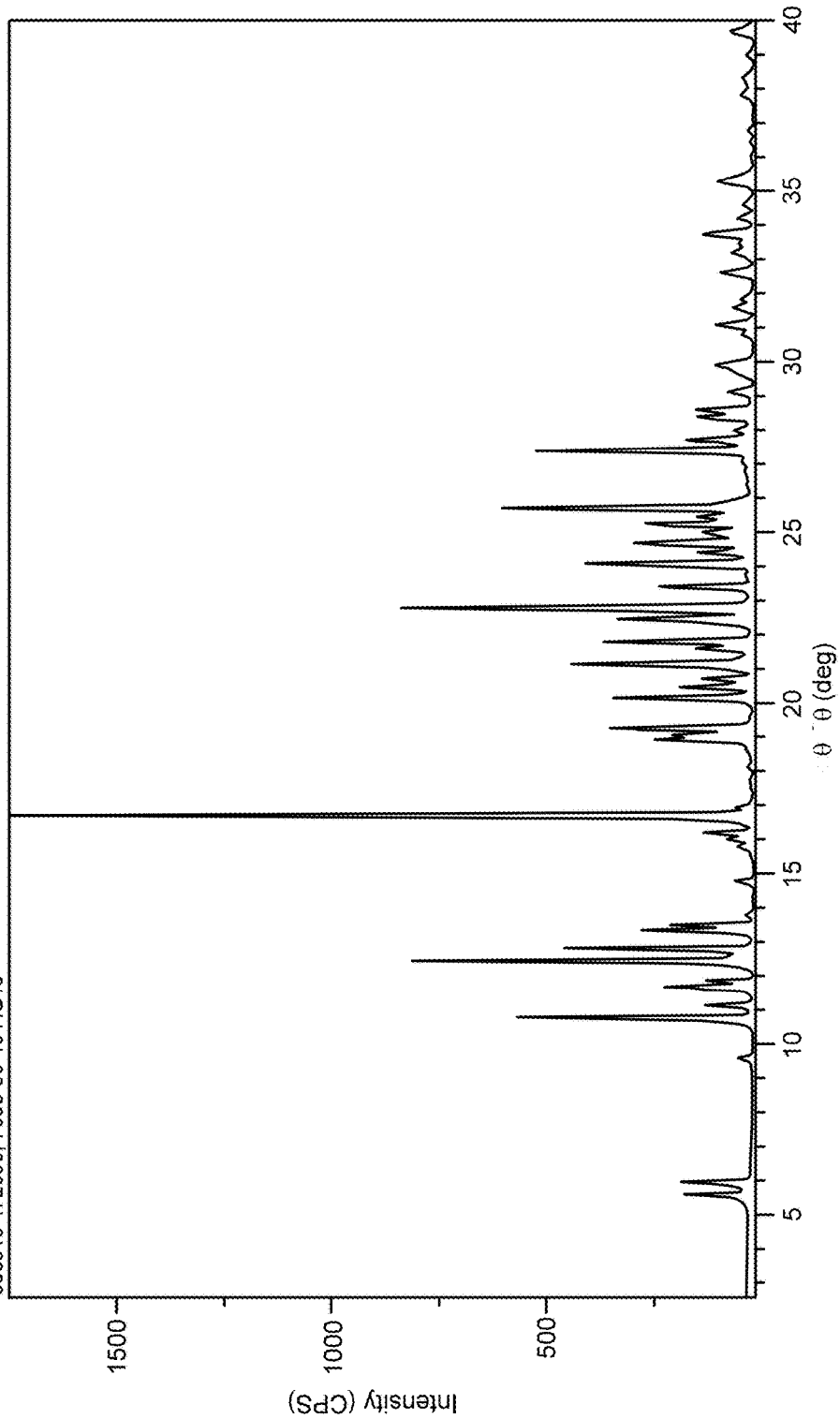
FIG. 8 shows an X-ray powder diffraction (XRPD) pattern of the besylate salt of Formula IX.

The besylate salt of Formula IX is composed of a crystalline material and the XRPD pattern in shown in FIG. 8. The ¹H NMR spectrum is generally consistent with AG10 besylate salt in an approximate 1:1 ratio. Trace amounts of THF was also observed in the spectrum based on the peak at 3.6 ppm.

Figure 9:
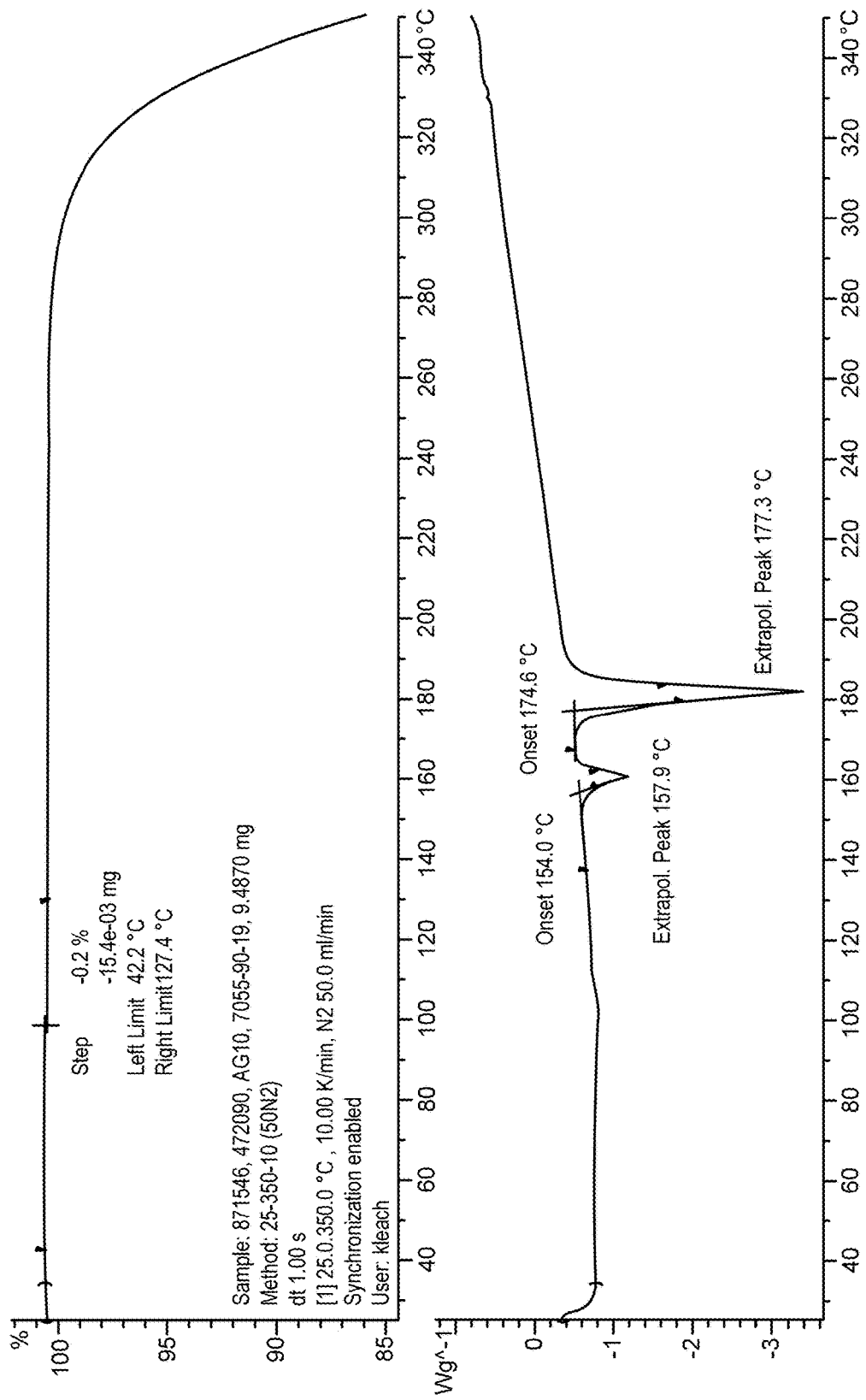
FIG. 9 shows thermo-gravimetric analysis (TGA) and differential scanning calorimetry (DSC) plots of the besylate salt of Formula IX.

Two endothermy are observed in the DSC thermogram with peak max at ~158° C. and 177° C. (FIG. 9). A weight loss of 0.2% is observed between 42° C. and 127° C. (FIG. 9).

Example 20

The Preparation of the Tosylate Salt of Formula IX

The tosylate salt of Formula IX was produced upon the addition of 1 molar equivalent of p-toluenesulfonic acid to an AG-10 acetonitrile solution at elevated temperature.

Figure 10:
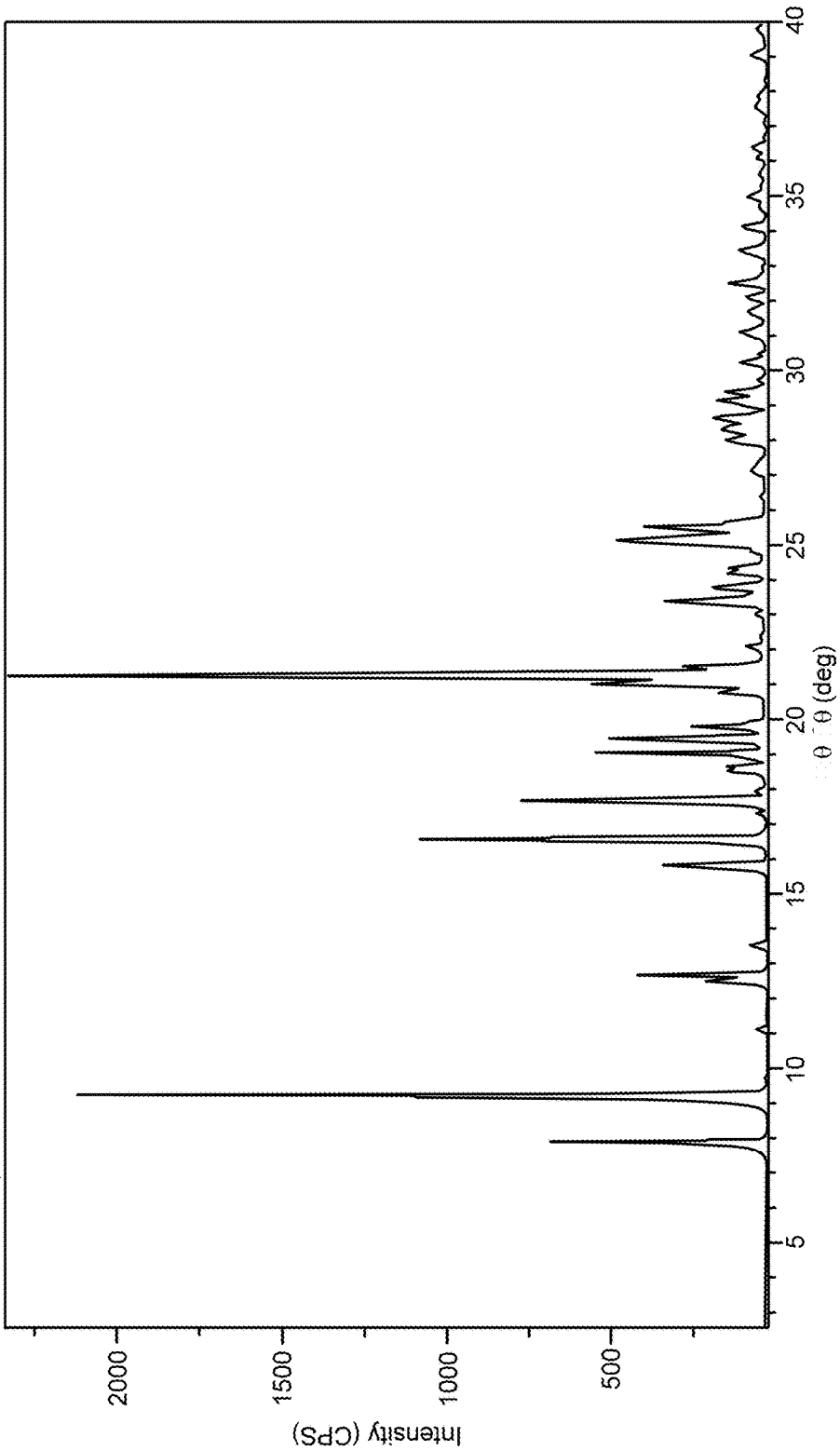
FIG. 10 shows an X-ray powder diffraction (XRPD) pattern of the tosylate salt of Formula IX.

By XRPD, the tosylate salt of Formula IX is composed of a crystalline material (FIG. 10). The pattern was successfully indexed indicating it is composed primarily or exclusively of a single crystalline phase. The unit cell volume obtained from the indexing solution is consistent with AG10 tosylate 1:1 salt based on considerations of molecular volume.

The ¹H NMR spectrum is overall consistent with an AG10 tosylate salt in an approximate 1:1 mole ratio based on the peak at 2.28 ppm.

Figure 11:
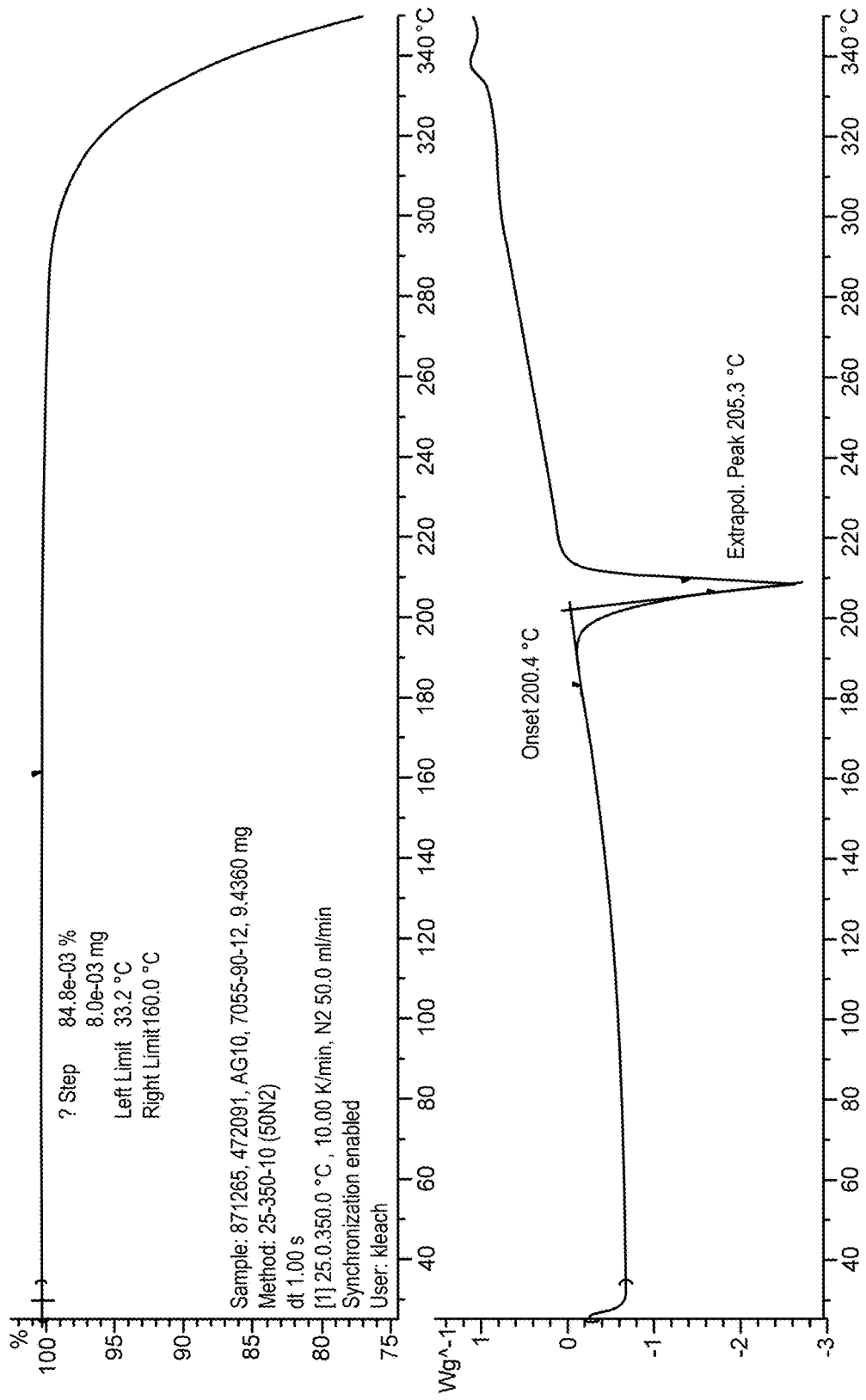
FIG. 11 shows thermo-gravimetric analysis (TGA) and differential scanning calorimetry (DSC) plots of the tosylate salt of Formula IX.

The DSC thermogram shows a single endotherm at approx. 205° C. (peak max) likely attributable to melting (FIG. 11). No significant weight loss is observed in the TGA up to ~160° C. suggesting the material is likely unsolvated/anhydrous (FIG. 11).

Example 21

The Preparation of the Esylate Salt of Formula IX

The esylate salt of Formula IX precipitated from a THF solution containing AG-10 and ethanesulfonic acid (1:1 mole ratio) at 50° C. The suspension was cooled and solids isolated.

Figure 12:
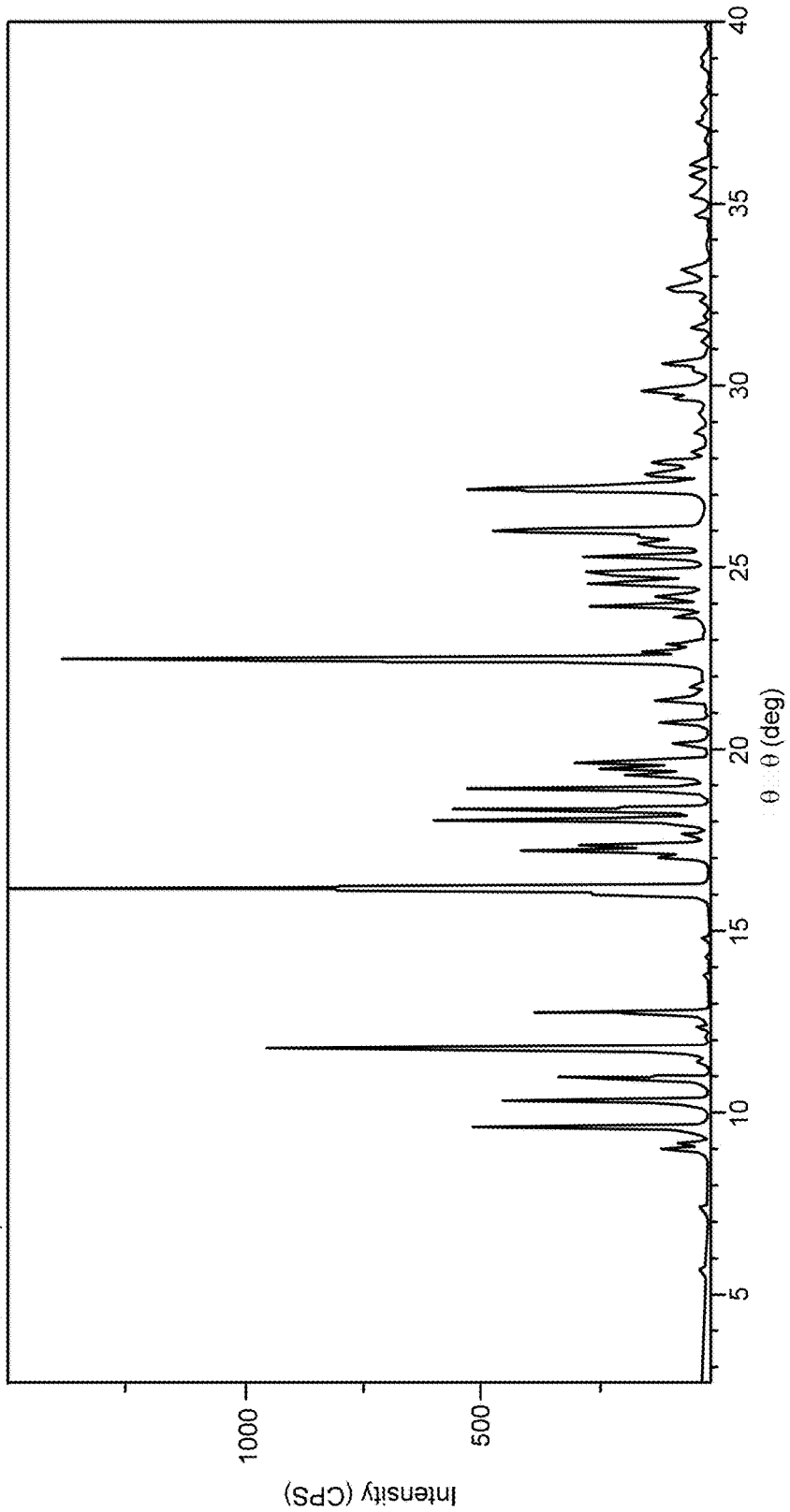
FIG. 12 shows an X-ray powder diffraction (XRPD) pattern of the esylate salt of Formula IX.

The esylate salt of Formula IX is composed of a crystalline materials as confirmed by XRPD (FIG. 12). The ¹H NMR spectrum is consistent with an AG10 esylate salt in a 1:1 mole ratio based on the peak at 2.4 ppm. THF, approximately 0.1 mole was observed in the spectrum.

Figure 13:
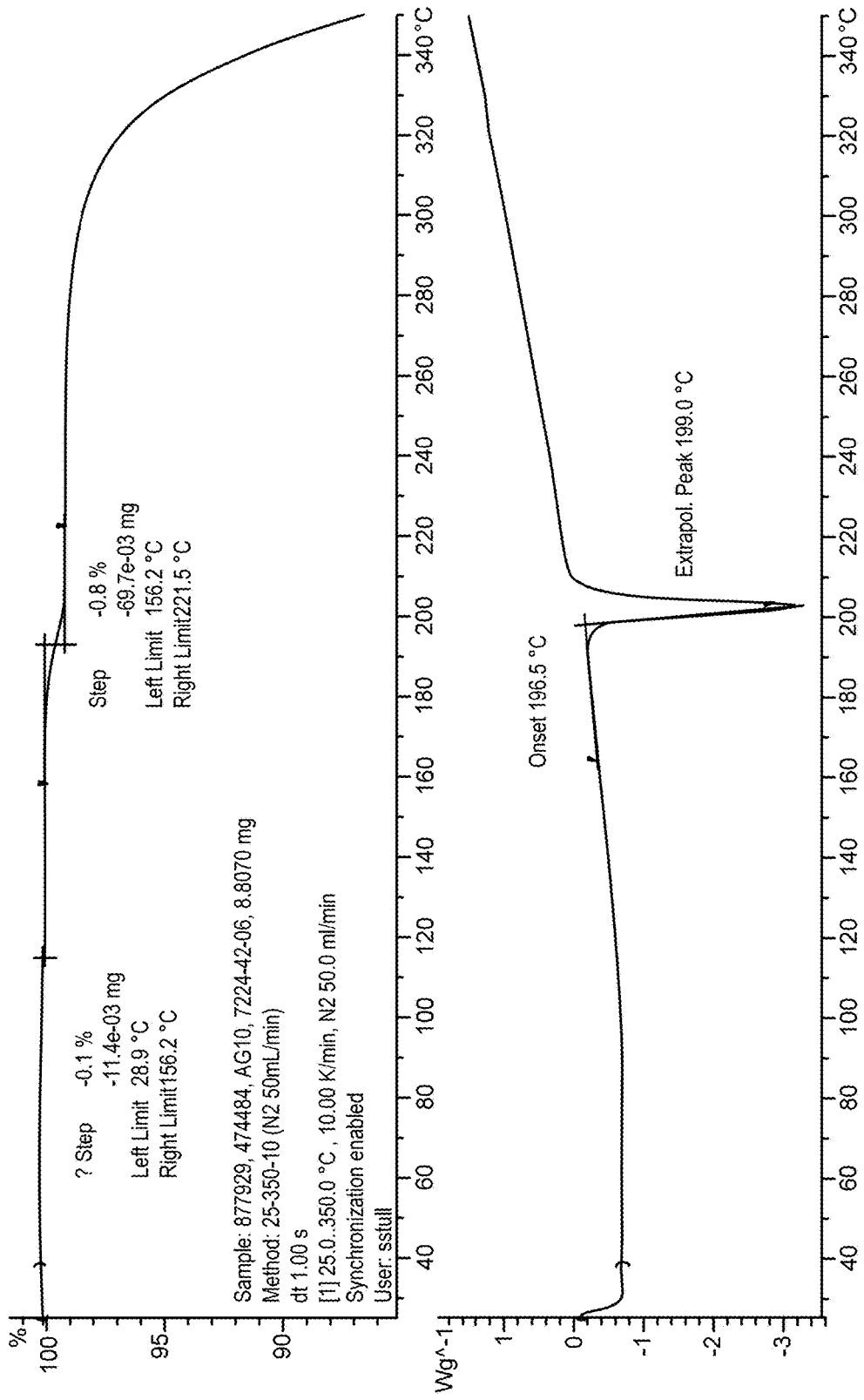
FIG. 13 shows thermo-gravimetric analysis (TGA) and differential scanning calorimetry (DSC) plots of the esylate salt of Formula IX.

A single endotherm at 199° C. (peak max) is observed in the DSC thermogram likely due to melting (FIG. 13). No significant weight loss upon heating up to the melt which may suggest the material is unsolvated or anhydrous (FIG. 13).

Example 22

The Preparation of the Bromide Salt of Formula IX

The bromide salt of Formula IX was prepared via the addition of an equimolar amount of hydrogen bromide to a MIBK:DMSO 2:0.4 v/v solution of AG-10 at ~60° C. This produced a yellow solution and oil formed. The sample was placed in a vacuum oven at room temperature for 3 days and resulted in oil with solids present. MEK was added to the sample with sonication, and heated to 60° C. then cooled, twice. Solids remaining in the resulting suspension were isolated and analyzed.

Figure 14:
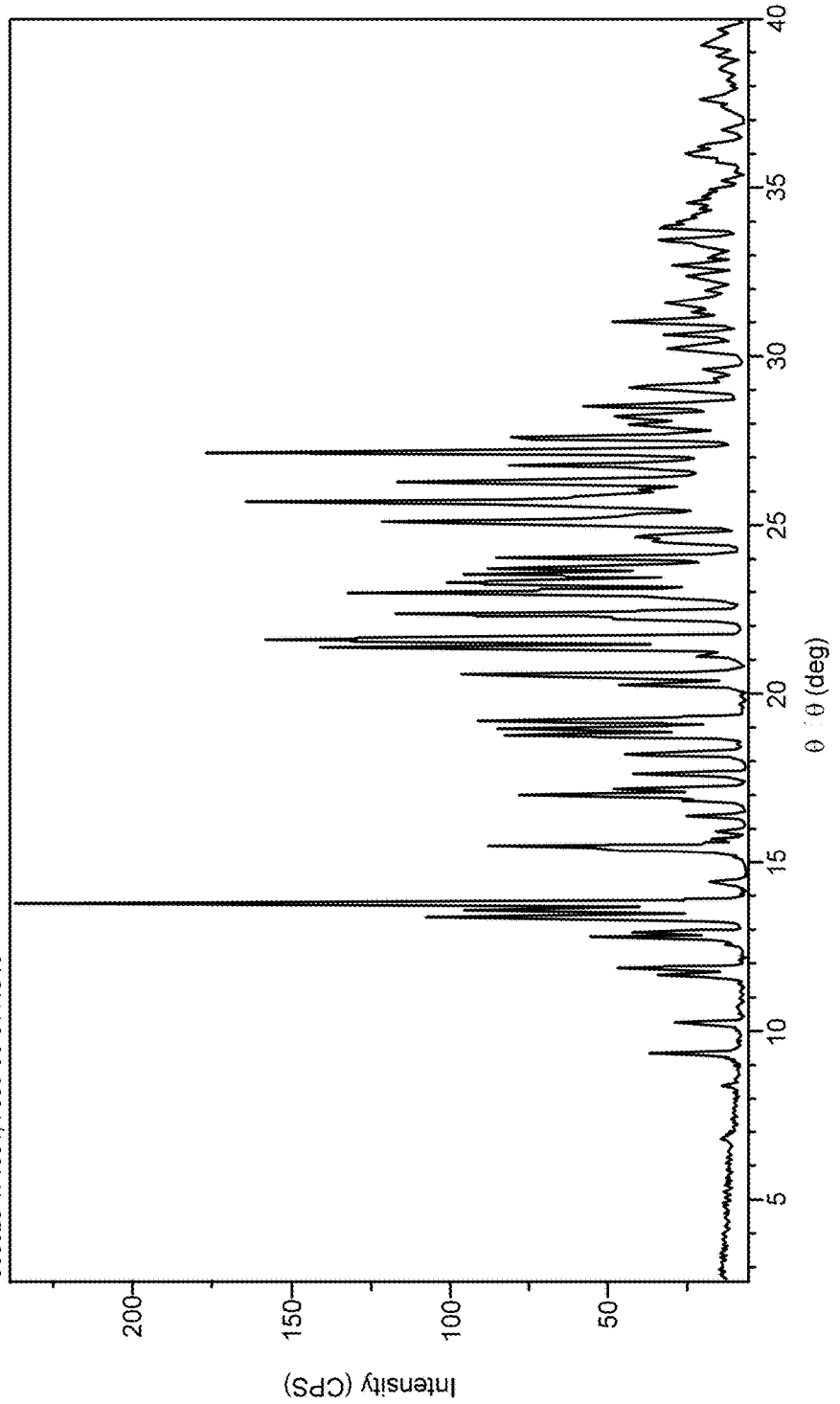
FIG. 14 shows an X-ray powder diffraction (XRPD) pattern of the bromide salt of Formula IX.

The bromide salt of Formula IX is composed of a crystalline material (FIG. 14). The ¹H NMR spectrum is consistent with the chemical structure of AG-10. DMSO, approximately 1 mole was also observed based on the peak at 2.54 ppm.

The bromide content was found to be 17.7% by mass based on IC and is in agreement with the calculated bromide content (17.7%) of an AG10 bromide DMSO 1:1:1 solvate.

Figure 15:
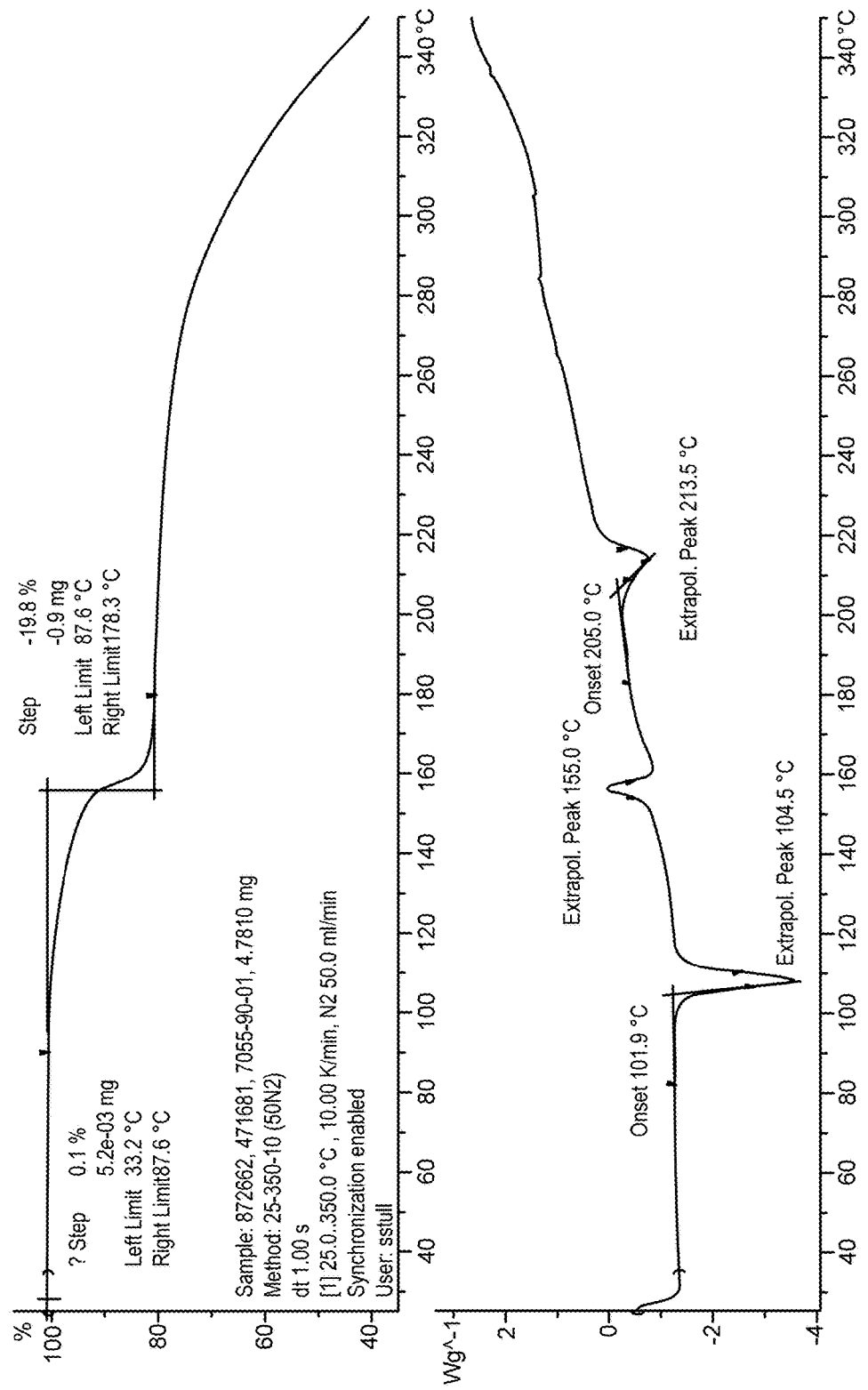
FIG. 15 shows thermo-gravimetric analysis (TGA) and differential scanning calorimetry (DSC) plots of the bromide salt of Formula IX

An endotherm at ~105° C. (peak max), followed by an exotherm at 155° C. (peak max) and an endotherm at ~214° C. is observed in the DSC data (FIG. 15). A weight loss of 19.9% is observed upon heating up to ~182° C., likely associated with the loss of solvent and possible recrystallization into an unsolvated form (FIG. 15).

Example 23

The Preparation of the Nitrate Salt of Formula IX

Figure 16:
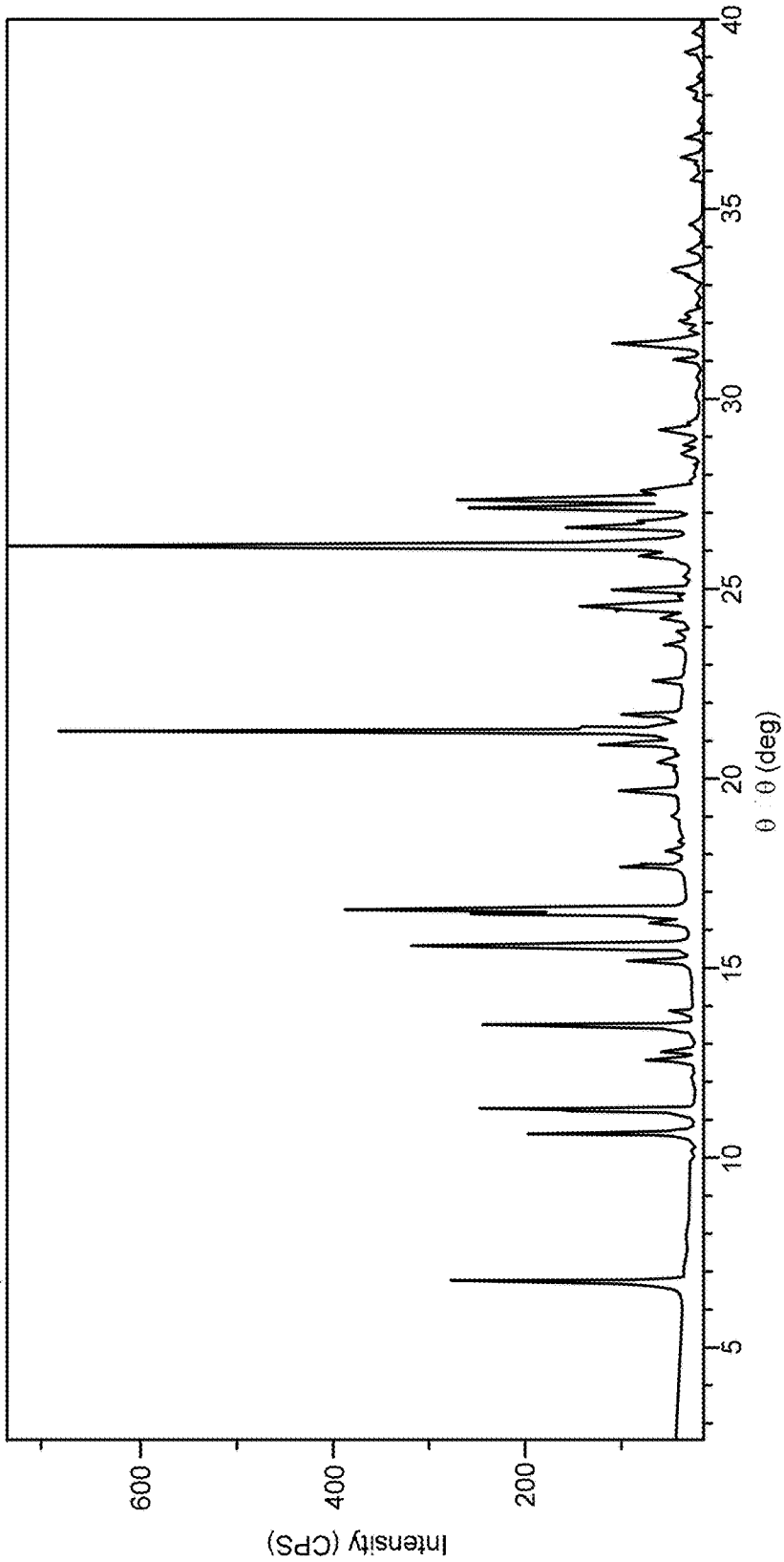
FIG. 16 shows an X-ray powder diffraction (XRPD) pattern of form a of the nitrate salt of Formula IX.

Two nitrate salt forms of Formula IX were identified. The two forms are referred to as Form a and Form b.
Nitrate Salt, Form a Form a of the nitrate salt of Formula IX precipitated from a DMSO solution containing AG10 and nitric acid in equimolar ratios. AG-10 Nitrate Material A is a composed of a single crystalline phase based on successful indexing of the XRPD pattern (FIG. 16).

The solution ¹H NMR spectrum for AG10 Nitrate Form A is consistent with the chemical structure of AG-10. DMSO, approximately 0.8 mole is present based on the peak at 2.54 ppm. Water and minor additional peaks are also observed.

Figure 17:
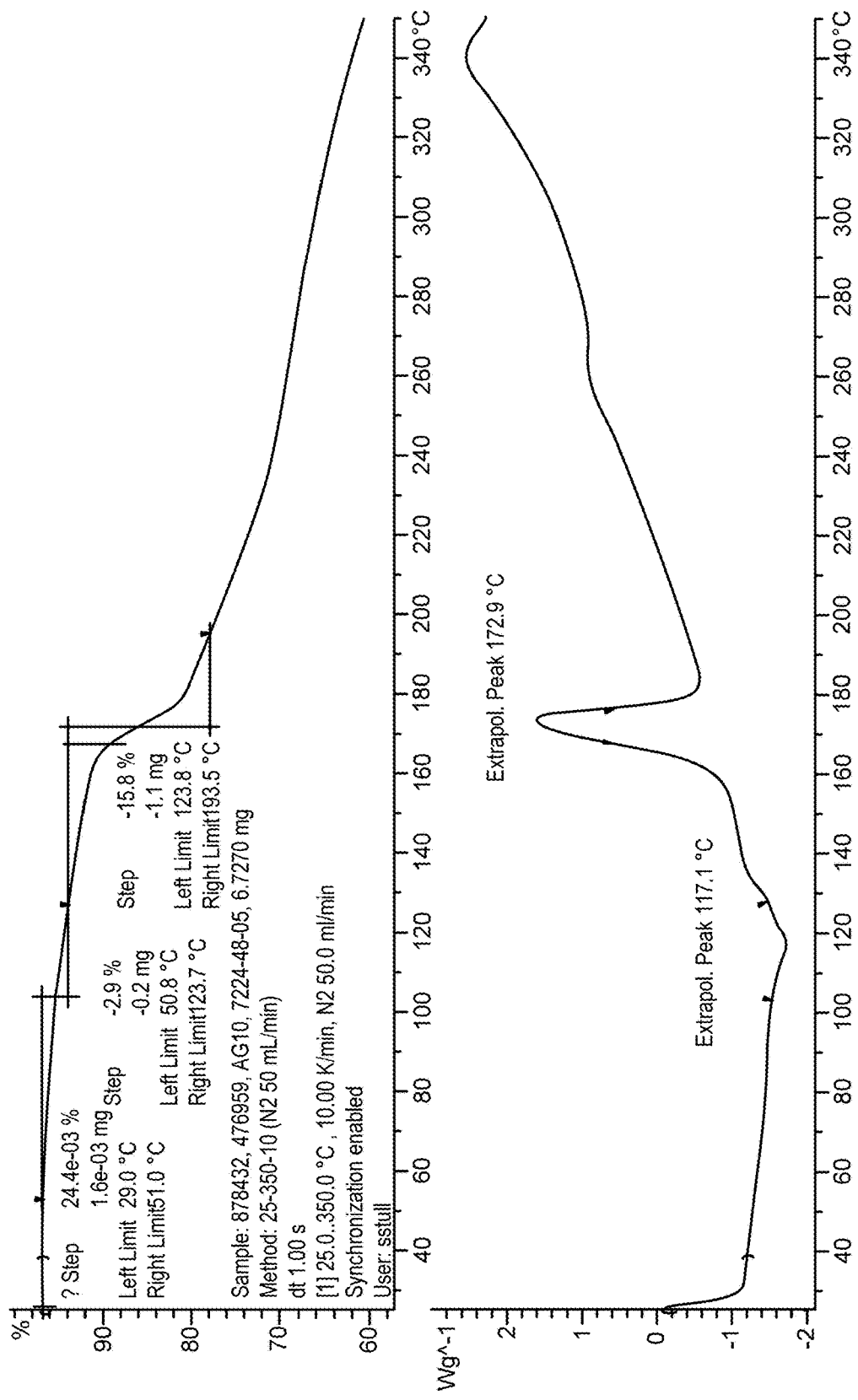
FIG. 17 shows thermo-gravimetric analysis (TGA) and differential scanning calorimetry (DSC) plots of form a of the nitrate salt of Formula IX.

The DSC thermogram exhibits a broad endotherm at ~117° C., which is associated with a weight loss of 2.5% likely attributable to the loss of volatiles (FIG. 17). The broad endotherm is followed be an exotherm with peak maximum at ~173° C., that is associated with a weight loss of ~16% likely due to melt/decomposition (FIG. 17).

The nitrate content was found to be 7.5% by mass based on IC which is not consistent with the calculated nitrate content anticipated for a unsolvated 1:1 nitrate salt (theoretical nitrate content: 17.5%) or even a 1:1:1 AG10 nitrate DMSO solvate (theoretical nitrate: 14.3%).

Nitrate Salt, Form b

Figure 18:
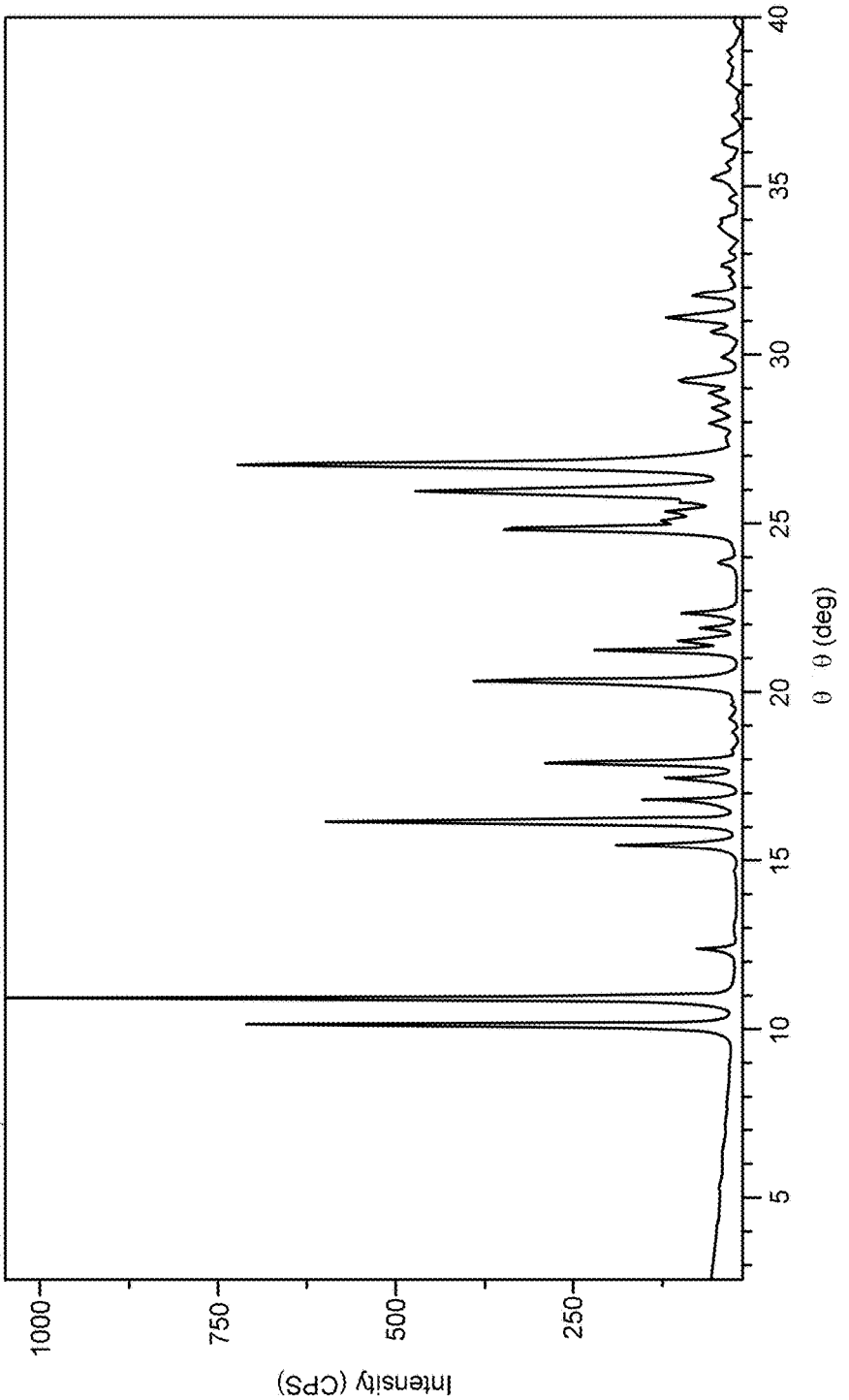
FIG. 18 shows an X-ray powder diffraction (XRPD) pattern of form b of the nitrate salt of Formula IX.

Form b of the nitrate salt of Formula IX was prepared by evaporation of a THF solution containing AG-10 and nitric acid in an equimolar ratio. The XRPD pattern of this solid is shown in FIG. 18.

The solution $^1$H NMR spectrum for AG10 Nitrate Material B is consistent with the chemical structure of AG-10.

The nitrate content was found to be 16.9% by mass based on IC, and is in general agreement with an approximately 1:1 AG-10 nitrate salt.

Example 24

The Preparation of the Sulfate Salt of Formula IX

Figure 19:
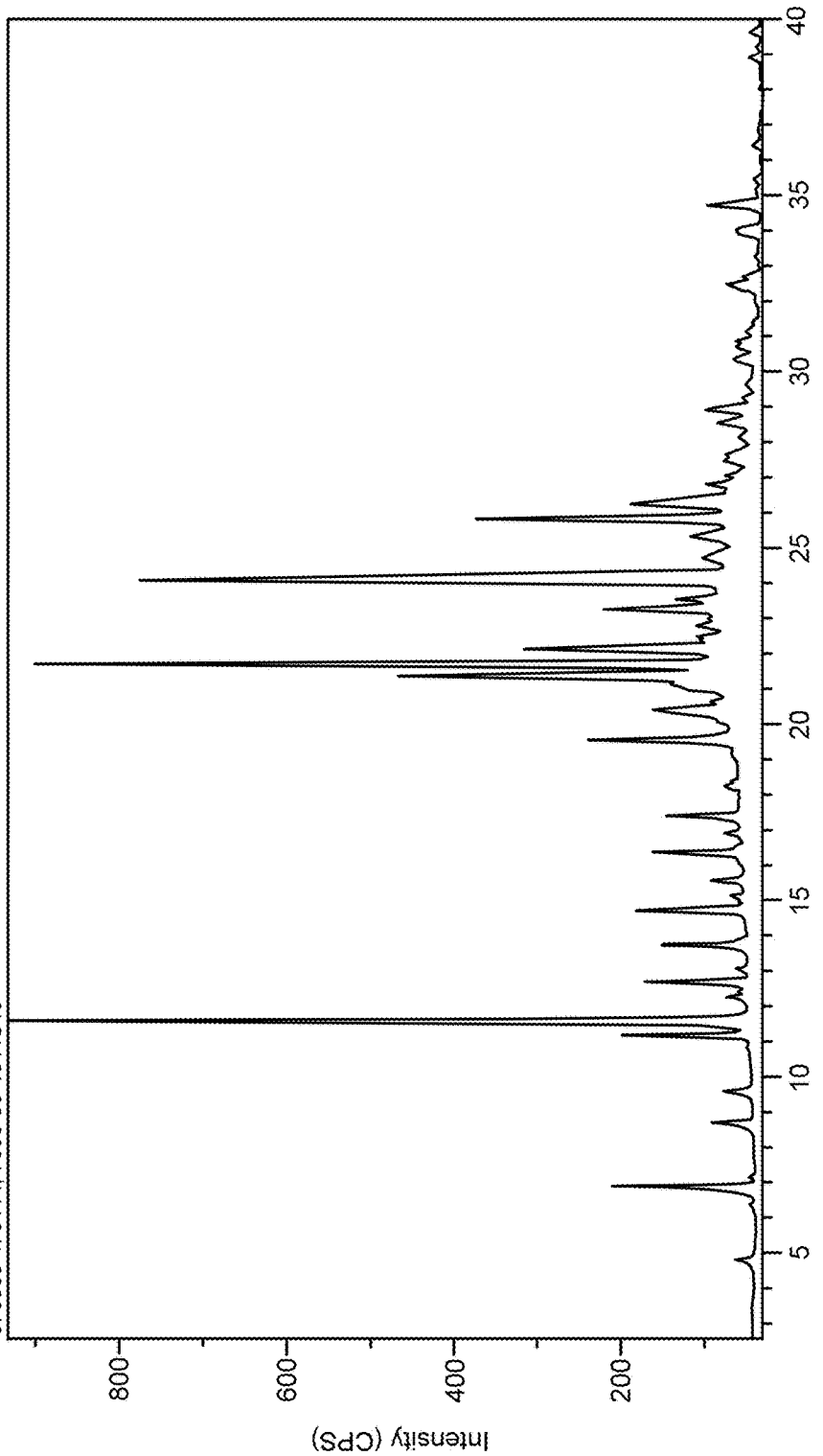
FIG. 19 shows an X-ray powder diffraction (XRPD) pattern of the sulfate salt of Formula IX.

The sulfate salt of Formula IX was prepared by evaporation of an ethanol solution containing equimolar amounts of AG-10 and sulfuric acid that was produced upon cooling (60° C. to 2-8° C.). The sulfate salt of Formula IX is composed of a crystalline material (FIG. 19).

The $^1$H NMR spectrum confirms the presence of AG 10 and contains approximately 1 mole of ethanol based on the peaks at 1.06 and 3.4 ppm. Additional unknown peaks were also observed in the spectrum.

The sulfate content was found to be 15.9% by mass based on IC, which corresponds to an AG10:sulfate ratio of 1:0.58.

Figure 20:
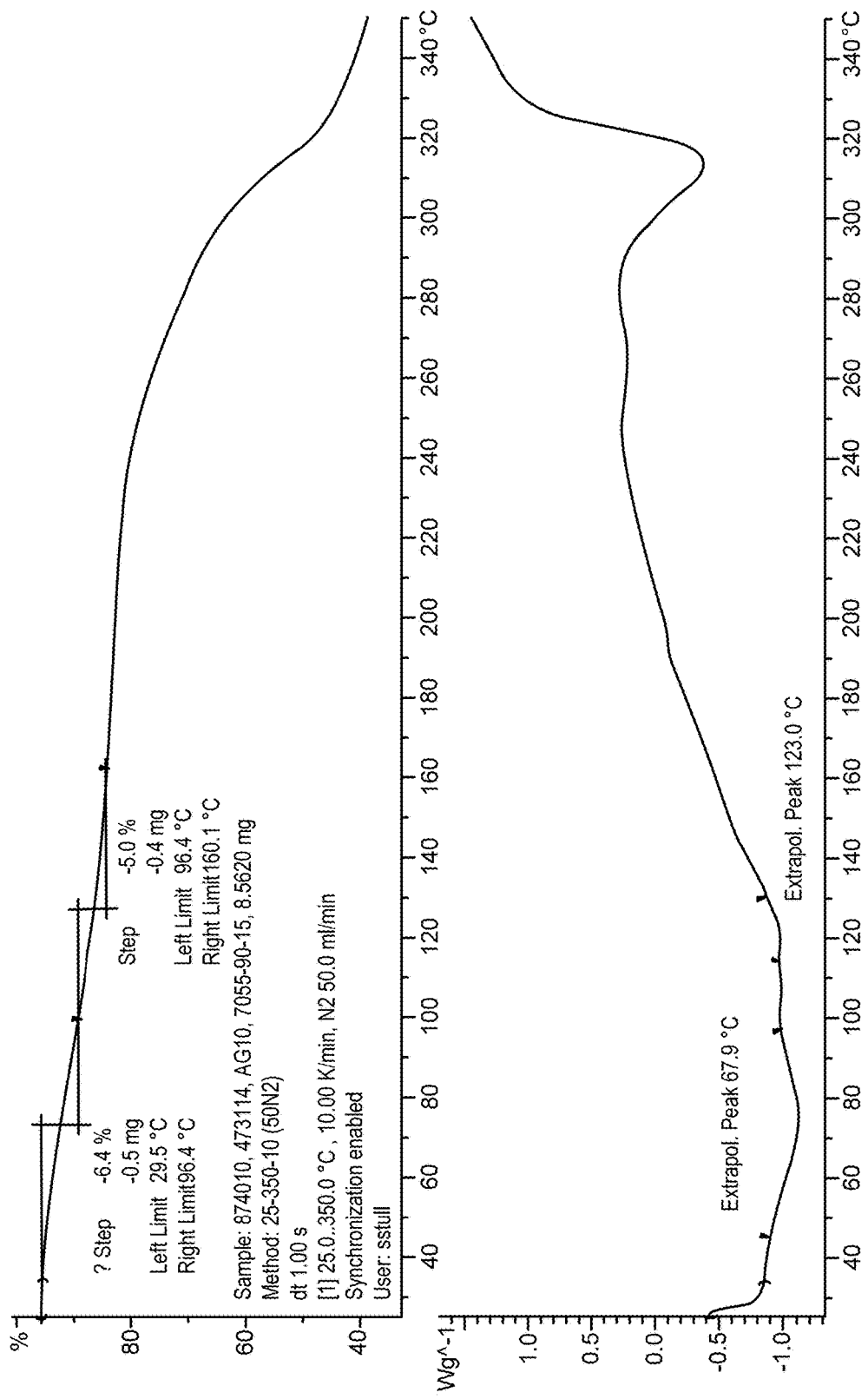
FIG. 20 shows thermo-gravimetric analysis (TGA) and differential scanning calorimetry (DSC) plots of the sulfate salt of Formula IX

A weight loss of 6.4% is observed in the TGA thermogram between ~30° C. and 96° C., equivalent to 1 mole ethanol, assuming an AG10 sulfate 2:1 salt (FIG. 20). Broad features are observed by DSC (FIG. 20).

Example 25

The Preparation of the Citrate Salt of Formula IX

Single crystals of the citrate salt of Formula IX were obtained after an IPA solution saturated with citric acid and containing AG-10 was allowed to evaporate at room temperature. After recovery of a suitable single crystal for SCXRD, the sample was allowed to evaporate further and solids collected were composed of a mixture of AG-10 citrate and citric acid based on XRPD.

The structure of AG10 citrate was determined successfully. The crystal system is triclinic and the space group is P$\bar{1}$. The cell parameters and calculated volume are: $\alpha$=7.64605(12) Å, b=8.37443(13) Å, c=17.8097(3) Å, $\alpha$=87.9509(14)°, $\beta$=79.7770(14)°, $\gamma$=88.3139(13)°, V=1121.24(3) Å$^3$. The formula weight is 484.43 g mol$^{-1}$ with Z=2, resulting in a calculated density of 1.435 g cm$^{-3}$.

A second experiment was performed aimed at obtaining bulk solids of AG 10 citrate as a single crystalline phase for further characterization. The experiment also resulted in a physical mixture of AG10 citrate and citric acid.

Example 26

The Preparation of the Oxalate Salt of Formula IX

The oxalate salt of Formula IX precipitated from a DMA solution containing AG10 and oxalic acid (1:1 mole ratio) at 50° C. The sample was cooled to room temperature and solids isolated for characterization.

Figure 21:
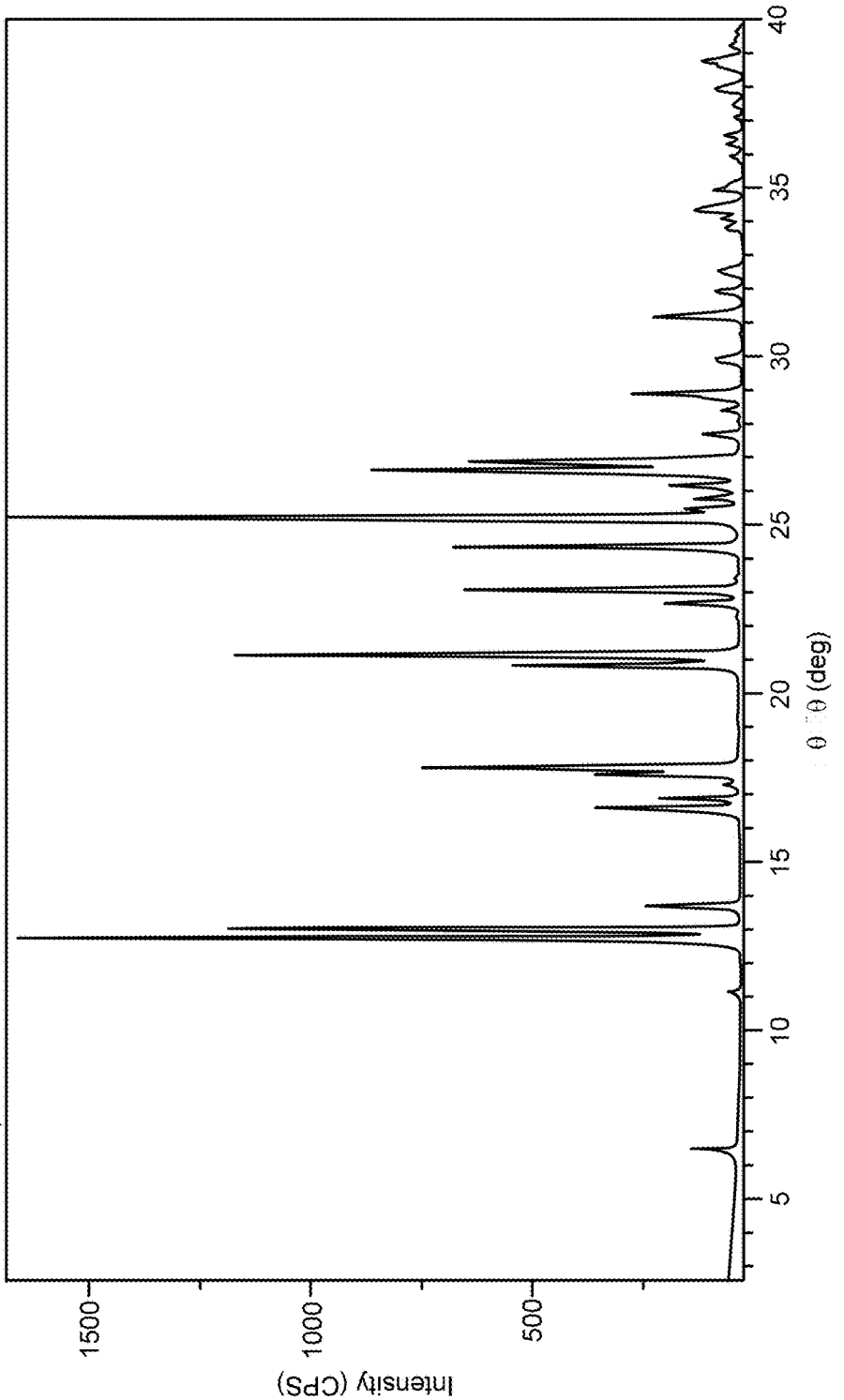
FIG. 21 shows an X-ray powder diffraction (XRPD) pattern of the oxalate salt of Formula IX.

By XRPD, the oxalate salt of Formula IX is composed of a crystalline material (FIG. 21). The XRPD pattern of the sample was successfully indexed indicating the sample is composed primarily or exclusively of a single crystalline phase. The indexed volume is consistent with an AG10 hemi-oxalate based on considerations of molecular volume.

$^1$H NMR spectrum is consistent with the chemical structure of AG-10. DMA, approximately 0.1 mole and water were also present in the spectrum.

By IC, the oxalate content of the sample was determined to be 13.7%, confirming the ~2:1 stoichiometry of AG 10 hemi-oxalate salt.

Figure 22:
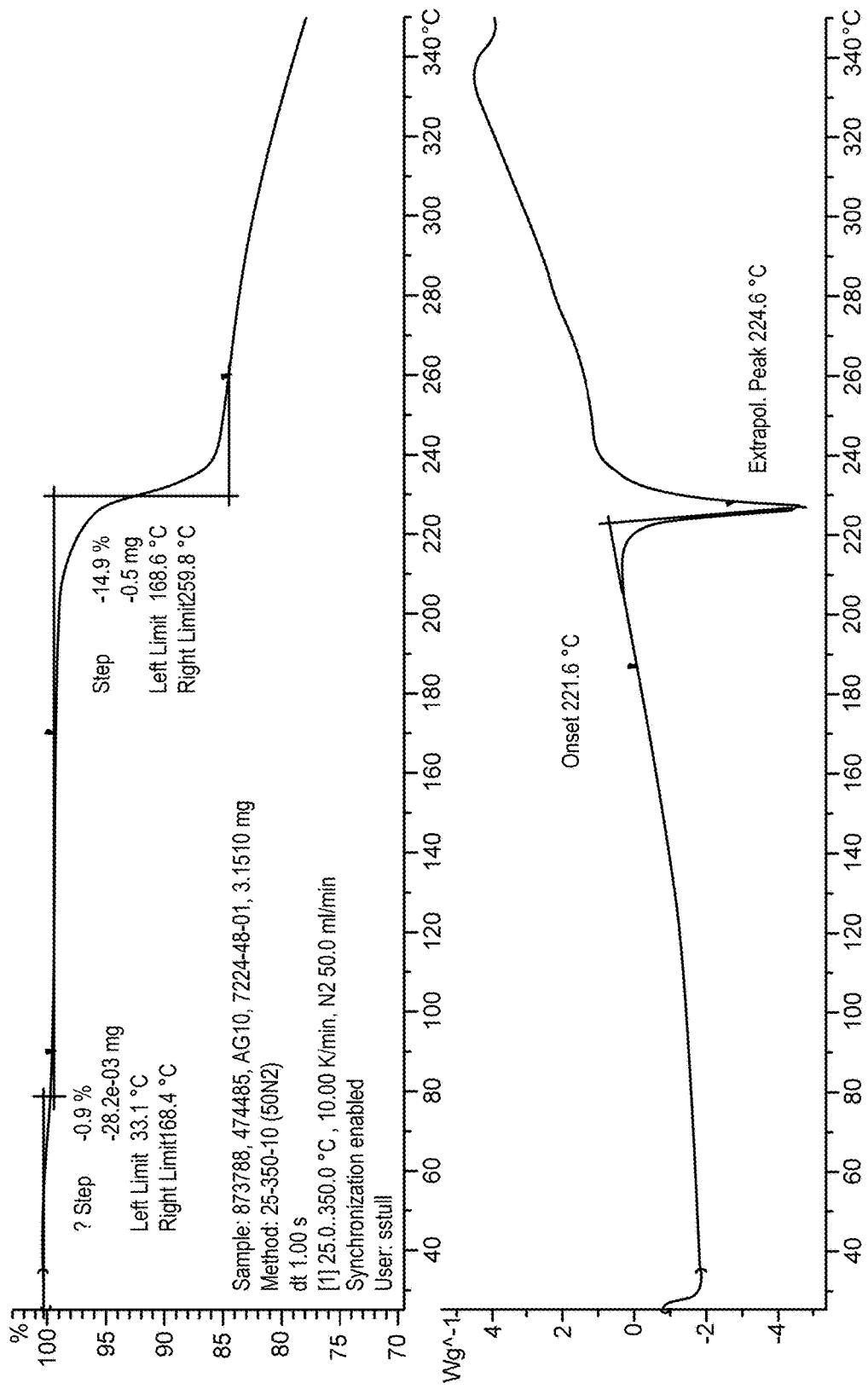
FIG. 22 shows thermo-gravimetric analysis (TGA) and differential scanning calorimetry (DSC) plots of the oxalate salt of Formula IX.

A single endotherm at ~225° C. (peak max) is observed in the DSC data likely attributable to melt/decomposition based on TGA data (FIG. 22). The TGA thermogram exhibits an initial weight loss of 0.9% upon heating between 33° C. and 169° C., likely due to the loss of residual surface solvent such as DMA which was observed by $^1$H NMR (FIG. 22).

Example 27

The Preparation of the Maleate Salt of Formula IX

Two maleate salt forms of Formula IX were identified. The two forms are referred to as Form a and Form b.

Maleate Salt, Form a

The addition of a nitromethane solution of maleic acid (2.2 mole equivalents) to AG-10 at 70° C. resulted in a suspension. The suspension was cooled to room temperature and reheated to 60° C. twice before solids were isolated.

Figure 23:
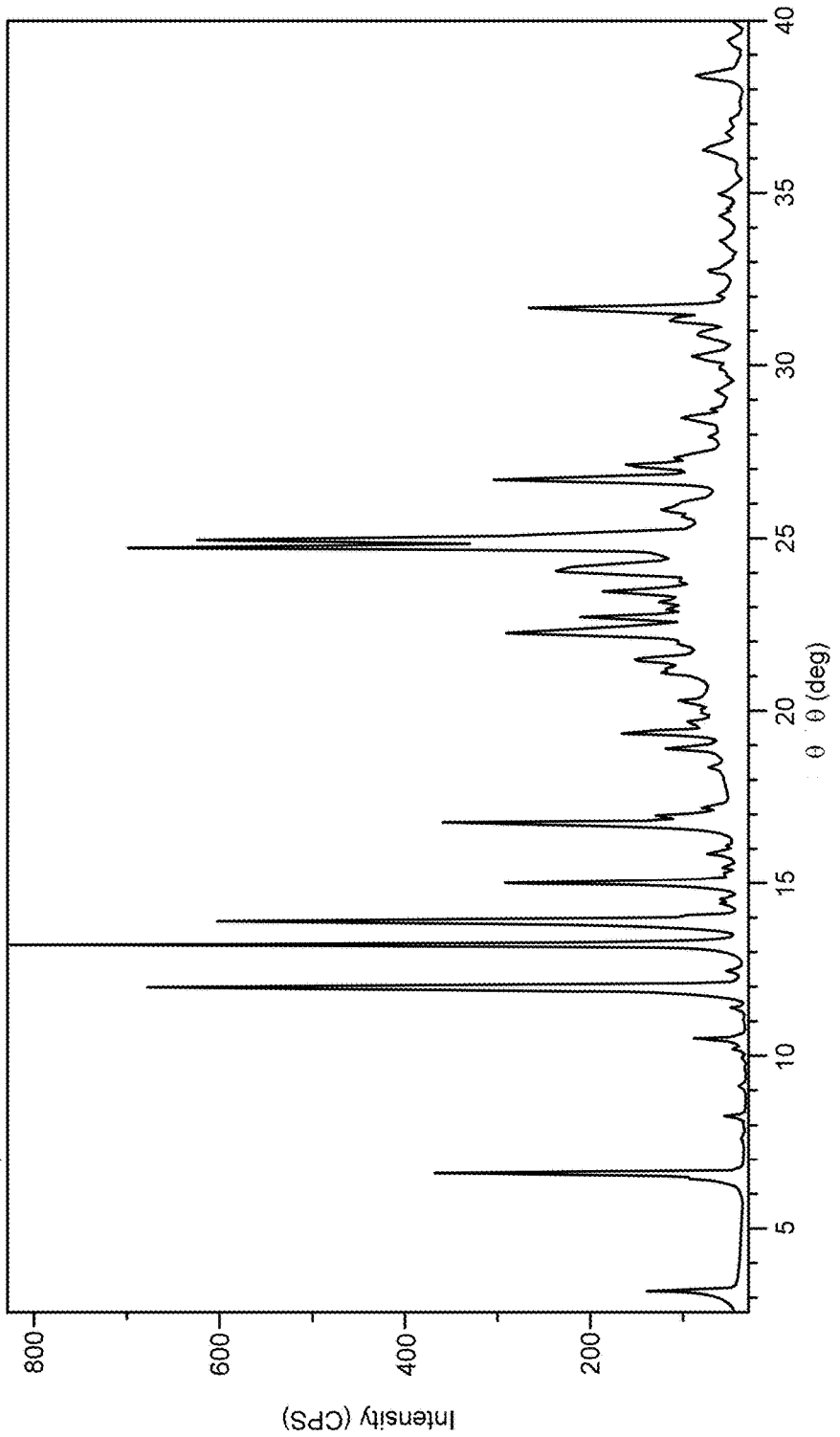
FIG. 23 shows an X-ray powder diffraction (XRPD) pattern of form a of the maleate salt of Formula IX.

Form a of the maleate salt of Formula IX is composed of a crystalline material based on XRPD (FIG. 23). The XRPD pattern was not able to be indexed which suggest the material is not composed of a single crystalline phase and is a possible mixture of forms. XRPD analysis suggests that form a of the maleate salt of Formula IX was isolated as a mixture of form b of the maleate salt of Formula IX.

The $^1$H NMR spectrum of the sample contained AG-10: maleic acid in approximate 1:1 mole ratio based on the peak at 6.23 ppm. Approximately 1.3 moles nitromethane is observed for each mole of AG10 based on the presence of the peak at 4.42 ppm. Minor additional unknown peaks were also observed in the spectrum.

Figure 24:
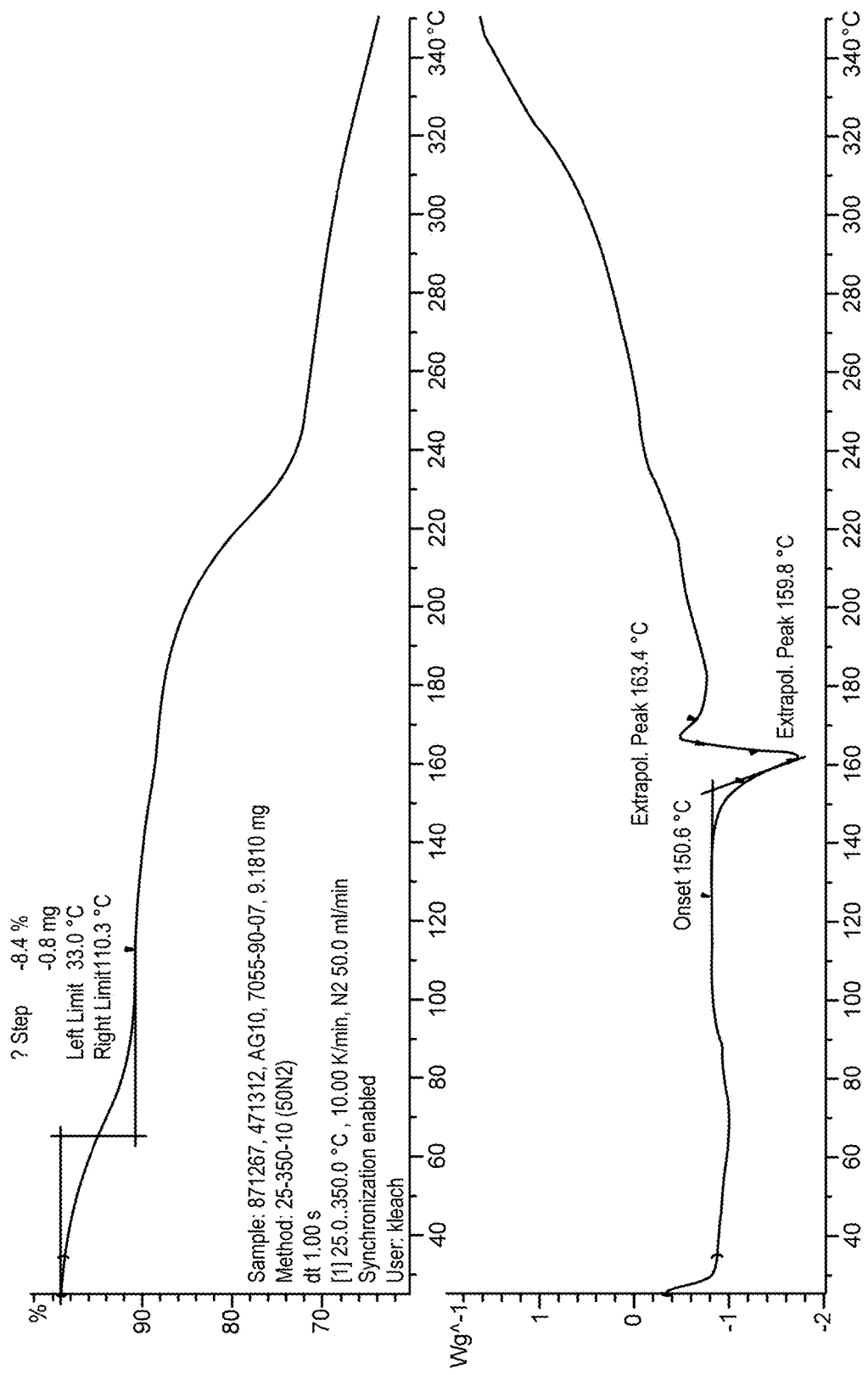
FIG. 24 shows thermo-gravimetric analysis (TGA) and differential scanning calorimetry (DSC) plots form a of the maleate salt of Formula IX.

An endotherm at ~160° C. (peak max) is observed in the DSC data (FIG. 24). A weight loss of 8.4% is seen upon heating to 110° C. which may be due to the loss of solvent (FIG. 24). A sample of form a of the maleate salt of Formula IX was dried at 110° C. for approximately 7 minutes and resulted in disordered material with peaks consistent with form b of the maleate salt of Formula IX based on XRPD.

The sample is likely composed of a mixture of form b of the maelate salt of Formula IX and a possible nitromethane solvate based on XRPD and $^1$H NMR data.

Maleate Salt, Form b

Form b of the maleate salt of Formula IX was produced from an elevated temperature slurry experiment containing AG-10 and maleic acid (1:1) in p-dioxane. The XRPD pattern of form b of the maleate salt of Formula IX (FIG. 25) was successfully indexed indicating the pattern is composed primarily or exclusively of a single crystalline phase. The indexed volume is consistent with a 1:1 AG10 maleate salt.

The $^1$H NMR spectrum of the sample is consistent with AG10 and maleic acid in a 1:1 mole ratio. Approximately 0.3 moles p-dioxane was also observed in the spectrum.

Figure 26:
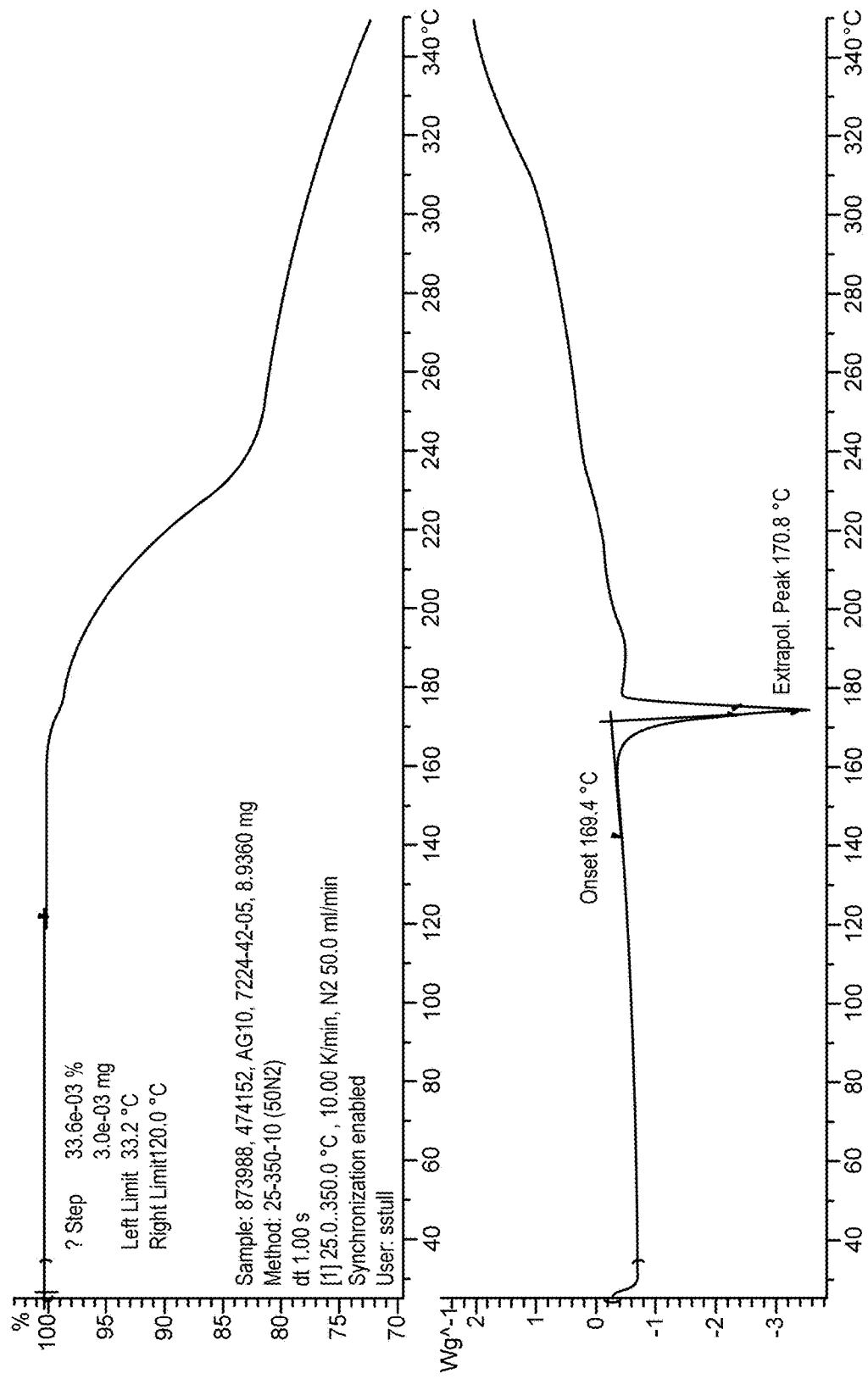
FIG. 26 shows thermo-gravimetric analysis (TGA) and differential scanning calorimetry (DSC) plots of form b of the maleate salt of Formula IX.

A single endotherm is observed at ~171° C. (peak max) in the DSC thermogram (FIG. 26). No significant weight loss is observed upon heating the sample between 33° C. and 120° C. (FIG. 26).

Example 28

The Preparation of the Acetic Acid Salt of Formula IX

The acetic acid salt of Formula IX was produced by directly milling AG-10 with acetic acid in a 1:1 mole ratio.

Figure 27:
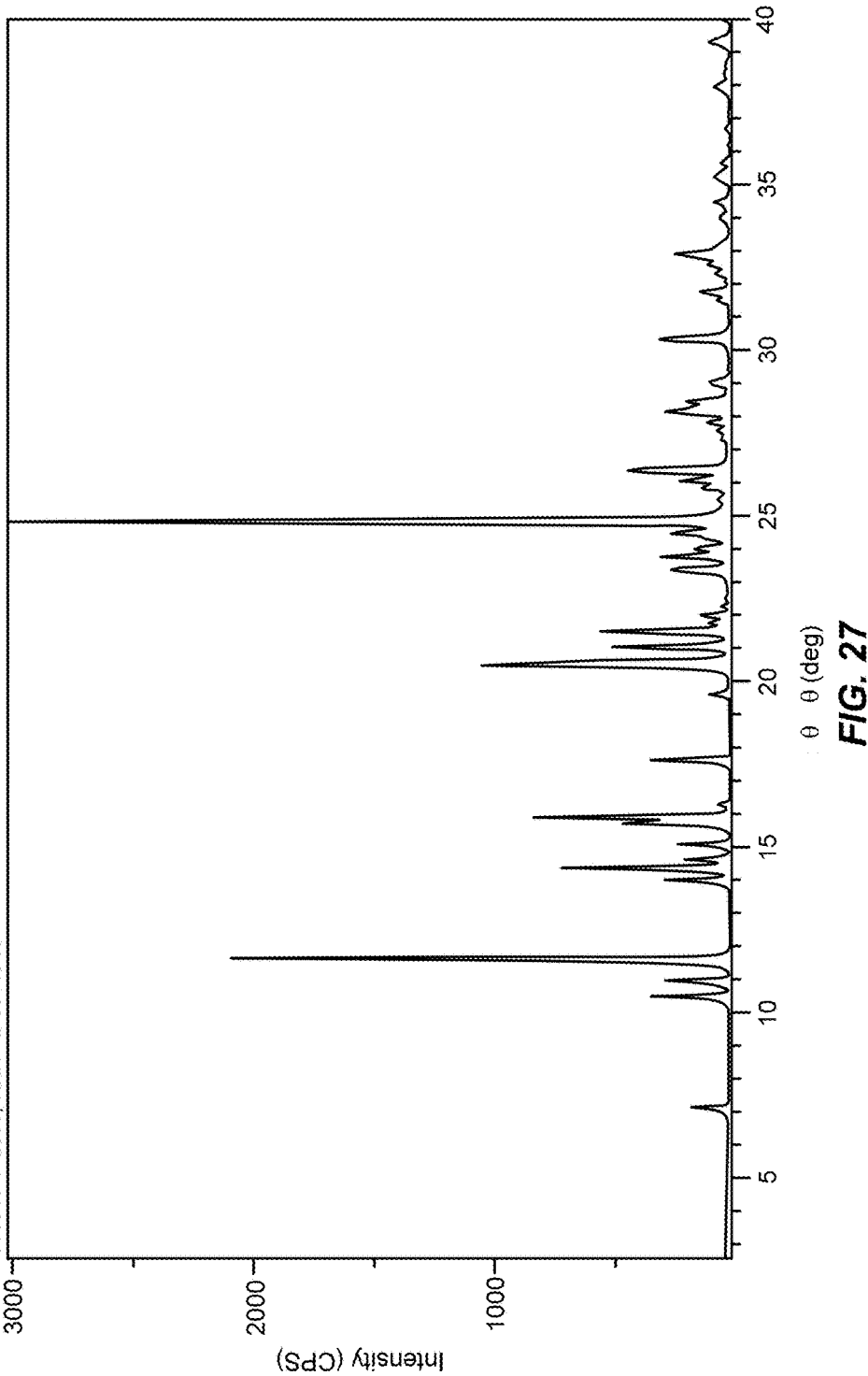
FIG. 27 shows an X-ray powder diffraction (XRPD) pattern of the acetic acid salt of Formula IX.

By XRPD, the acetic acid salt of Formula IX is composed of a crystalline material and is shown in FIG. 27. The XRPD pattern was successfully indexed indicating the sample is composed primarily or exclusively of a single crystalline phase.

The $^1$H NMR spectrum is consistent with the chemical structure of AG-10, with approximately 0.9 mole acetic acid present.

Figure 28:
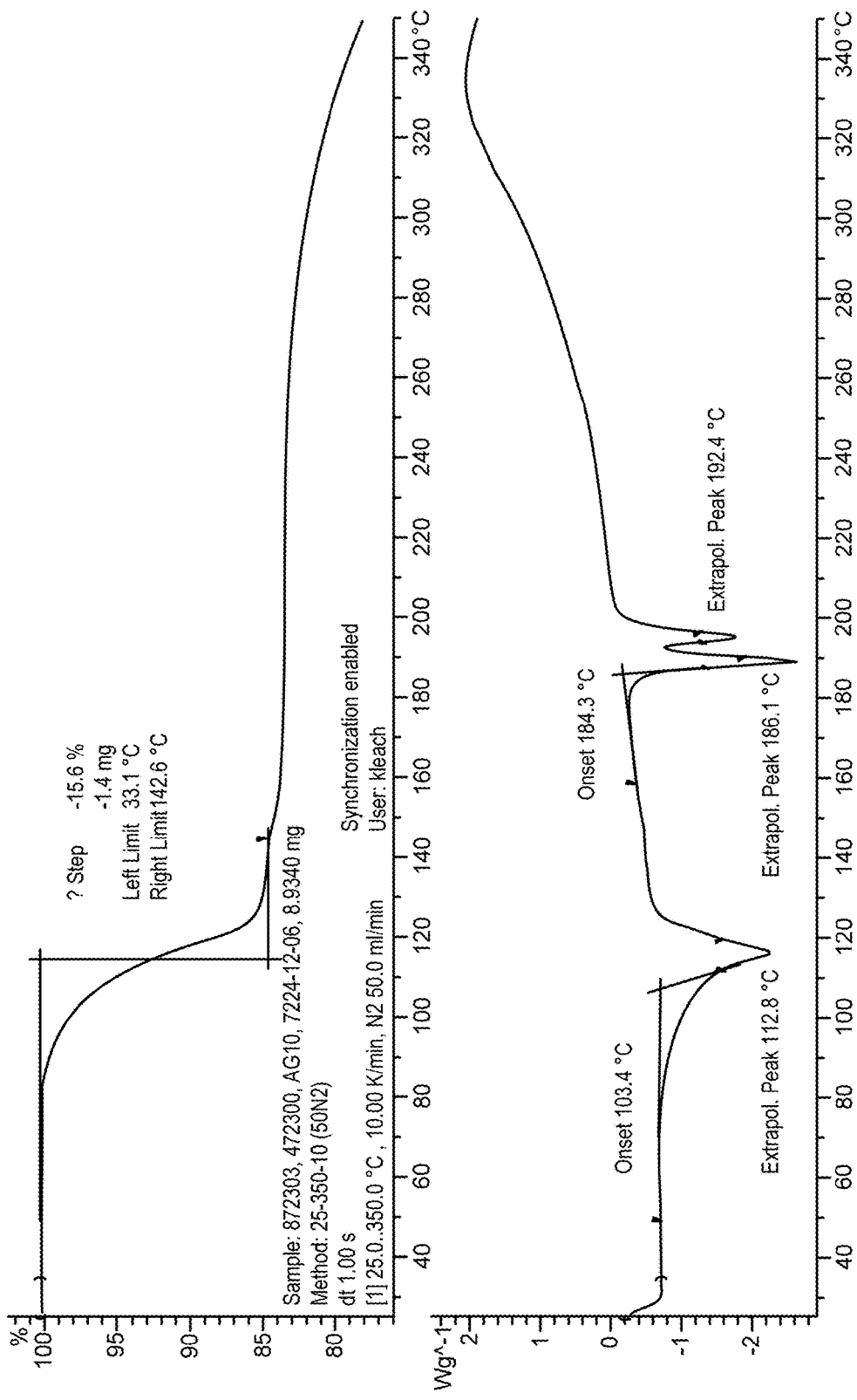
FIG. 28 shows thermo-gravimetric analysis (TGA) and differential scanning calorimetry (DSC) plots of the acetic acid salt of Formula IX.

The DSC thermogram showed a broad endotherm at ~113° C. that is associated with a weight loss of ~16% likely due to the loss of acetic acid (FIG. 28). This is followed by endotherms at 186° C. and 192° (peak max) that are likely attributable to melting of AG10 free form (FIG. 28).

Example 29

The Preparation of the L-malic Acid Salt of Formula IX

Figure 29:
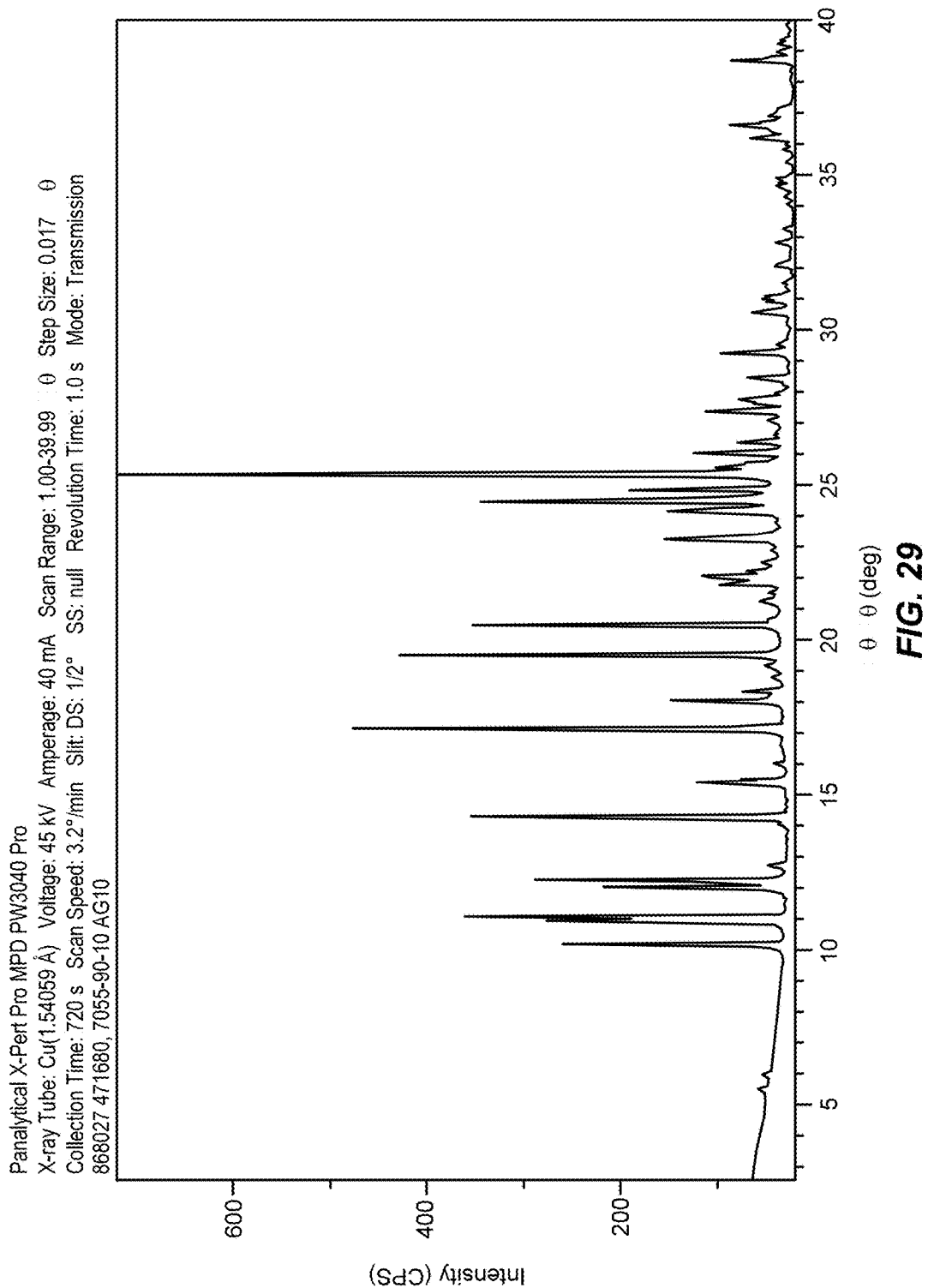
FIG. 29 shows an X-ray powder diffraction (XRPD) pattern of the L-malic acid salt of Formula IX.

Cooling of a solution produced by the addition of a saturated solution of L-malic acid in nitromethane to AG-10 at 60° C., produced solids at sub-ambient temperature. The XRPD pattern is composed of a unique crystalline material designated the L-malic acid salt of Formula IX (FIG. 29).

$^1$H NMR spectrum contained 1.8 moles of malic acid per mole of AG-10 based on the peak at 4.2 ppm. Minor ACN and water were also observed in the spectrum.

Figure 30:
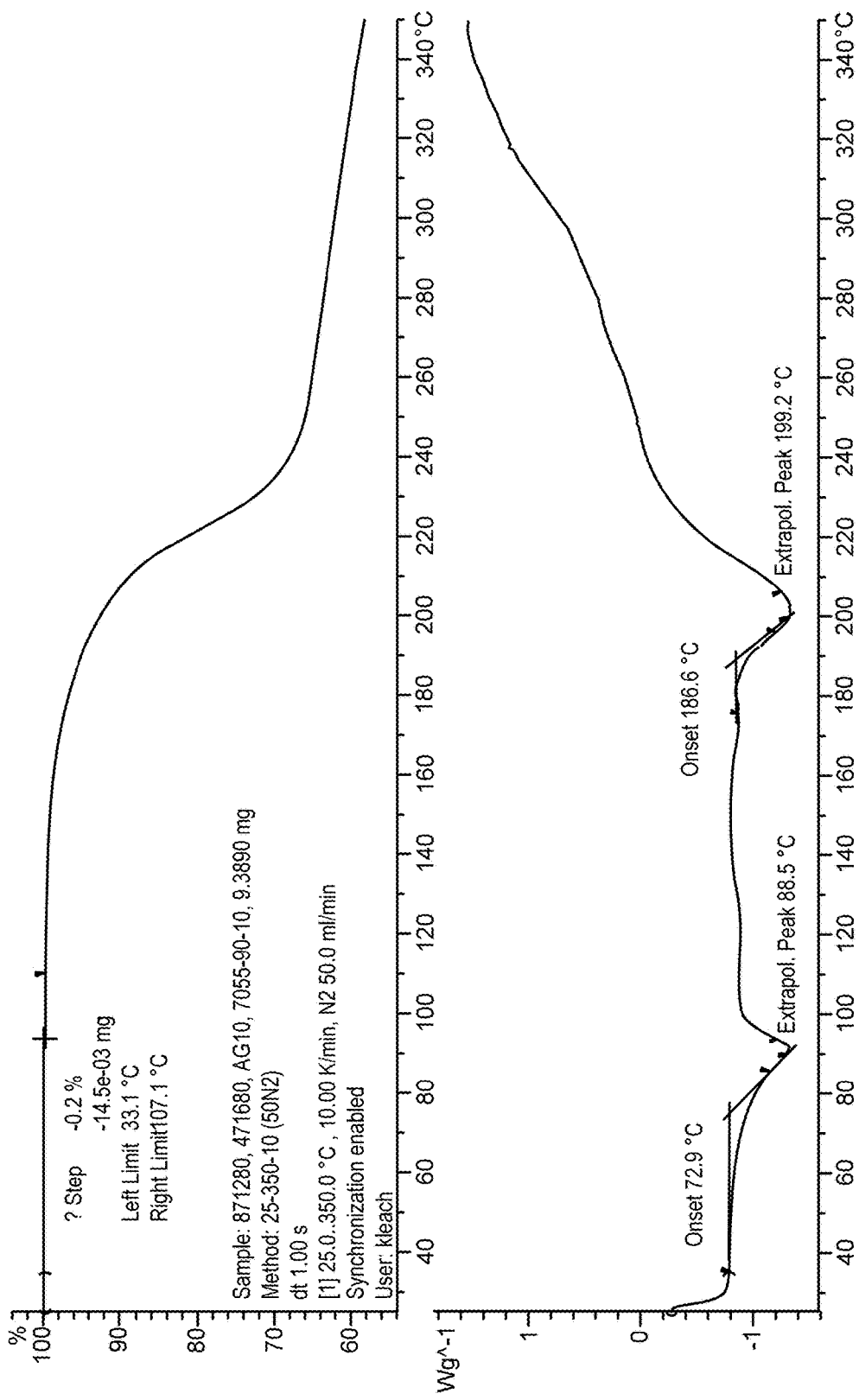
FIG. 30 shows thermo-gravimetric analysis (TGA) and differential scanning calorimetry (DSC) plots of the L-malic acid salt of Formula IX.

Two broad endotherms are observed in the DSC data with peak maxima at ~89° C. and 199° C. (FIG. 30). A weight loss of 0.2% is observed between 33° C. and 107° C. (FIG. 30).

Example 30

Crystalline Type A of Formula IX

Figure 32:
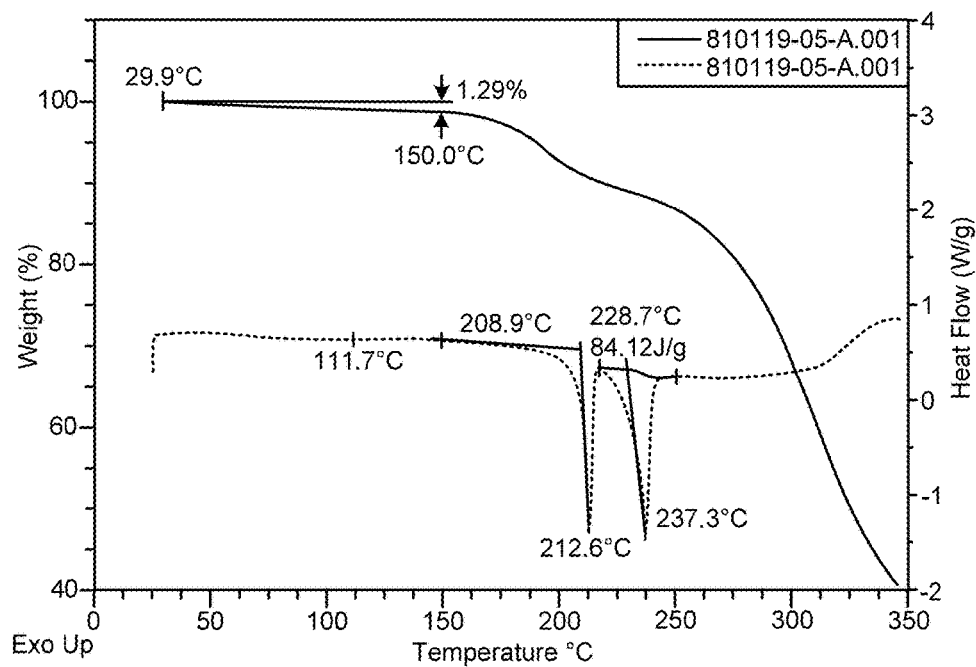
FIG. 32, FIG. 33, FIG. 34 shows thermo-gravimetric analysis (TGA) and differential scanning calorimetry (DSC) plots of crystalline Type A of Formula IX.
Figure 33:
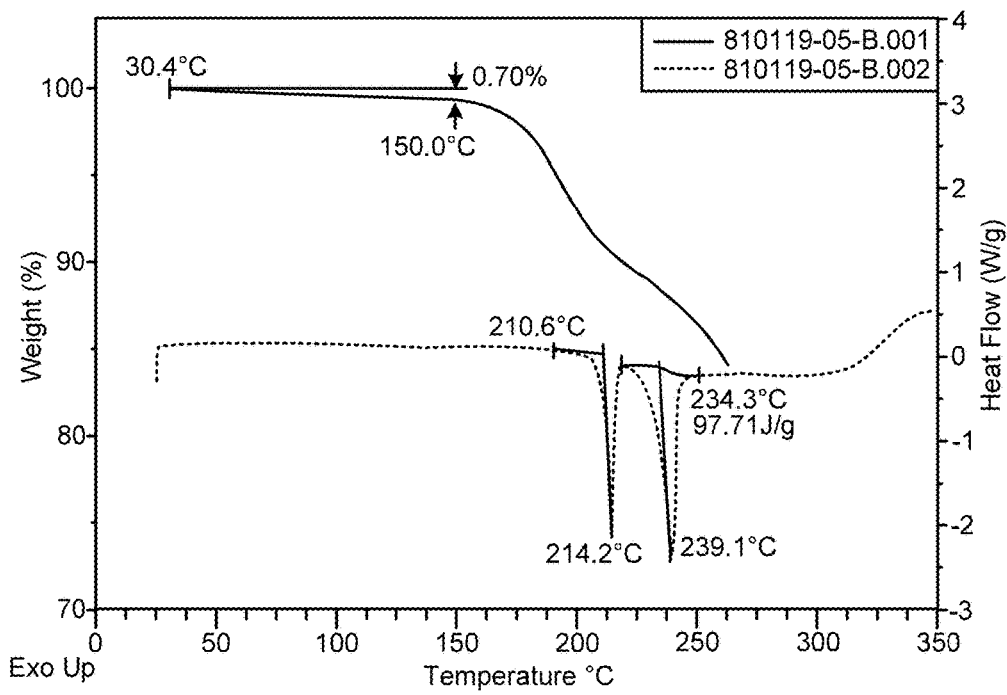
Figure 34:
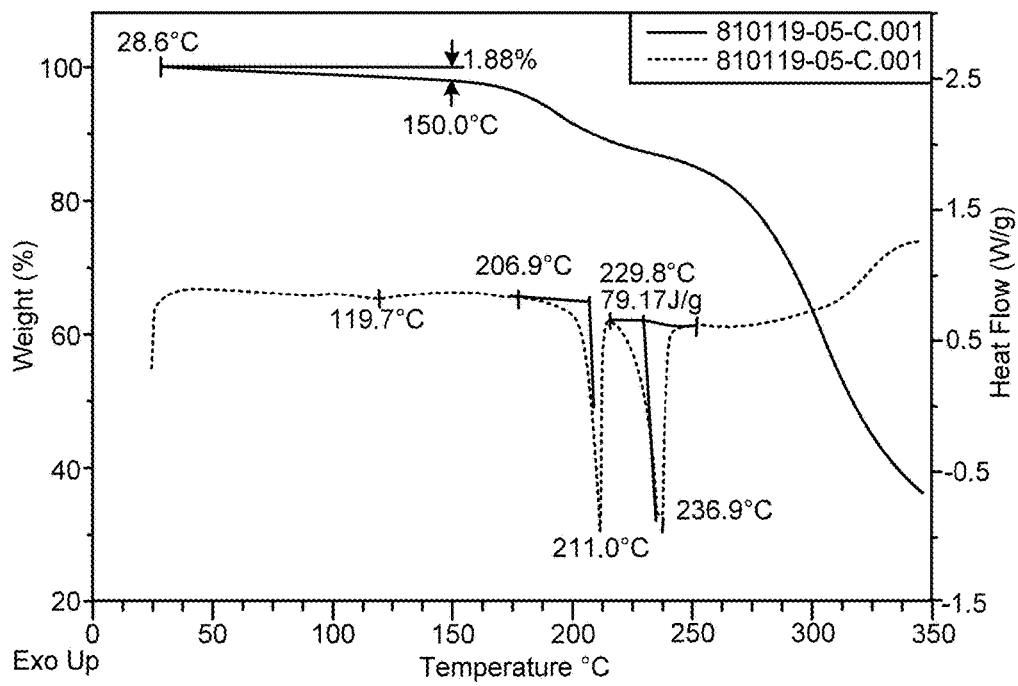
Figure 35:
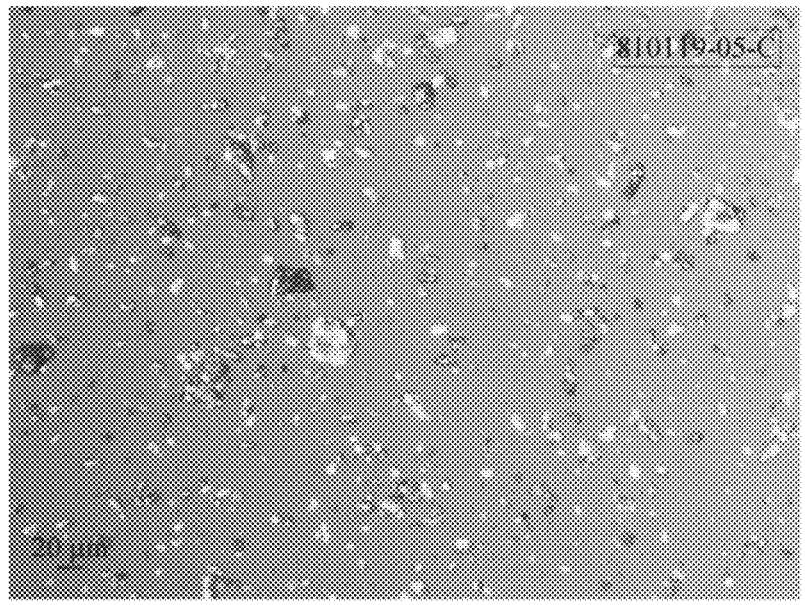
FIG. 35 shows a polarized light microscopy (PLM) image of crystalline Type A of Formula IX.

The material of Formula Ia (HCl salt of Formula IX) as prepared in Example 7 was characterized by X-ray powder diffraction (XRPD) (FIG. 31), thermo-gravimetric analysis (TGA) (FIG. 32-FIG. 34), differential scanning calorimetry (DSC) (FIG. 32-FIG. 34) and polarized light microscopy (PLM) (FIG. 35). This material was referred to as crystalline Type A of Formula IX. Three different XRPD plots are overlaid in FIG. 31 showing three different preparations according to Example 7.

Figure 31:
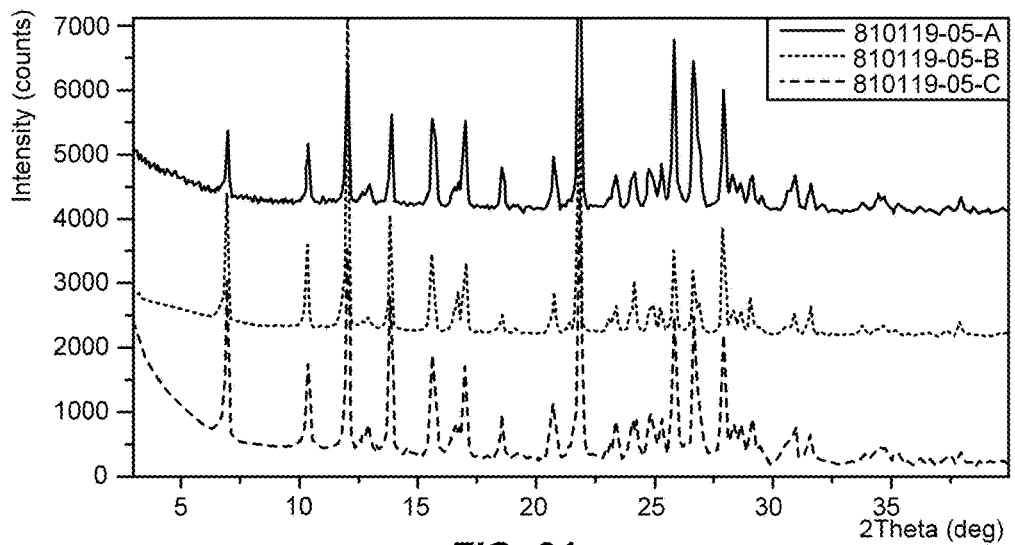
FIG. 31 shows an X-ray powder diffraction (XRPD) pattern of crystalline Type A of Formula IX (3 different samples).

Representative peak values of the XRPD plots shown in FIG. 31 are provided in Table 7, below.

TABLE 7

Representative XRPD peak values for Crystalline Type A of Formula IX

| Position [°2θ] | Relative Intensity [%] |
| --- | --- |
| 7.0 | 23.50 |
| 10.4 | 21.74 |
| 12.0 | 51.77 |
| 13.0 | 6.45 |
| 13.9 | 34.17 |
| 15.6 | 31.64 |

TABLE 7-continued

Representative XRPD peak values for Crystalline Type A of Formula IX

| Position [°2θ] | Relative Intensity [%] |
| --- | --- |
| 17.0 | 31.28 |
| 18.6 | 15.02 |
| 20.8 | 19.23 |
| 21.8 | 100.00 |
| 23.3 | 12.57 |
| 24.2 | 14.33 |
| 24.7 | 14.29 |
| 25.3 | 17.29 |
| 25.9 | 63.60 |
| 26.7 | 55.94 |
| 27.9 | 44.84 |
| 28.2 | 12.96 |
| 28.6 | 10.35 |
| 29.1 | 13.20 |
| 30.9 | 13.10 |
| 31.6 | 10.76 |
| 33.8 | 2.95 |
| 34.5 | 4.62 |
| 37.9 | 4.55 |

Three separate TGA/DSC plots of crystalline Type A of Formula IX are shown in FIG. 32 to FIG. 35. Weight losses of about 0.7% to 1.9% upon heating to around 150° C. was measured by thermal gravimetric analysis, and further characterization using differential scanning calorimetry shows at least two endothermic peaks at about 211-214° C. and 237-239° C. The HPLC purity of crystalline Type A of Formula IX was determined to be 98.76 area %.

Figure 36:
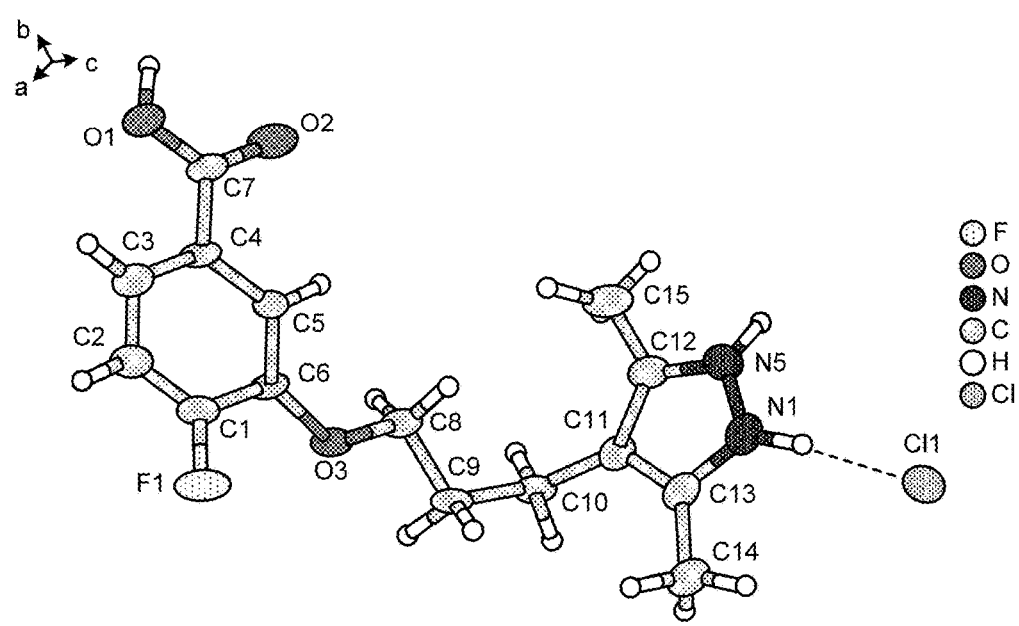
FIG. 36 shows the asymmetric unit of crystalline Type A of Formula IX.

The asymmetric unit of crystalline Type A of Formula IX is shown in FIG. 36. It includes one cation of compound AG 10 freebase and one chloride ion (the HCl molecule transferred the proton to N1 atom of freebase), indicating Type A was an anhydrous mono-HCl salt form.

Figure 38:
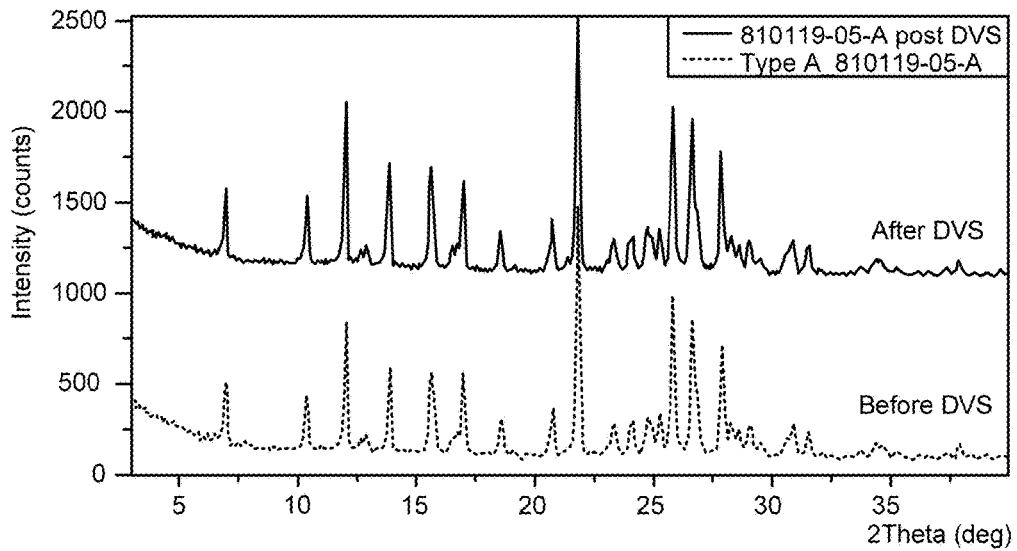
FIG. 38 shows X-ray powder diffraction (XRPD) patterns of crystalline Type A of Formula IX before (lower) and after (upper) DVS.

To evaluate the hygroscopicity and physical stability of crystalline Type A of Formula IX under different humidity, dynamic vapor sorption (DVS) data was collected at 25° C. after the sample was pre-equilibrated at 0% RH to remove unbounded water. DVS result (FIG. 37) showed a water uptake of 1.6% at 25° C/80% RH, suggesting crystalline Type A of Formula IX slightly hygroscopic. Additionally, XRPD results (FIG. 38) showed no form change before and after DVS test.

Example 31

Polymorphic Screen of AG-10

Using crystalline Type A of Formula IX as the starting material, polymorph screening experiments were performed under 98 conditions, through methods of vapor diffusion, anti-solvent addition, slurry conversion, slow evaporation, and slow cooling. From polymorph screening and follow-up investigation, a total of ten additional crystal forms were obtained including six HCl salt forms (Type A/B/E/H/I/J), two freebase forms (Type C/G) and two currently unidentified forms (Type D/F). Forms of Type A/B/E were identified to be anhydrates. Type I was identified to be a hydrate. Type H and J were identified to be a MeOH solvate and DMAc solvate, respectively. The methods utilized and crystal forms identified are summarized in Table 8.

TABLE 8

Summary of polymorph screening of AG 10

| Method | No. of Experiments | Isolated Solid Forms |
|---|---|---|
| Anti-solvent addition | 24 | Type A, C, D, E, Type A + extra peaks |
| Slow evaporation | 7 | Type A, H |
| Slow cooling | 8 | Type A, E, J |
| Slurry conversion | 25 | Type A, C, F, G |
| Solid vapor diffusion | 13 | Type A, Type A + extra peaks |
| Liquid vapor diffusion | 21 | Type A |
| Total | 98 | Type A, C, D, E, F, G, H, J, Type A + extra peaks |

Anti-Solvent Addition

A total of 24 anti-solvent addition experiments were carried out. For each experiment, about 15 mg of crystalline form Type A of Formula IX was weighed into a 20-mL glass vial, followed by the addition of 0.125-0.63 mL corresponding solvent. The mixture was then magnetically stirred at the speed of 750 RPM to get a clear solution at RT. Subsequently, the corresponding anti-solvent was added to the solution to induce precipitation or until the total amount of anti-solvent reached 10.0 mL. The clear solutions were transferred to slurry at 5° C. If no precipitation occurred, the solution was then transferred to fast evaporation at RT or vacuum drying at RT. The solids were isolated for XRPD analysis. Results summarized in Table 9 showed that Type A, C, D, E and Type A with extra peaks were obtained.

TABLE 9

Summary of anti-solvent addition experiments

| Solvent | Anti-Solvent | Final Results |
|---|---|---|
| DMSO | IPA | Type A + one peak** |
|  | Acetone | Type A + one peak* |
|  | EtOAc | Type A |
|  | THF | Type A** |
|  | ACN | Type A* |
|  | Toluene | Type E |
|  | DCM | Type A |
|  | H$_2$O | Type C |
| MeOH | MEK | Type A |
|  | IPAc | Type D |
|  | 2-MeTHF | Type A* |
|  | CPME | Type A |
|  | ACN | Type A |
|  | H$_2$O | Type C |
|  | CHCl$_3$ | Type A + extra peaks** |
|  | Toluene | Type A + extra peaks |
| EtOH | MIBK | Type A |
|  | EtOAc | Type A** |
|  | 1,4-Dioxane | Gel |
|  | Anisole | Type A** |
|  | ACN | Type E* |
|  | DCM | Type A** |
|  | n-Heptane | Type A |
|  | H$_2$O | Type C |

*solids were obtained via stirring at 5° C.
**solids were obtained via fast evaporation or vacuum drying at RT.

Slow Evaporation

Slow evaporation experiments were performed under 7 conditions. For each experiment, around 15 mg of crystalline Type A of Formula IX was weighed into a 3-mL glass vial, followed by the addition of corresponding solvent or solvent mixture to get a clear solution. Subsequently, the vial was covered with parafilm with 3~4 pinholes, and kept at RT to allow the solution to evaporate slowly. The isolated solids were tested by XRPD. As summarized in Table 10, Type A and H were generated.

TABLE 10

Summary of slow evaporation experiments

| Solvent (v:v) | Final Results |
|---|---|
| MeOH | Type A |
| EtOH | Type A |
| DCM/MeOH, 1:1 | Type A |
| Acetone/MeOH, 4:1 | Type H |
| EtOAc/EtOH, 4:1 | Gel |
| THF/MeOH, 4:1 | Type A |
| ACN/EtOH, 4:1 | Type A |

Slow Cooling

Slow cooling experiments were conducted in 8 solvent systems. For each experiment, about 15-35 mg of crystalline Type A of Formula IX was suspended in 0.8-2.0 mL of corresponding solvent in a 3-mL glass vial at RT. The suspension was transferred to slurry at 50° C. with a magnetic stirrer at the speed of 750 RPM. The sample was equilibrated at 50° C. for 1 hr. and filtered using a 0.45 μm PTFE membrane. Subsequently, the filtrate was slowly cooled down from 50° C. to 5° C. at a rate of 0.1° C./min. If no precipitation occurred, the solution was then transferred to fast evaporation at RT or vacuum drying at RT. The results summarized in Table 11 indicated that Type A, E and J were obtained.

TABLE 11

Summary of slow cooling experiments

| Solvent, v:v | Final Results* |
|---|---|
| EtOH | Type E |
| IPA | Type A** |
| MEK/DMAc, 3:1 | Type J** |
| IPAc/EtOH, 3:1 | Type A |
| Anisole/MeOH, 3:1 | Type A |
| ACN/NMP, 3:1 | Clear solution |
| H2O/DMAc, 3:1 | Type J** |
| CHCl$_3$/EtOH, 3:1 | Type E |

*all the samples were transferred to slow evaporation at RT.
**solids were obtained after vacuum drying at 50° C. was performed on the clear solutions.

Slurry Conversion at RT

Slurry conversion experiments were conducted at RT in different solvent systems. For each experiment, about 15-35 mg of crystalline Type A of Formula IX was suspended in 0.3-2.0 mL corresponding solvent in a 1.5-mL glass vial. After the suspension was magnetically stirred for 4 days at RT, the remaining solids were isolated for XRPD analysis. Results summarized in Table 12 showed that Type A, C and G were obtained.

TABLE 12

Summary of slurry conversion experiments at RT

| Solvent, v:v | Final Results |
|---|---|
| EtOH | Type A |
| H$_2$O | Type C |
| EtOH/H$_2$O, 97:3, a$_w$ = 0.2 | Type A |
| EtOH/H$_2$O, 927:73, a$_w$ = 0.4 | Type A |
| EtOH/H$_2$O, 86:14, a$_w$ = 0.6 | Type A |
| EtOH/H$_2$O, 71:29, a$_w$ = 0.8 | Type A |
| H$_2$O/DMAc, 3:1 | Type G |
| MIBK/MeOH, 1:1 | Type A |
| THF/H$_2$O, 9:1 | Type A |
| ACN/EtOH, 3:1 | Type A |
| DCM/DMSO, 3:1 | Type A |
| EtOAc/DMF, 3:1 | Type A |

Slurry Conversion at 50° C.

Slurry conversion experiments were conducted at 50° C. in different solvent systems. For each experiment, about 15 mg of crystalline Type A of Formula IX was suspended in 1.0 mL corresponding solvent in a 1.5-mL glass vial. After the suspension was magnetically stirred for 4 days at 50° C., the remaining solids were isolated for XRPD analysis. Results summarized in Table 13 indicated that Type A and F were obtained.

TABLE 13

Summary of slurry conversion experiments at 50° C.

| Solvent | Temperature, ° C. | Final Results |
|---|---|---|
| IPA | 50 | Type A |
| CHCl$_3$ | | Type A |
| Acetone | | Type A |
| MEK | | Type A |
| IPAc | | Type A |
| EtOAc | | Type A |
| Anisole | | Type A |
| THF | | Type A |
| 2-MeTHF | | Type A |
| 1,4-Dioxane | | Type A |
| ACN | | Type A |
| Toluene | | Type F |
| 1-Butanol | | Type A |

Solid Vapor Diffusion

Solid vapor diffusion experiments were conducted using 13 solvents. For each experiment, about 15 mg of crystalline Type A of Formula IX was weighed into a 3-mL vial, which was placed into a 20-mL vial with 4 mL of corresponding solvent. The 20-mL vial was sealed with a cap and kept at RT for 39 days to allow the solvent vapor to interact with the solid sample. The isolated solids were tested by XRPD. The results summarized in Table 14 indicated that Type A and Type A with extra peaks were obtained.

TABLE 14

Summary of solid vapor diffusion experiments

| Solvent | Final Results |
|---|---|
| H$_2$O | Type A |
| DCM | Type A |
| EtOH | Type A |
| MeOH | Type A |
| ACN | Type A |
| THF | Type A |
| CHCl$_3$ | Type A |
| Acetone | Type A |

TABLE 14-continued

Summary of solid vapor diffusion experiments

| Solvent | Final Results |
|---|---|
| DMF | Type A |
| EtOAc | Type A |
| 1,4-Dioxane | Type A |
| IPA | Type A |
| DMSO | Type A + extra peaks |

Liquid Vapor Diffusion

Twenty-one liquid vapor diffusion experiments were conducted. For each experiment, about 15 mg of crystalline Type A of Formula IX was dissolved in 0.125-0.6 mL of corresponding solvent to obtain a clear solution in a 3-mL vial. Subsequently, the solution was placed into a 20-mL vial with 4 mL of corresponding anti-solvent. The 20-mL vial was sealed with a cap and kept at RT, allowing sufficient time for solvent vapor to interact with the solution. If no precipitation occurred, the solution was then transferred to fast evaporation at RT. Solids were isolated for XRPD analysis. Results summarized in Table 15: showed that Type A was obtained.

TABLE 15

Summary of liquid vapor diffusion experiments

| Solvent, v:v | Anti-solvent | Final Results |
|---|---|---|
| DCM/MeOH, 1:1 | Toluene | Type A |
| | MIBK | Type A |
| | EtOAc | Type A |
| | ACN | Type A |
| | Anisole | Type A |
| EtOH | MEK | Type A |
| | IPAc | Type A |
| | 2-MeTHF | Type A |
| | ACN | Type A |
| | H$_2$O | Type A |
| | CHCl$_3$ | Type A |
| | n-Heptane | Type A |
| | Toluene | Type A |
| DMF | IPA | Clear solution |
| | Acetone | Clear solution |
| | EtOAc | Clear solution |
| | THF | Clear solution |
| | ACN | Clear solution |
| | Toluene | Clear solution |
| | H$_2$O | Limited solid |
| | DCM | Clear solution |

Figure 39:
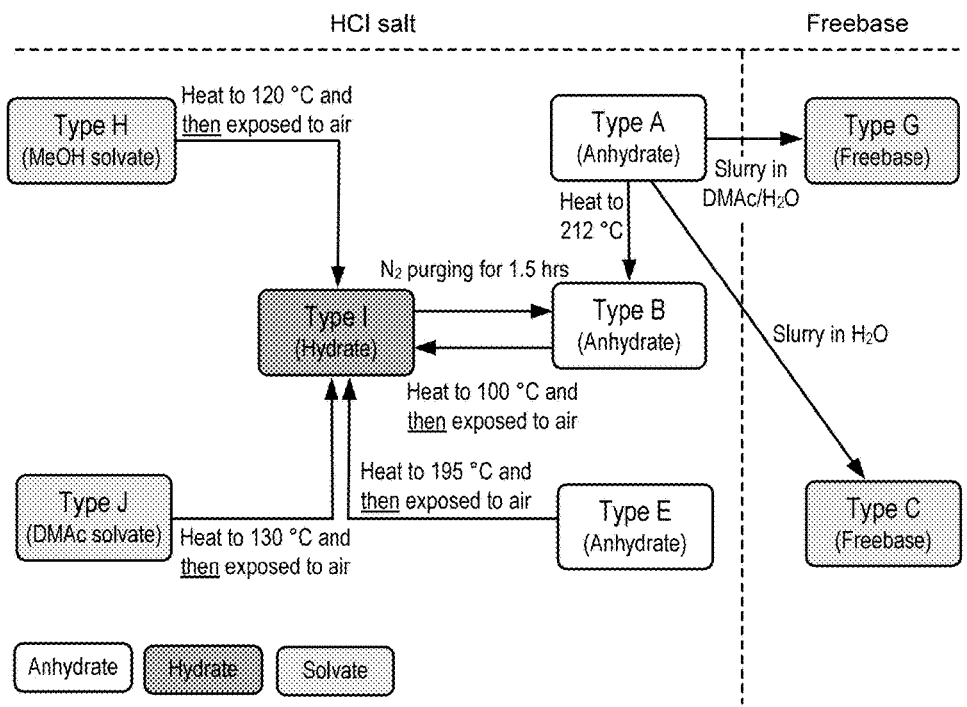
FIG. 39 shows a diagram summarizing the interconversions between identified crystal forms Type A, B, C, E, G, H, I, J.

A chart summarizing the interconversions between the identified crystal forms is shown in FIG. 39.

Abbreviation for Solvents

TABLE 16

Solvent abbreviation list

| Abbreviation | Solvent | Abbreviation | Solvent |
|---|---|---|---|
| MeOH | Methanol | THF | Tetrahydrofuran |
| EtOH | Ethanol | 2-MeTHF | 2-Methyltetrahydrofuran |
| IPA | Isopropyl alcohol | ACN | Acetonitrile |
| MIBK | 4-Methyl-2-pentanone | DMSO | Dimethylsulfoxide |
| EtOAc | Ethyl acetate | DCM | Dichloromethane |
| IPAc | Isopropyl acetate | DMAc | N,N-Dimethylformamide |
| MTBE | Methyl tert-butyl ether | MEK | Methylethyl ketone |

Instruments and Methods

XRPD

For XRPD analysis, PANalytical X-ray powder diffractometers were used. The XRPD parameters used are listed in Table 17.

TABLE 17

Parameters for XRPD test

| Parameters | PANalytical (Reflection Mode) | PANalytical (Reflection Mode) |
| --- | --- | --- |
| Model | Empyrean | X' Pert[3] |
| X-Ray wavelength | Cu, kα, Kα1 (Å): 1.540598, Kα2 (Å): 1.544426 Kα2/Kα1 intensity ratio: 0.50 | Cu, kα, Kα1 (Å): 1.540598, Kα2 (Å): 1.544426 Kα2/Kα1 intensity ratio: 0.50 |
| X-Ray tube setting | 45 kV, 40 mA | 45 kV, 40 mA |
| Divergence slit | Automatic | 1/8° |
| Scan mode | Continuous | Continuous |
| Scan range (2TH) | 3°-40° | 3°-40° |
| Scan step time (s) | 17.8 | 46.7 |
| Step size (°2TH) | 0.0167 | 0.0263 |
| Test Time | 5 min 30 s | 5 min 04 s |

TGA & DSC

TGA data was collected using a TA Q500/Q5000 TGA from TA Instruments. DSC was performed using a TA Q200/Q2000 DSC from TA Instruments. Detailed parameters used are listed in Table 18.

TABLE 18

Parameters for TGA and DSC test

| Parameters | TGA | DSC |
| --- | --- | --- |
| Method | Ramp | Ramp |
| Sample pan | Platinum, open | Aluminum, crimped |
| Temperature | RT-300° C. | 25- target temperature |
| Heating rate | 10° C./min | 10° C./min |
| Purge gas | $N_2$ | $N_2$ |

$^1$H NMR $^1$H NMR data was collected on Bruker 400M NMR Spectrometer using DMSO-$d_6$.

DVS

DVS was measured via a SMS (Surface Measurement Systems) DVS Intrinsic. Parameters for DVS test are listed in Table 19.

TABLE 19

Parameters for DVS test

| Parameters | Value |
| --- | --- |
| Temperature | 25° C. |
| Sample size | 10-20 mg |
| Gas and flow rate | $N_2$, 200 mL/min |
| dm/dt | 0.002%/min |
| Min. dm/dt stability duration | 10 min |
| Max. equilibrium time | 180 min |
| RH range | 0% RH-95% RH-0% RH |
| RH step size | 10% (0% RH-90% RH-0% RH) 5% (90% RH-95% RH and 95% RH-90% RH) |

HPLC

Agilent 1100/1260 HPLC was utilized to analyze purity and solubility, and the detailed method was listed in Table 20.

TABLE 20

HPLC method for purity and solubility test

| Item | Purity | | Solubility | |
| --- | --- | --- | --- | --- |
| Column | Phenomenex Gemini C18 110A, 4.6 × 250 mm, 5.0 μm | | | |
| Mobile phase | A: 0.1% FA in $H_2O$ B: 0.1% FA in Acetonitrile | | | |
| | Time (min) | % B | Time (min) | % B |
| Gradient table | 0.0 | 5 | 0.0 | 5 |
| | 20.0 | 100 | 7.0 | 100 |
| | 20.1 | 5 | 7.1 | 5 |
| | 25.0 | 5 | 10.0 | 5 |
| Run time | 25.0 min | | 10.0 min | |
| Post time | 0.0 min | | 0.0 min | |
| Flow rate | 1.0 mL/min | | | |
| Injection volume | 10 μL | | | |
| Detector wavelength | UV at 254 nm | | | |
| Column temperature | 30° C. | | | |
| Sampler temperature | RT | | | |
| Diluent | ACN:$H_2O$ (1:1) | | | |

IC

IC method for Cl$^-$ content measurement was listed in Table 21.

TABLE 21

IC method for Cl$^-$ content measurement

| Item | Value |
| --- | --- |
| Column | IonPac AS18 Analytical Column (4 × 250 mm) |
| Mobile phase | 25 mM NaOH |
| Injection volume | 25 μL |
| Flow rate | 1.0 mL/min |
| Injection volume | 5 μL |
| Cell temperature | 35° C. |
| Column temperature | 35° C. |
| Current | 80 mA |
| Run time | 6.0 min |

Example 32

The Preparation of Crystalline Type B of Formula IX

Figure 40:
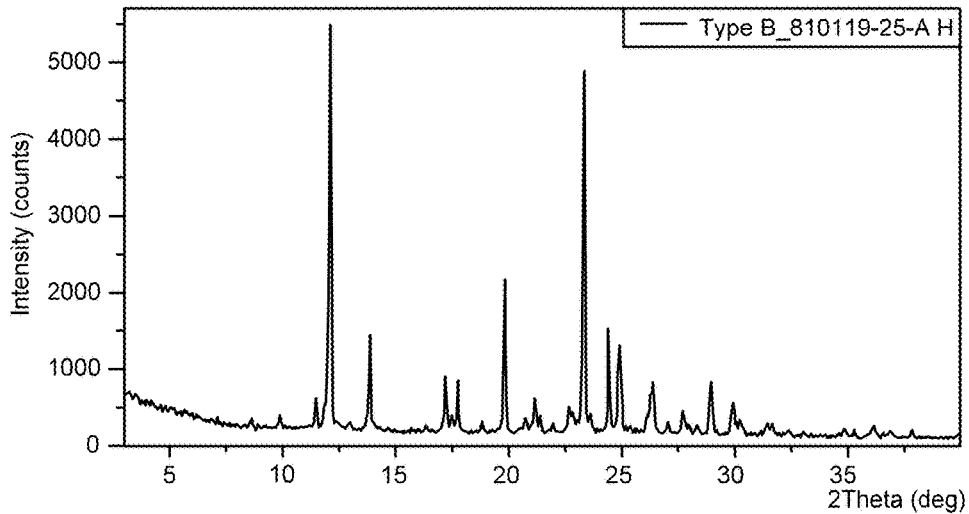
FIG. 40 shows an X-ray powder diffraction (XRPD) pattern of crystalline Type B of Formula IX.
Figure 41:
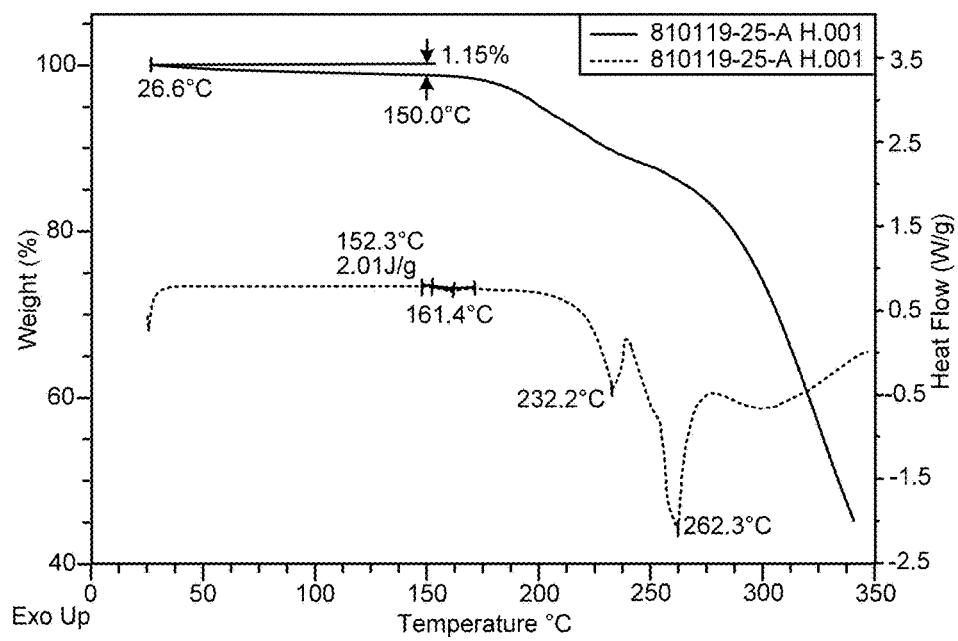
FIG. 41 shows thermo-gravimetric analysis (TGA) and differential scanning calorimetry (DSC) plots of crystalline Type B of Formula IX.
Figure 42:
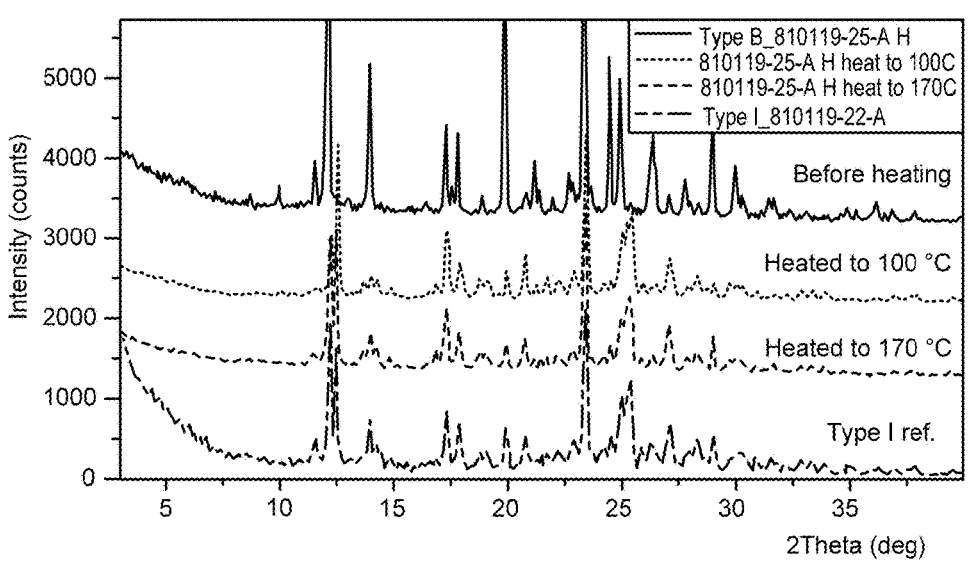
FIG. 42 shows X-ray powder diffraction (XRPD) patterns of crystalline Type B of Formula IX before heating (top), heating to 100° C. (second from top), heating to 170° C. (second from bottom), and crystalline Type I reference (bottom). Upon heating, Type B converts to Type I.

Crystalline Type B of Formula IX was obtained via heating a sample of crystalline Type A to 212° C., cooling to 30° C. under protection of nitrogen and exposing to air conditions. The HPLC purity and stoichiometry (acid:FB) of crystalline Type B were determined to be 97.86 area % and 0.86, respectively. The XRPD pattern is shown in FIG. 40, and TGA/DSC curves are displayed in FIG. 41. The results indicated that Type B was crystalline with a weight loss of 1.2% before 150° C. in TGA and three endothermic peaks at 161.4, 232.2 and 262.3° C. (peak) in DSC. Due to the limited TGA weight loss and neat DSC before 150° C., Type B was speculated to be an anhydrate. To investigate the thermal signal, heating experiment was conducted. As shown in FIG. 42, Type B converted to Type I (Type I is discussed in further detail in Example 38) after being heated to 100° C. or 170° C., cooled to 30° C. under protection of nitrogen, and then exposed to air.

Peak values of the XRPD plot shown in FIG. 40 are provided in Table 22, below.

TABLE 22

XRPD peak values for Crystalline Type B of Formula IX

| Position [°2θ] | Relative Intensity [%] |
|---|---|
| 9.8 | 2.40 |
| 12.0 | 100.00 |
| 13.8 | 25.37 |
| 17.2 | 12.82 |
| 17.7 | 13.85 |
| 18.8 | 2.52 |
| 19.8 | 38.56 |
| 20.7 | 3.48 |
| 21.1 | 6.60 |
| 21.9 | 2.68 |
| 22.6 | 7.05 |
| 23.3 | 92.78 |
| 24.4 | 21.44 |
| 24.8 | 23.23 |
| 26.3 | 13.18 |
| 27.0 | 3.20 |
| 27.7 | 6.15 |
| 28.3 | 2.26 |
| 28.9 | 14.47 |
| 29.9 | 8.96 |
| 30.2 | 2.79 |
| 31.5 | 1.89 |
| 36.1 | 3.11 |
| 37.8 | 1.64 |

Example 33

The Preparation of Crystalline Type C of Formula IX

Figure 43:
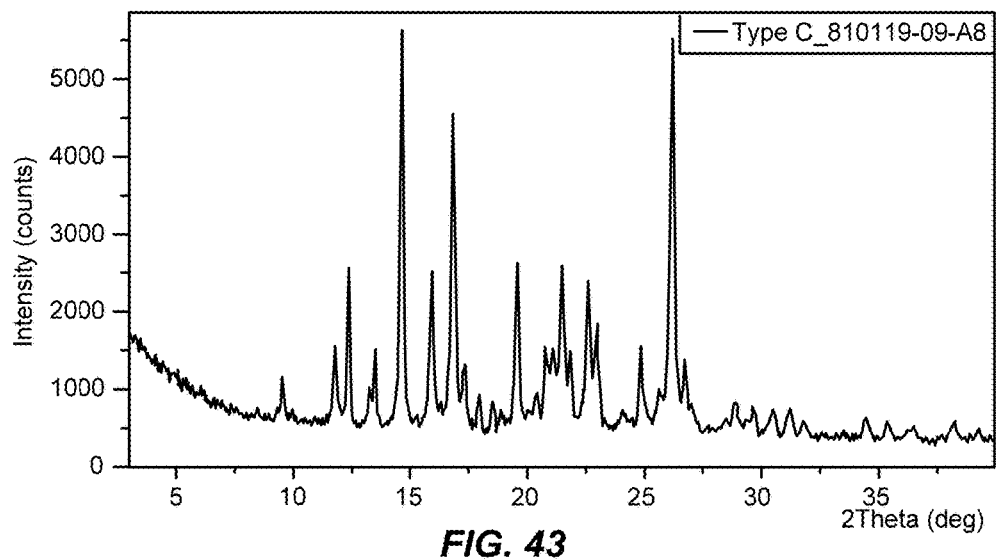
FIG. 43 shows an X-ray powder diffraction (XRPD) pattern of crystalline Type C of Formula IX.
Figure 44:
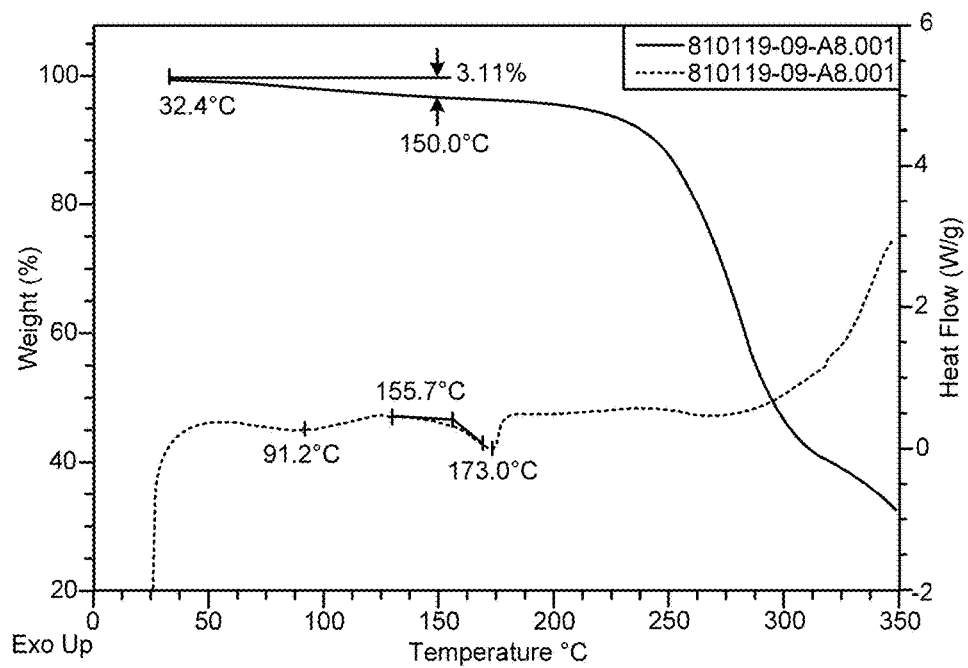
FIG. 44 shows thermo-gravimetric analysis (TGA) and differential scanning calorimetry (DSC) plots of crystalline Type C of Formula IX.

Crystalline Type C of Formula IX was obtained via anti-solvent addition in DMSO/H$_2$O at RT and its XRPD is shown in FIG. 43. TGA and DSC results in FIG. 44 showed a weight loss of 3.1% up to 150° C. and two endothermic peaks at 91.2 and 173.0° C. Since the Cl$^-$ content of Type C sample was 0.17% (the theoretical Cl$^-$ content of mono-HCl salt is 10.8%), Type C was confirmed to be a freebase form.

Peak values of the XRPD plot shown in FIG. 43 are provided in Table 23, below.

TABLE 23

XRPD peak values for Crystalline Type C of Formula IX

| Position [°2θ] | Relative Intensity [%] |
|---|---|
| 9.5 | 10.95 |
| 11.7 | 19.10 |
| 12.3 | 38.53 |
| 13.4 | 19.21 |
| 14.6 | 99.67 |
| 15.8 | 37.90 |
| 16.7 | 79.33 |
| 17.2 | 16.59 |
| 17.8 | 8.43 |
| 18.4 | 6.88 |
| 19.5 | 41.44 |
| 20.3 | 9.55 |
| 20.7 | 21.39 |
| 21.4 | 42.38 |
| 21.7 | 18.03 |
| 22.5 | 37.96 |
| 22.9 | 26.38 |
| 24.0 | 4.72 |
| 24.7 | 20.49 |
| 26.1 | 100.00 |
| 26.7 | 18.16 |
| 28.8 | 8.11 |
| 29.6 | 5.55 |
| 30.4 | 5.96 |
| 31.1 | 5.56 |
| 34.4 | 5.29 |
| 35.3 | 4.44 |
| 36.3 | 2.70 |
| 38.1 | 4.10 |

Example 34

The Preparation of Crystalline Type D & Type F of Formula IX

Figure 45:
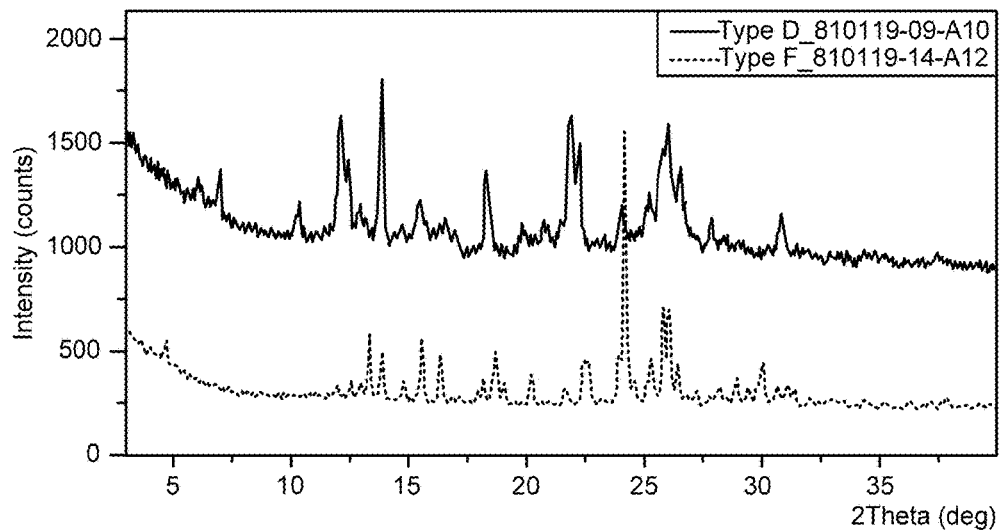
FIG. 45 shows an X-ray powder diffraction (XRPD) pattern of crystalline Type D of Formula IX (upper plot) and crystalline Type F of Formula IX (lower plot).

Crystalline Type D of Formula IX was obtained via anti-solvent addition in MeOH/IPAc system at RT. Type F of Formula IX was obtained via slurry of Type A in toluene at 50° C. Their XRPD patterns are shown in FIG. 45 (Type D, upper plot; Type F, lower plot).

Peak values of the XRPD plot shown in FIG. 45 (Types D and F) are provided in Table 24 and Table 25, below.

TABLE 24

XRPD peak values for Crystalline Type D of Formula IX

| Position [°2θ] | Relative Intensity [%] |
|---|---|
| 6.8 | 19.59 |
| 10.2 | 16.65 |
| 12.0 | 71.32 |
| 12.3 | 43.00 |
| 13.8 | 100.00 |
| 15.4 | 26.66 |
| 16.6 | 12.89 |
| 18.2 | 48.41 |
| 19.8 | 13.71 |
| 21.7 | 78.63 |
| 22.2 | 64.23 |
| 24.0 | 26.05 |
| 26.0 | 72.52 |
| 26.5 | 51.29 |
| 27.8 | 21.59 |
| 30.8 | 23.74 |
| 34.6 | 4.15 |

TABLE 25

XRPD peak values for Crystalline Type F of Formula IX

| Position [°2θ] | Relative Intensity [%] |
|---|---|
| 4.6 | 6.80 |
| 12.4 | 5.23 |
| 12.9 | 5.29 |
| 13.3 | 22.78 |
| 13.8 | 17.01 |
| 14.7 | 5.10 |
| 15.5 | 22.78 |
| 16.3 | 16.83 |
| 18.1 | 8.86 |
| 18.6 | 18.97 |
| 19.0 | 7.62 |
| 20.1 | 10.89 |
| 21.6 | 5.75 |
| 22.3 | 14.39 |
| 22.5 | 16.27 |
| 24.1 | 100.00 |
| 25.2 | 17.28 |
| 25.7 | 35.11 |
| 26.0 | 34.41 |

TABLE 25-continued

XRPD peak values for Crystalline Type F of Formula IX

| Position [°2θ] | Relative Intensity [%] |
|---|---|
| 26.4 | 15.15 |
| 27.2 | 4.40 |
| 28.2 | 6.46 |
| 28.9 | 8.86 |
| 29.4 | 7.40 |
| 30.0 | 15.47 |
| 30.6 | 6.43 |
| 31.0 | 7.51 |
| 31.3 | 5.94 |
| 32.0 | 3.26 |
| 34.4 | 1.81 |
| 35.1 | 1.46 |
| 36.3 | 2.36 |
| 37.0 | 2.00 |
| 37.8 | 3.29 |

Example 35

The Preparation of Crystalline Type E of Formula IX

Figure 46:
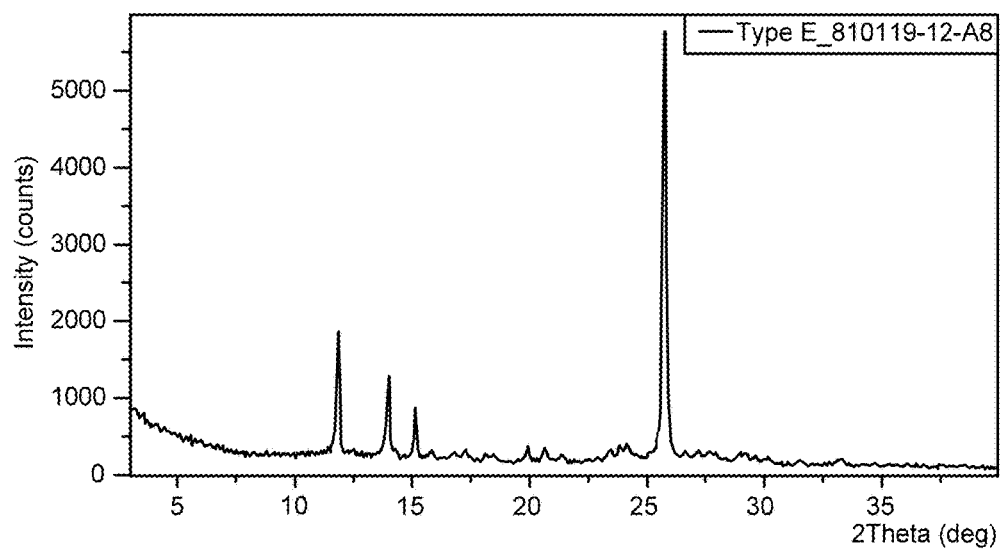
FIG. 46 shows an X-ray powder diffraction (XRPD) pattern of crystalline Type E of Formula IX.
Figure 47:
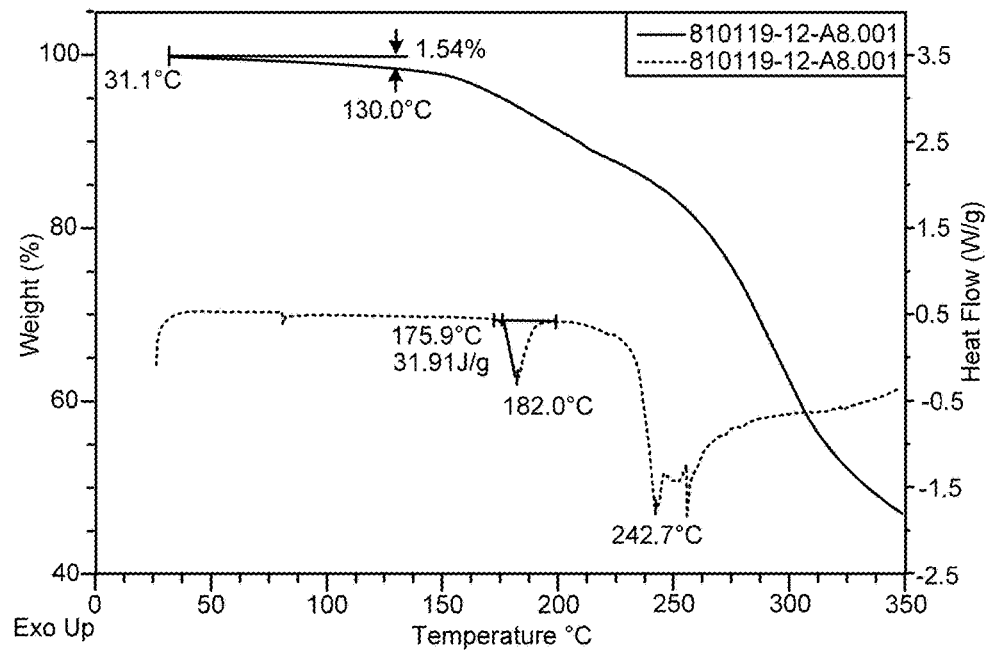
FIG. 47 shows thermo-gravimetric analysis (TGA) and differential scanning calorimetry (DSC) plots of crystalline Type E of Formula IX.
Figure 48:
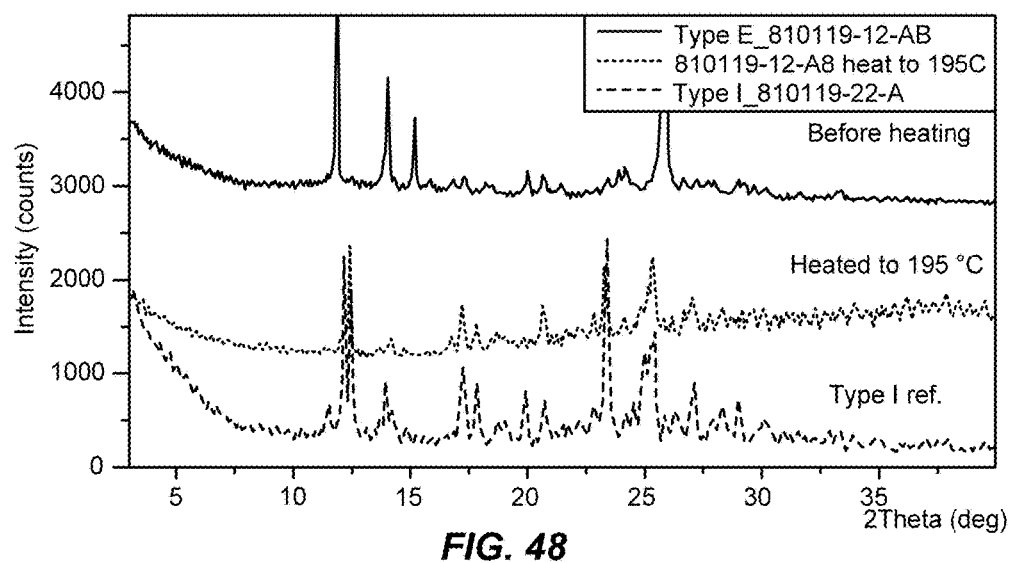
FIG. 48 shows X-ray powder diffraction (XRPD) patterns of crystalline Type E of Formula IX before heating (top), heating to 195° C. (middle), and crystalline Type I reference (bottom). Upon heating, Type E converts to Type I.

Crystalline Type E of Formula IX was obtained via slow evaporation in $CHCl_3$/EtOH at RT. The HPLC purity and stoichiometry (acid:FB) of crystalline Type E of Formula IX were determined to be 98.60 area % and 0.91, respectively. The XRPD pattern is shown in FIG. 46, and TGA/DSC curves are displayed in FIG. 47. The results indicated that crystalline Type E has a weight loss of 1.5% before 130° C. in TGA and two endothermic peaks at 182.0 and 242.7° C. in DSC (peak). Due to the limited TGA weight loss and neat DSC before 170° C., Type E was speculated to be an anhydrate. To investigate the thermal signal at 182.0° C. (peak) in DSC, heating experiment was conducted. As shown in FIG. 48, Type E converted to hydrate Type I after being heated to 195° C., cooled to 30° C. under protection of nitrogen, and then exposed to air. Based on the thermal data and heating experiment, anhydrate Type E might convert to a new anhydrate form (the DSC endothermic signal ~180° C. might be a form transition signal) and then the anhydrate form turned into hydrate Type I via interaction with moisture when exposed to ambient condition.

Peak values of the XRPD plot shown in FIG. 46 are provided in Table 26, below.

TABLE 26

XRPD peak values for Crystalline Type E of Formula IX

| Position [°2θ] | Relative Intensity [%] |
|---|---|
| 11.8 | 29.29 |
| 14.0 | 18.45 |
| 15.1 | 12.00 |
| 17.2 | 2.51 |
| 18.2 | 0.97 |
| 19.9 | 3.73 |
| 20.6 | 2.90 |
| 21.4 | 1.43 |
| 24.0 | 3.14 |
| 25.8 | 100.00 |
| 27.8 | 2.34 |
| 29.1 | 2.06 |
| 33.2 | 1.16 |

Example 36

The Preparation of Crystalline Type G of Formula IX

Figure 49:
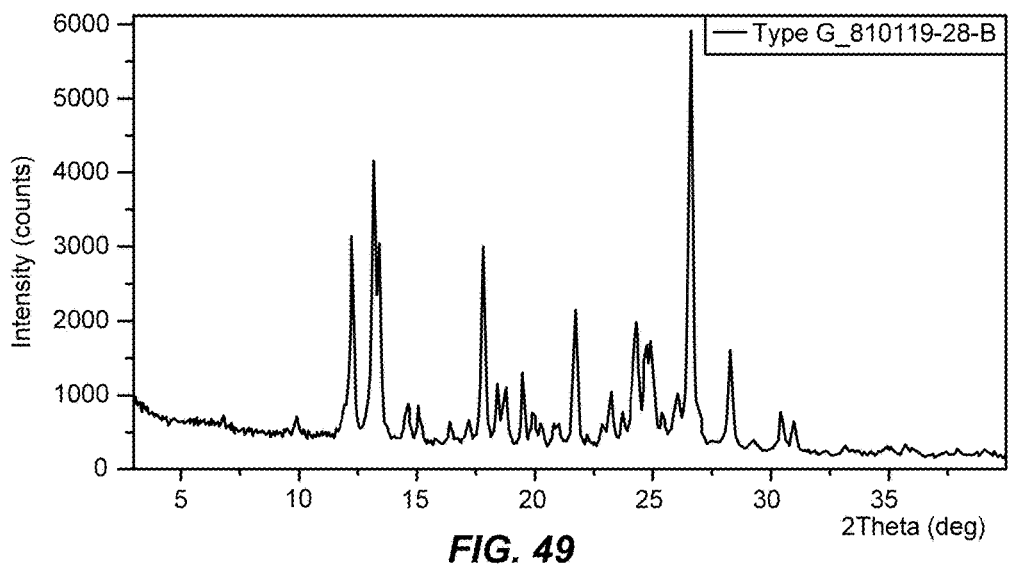
FIG. 49 shows an X-ray powder diffraction (XRPD) pattern of crystalline Type G of Formula IX.
Figure 50:
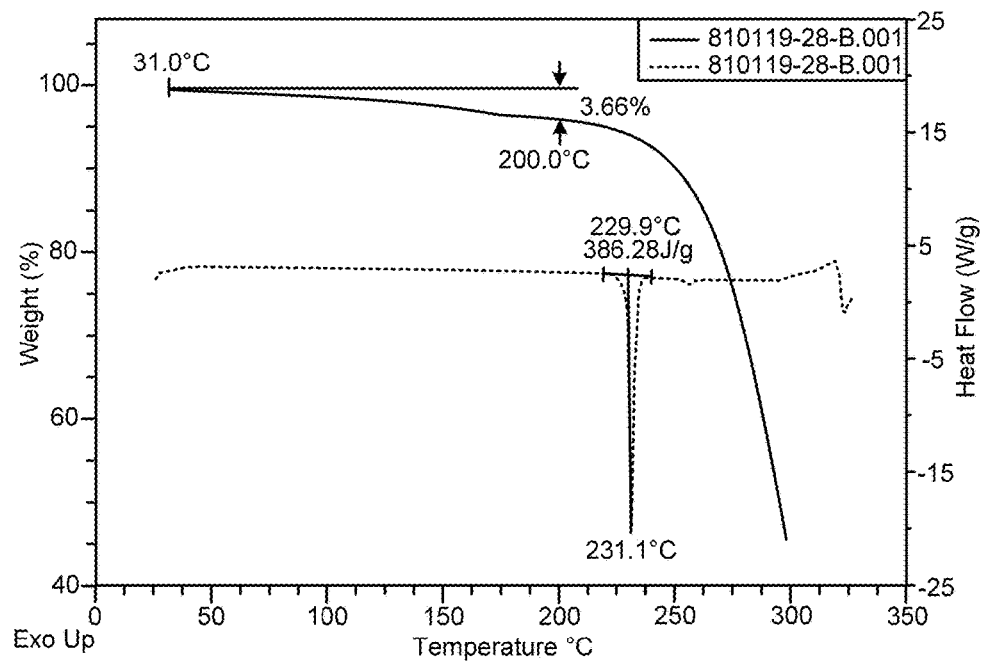
FIG. 50 shows thermo-gravimetric analysis (TGA) and differential scanning calorimetry (DSC) plots of crystalline Type G of Formula IX.

Crystalline Type G of Formula IX was obtained via slurry in $DMAc/H_2O$ (v:v, 1:3) at RT and its XRPD is shown in FIG. 49. TGA and DSC results in FIG. 50 showed a weight loss of 3.7% up to 200° C. and one sharp endothermic signal at 231.1° C. (peak). Since the $Cl^-$ content of Type G sample was 0.14% (the theoretical $Cl^-$ content of mono-HCl salt is 10.8%), Type G was confirmed to be a freebase form.

Peak values of the XRPD plot shown in FIG. 49 are provided in Table 27, below.

TABLE 27

XRPD peak values for Crystalline Type G of Formula IX

| Position [°2θ] | Relative Intensity [%] |
|---|---|
| 6.6 | 1.33 |
| 9.8 | 3.80 |
| 12.2 | 47.25 |
| 13.1 | 66.55 |
| 13.4 | 46.87 |
| 14.6 | 8.71 |
| 15.1 | 8.08 |
| 16.4 | 3.87 |
| 17.1 | 5.54 |
| 17.8 | 46.61 |
| 18.4 | 14.28 |
| 18.7 | 13.76 |
| 19.4 | 16.96 |
| 19.9 | 8.02 |
| 20.3 | 4.92 |
| 21.0 | 5.62 |
| 21.7 | 32.86 |
| 22.8 | 5.34 |
| 23.2 | 13.61 |
| 23.7 | 8.42 |
| 24.3 | 29.93 |
| 24.7 | 23.96 |
| 24.9 | 25.98 |
| 25.4 | 8.92 |
| 26.0 | 13.52 |
| 26.6 | 100.00 |
| 28.3 | 24.14 |
| 29.2 | 2.64 |
| 30.5 | 8.98 |
| 30.9 | 7.92 |
| 33.1 | 1.62 |
| 35.0 | 1.54 |
| 35.7 | 2.29 |

Example 37

The Preparation of Crystalline Type H of Formula IX

Figure 51:
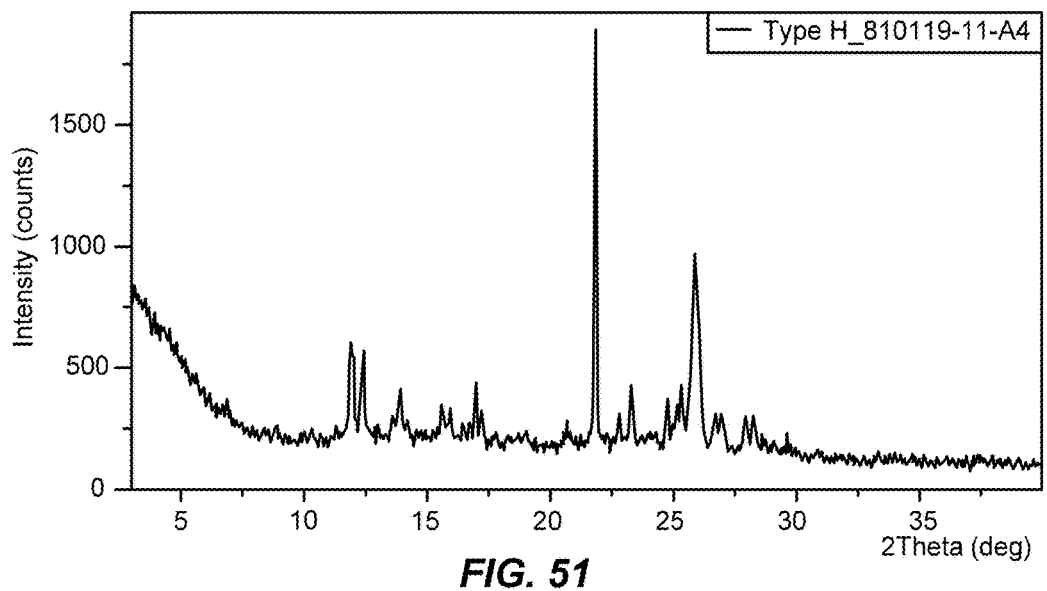
FIG. 51 shows an X-ray powder diffraction (XRPD) pattern of crystalline Type H of Formula IX.
Figure 52:
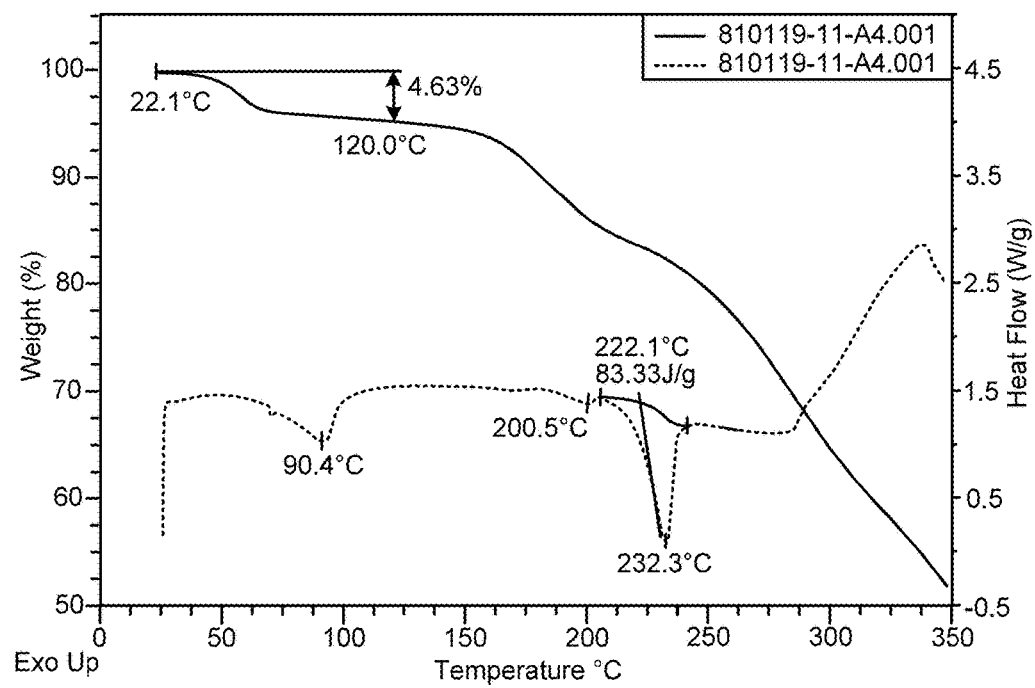
FIG. 52 shows thermo-gravimetric analysis (TGA) and differential scanning calorimetry (DSC) plots of crystalline Type H of Formula IX.
Figure 53:
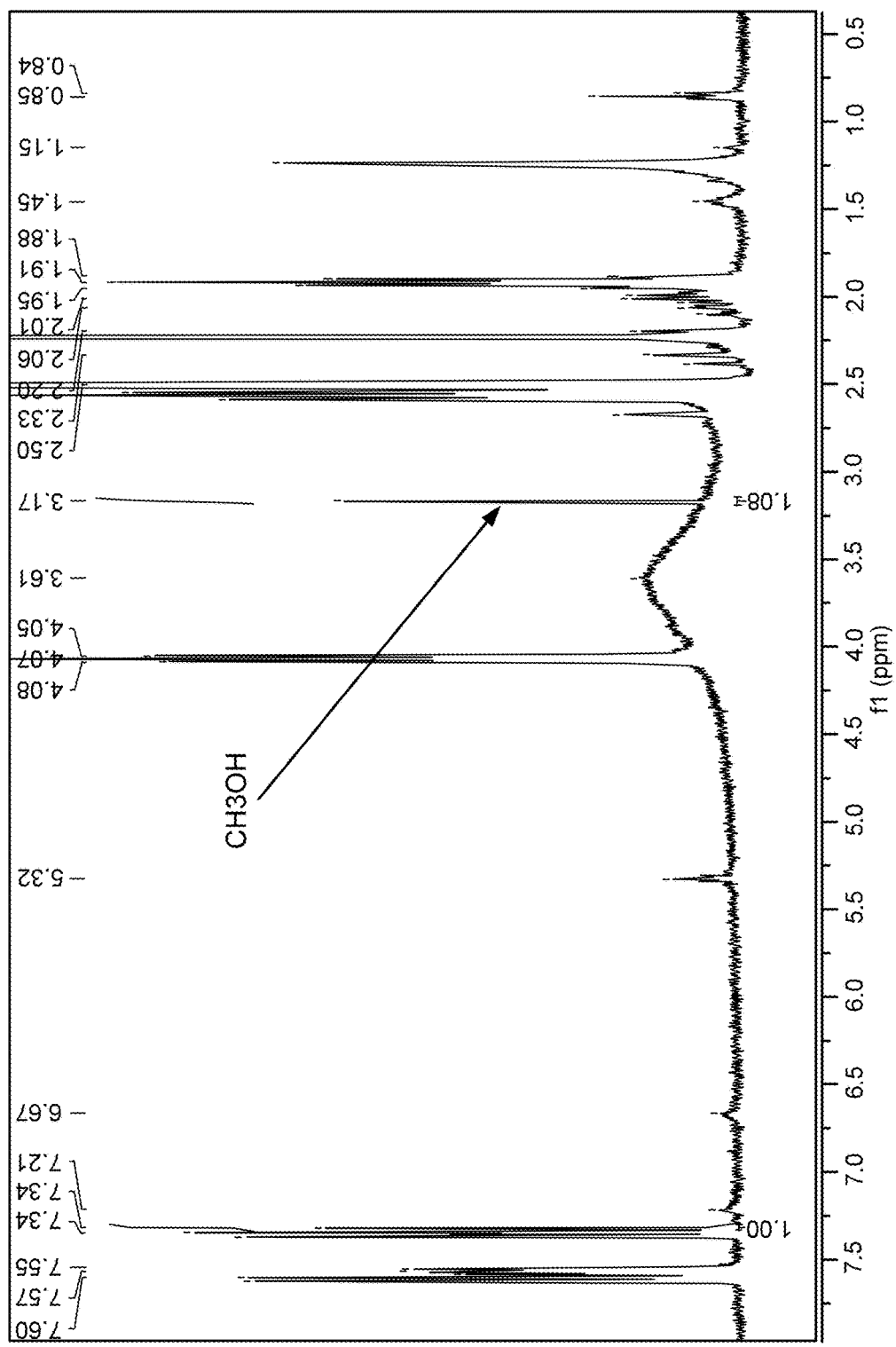
FIG. 53 shows $^1$H NMR spectrum of crystalline Type H of Formula IX.
Figure 54:
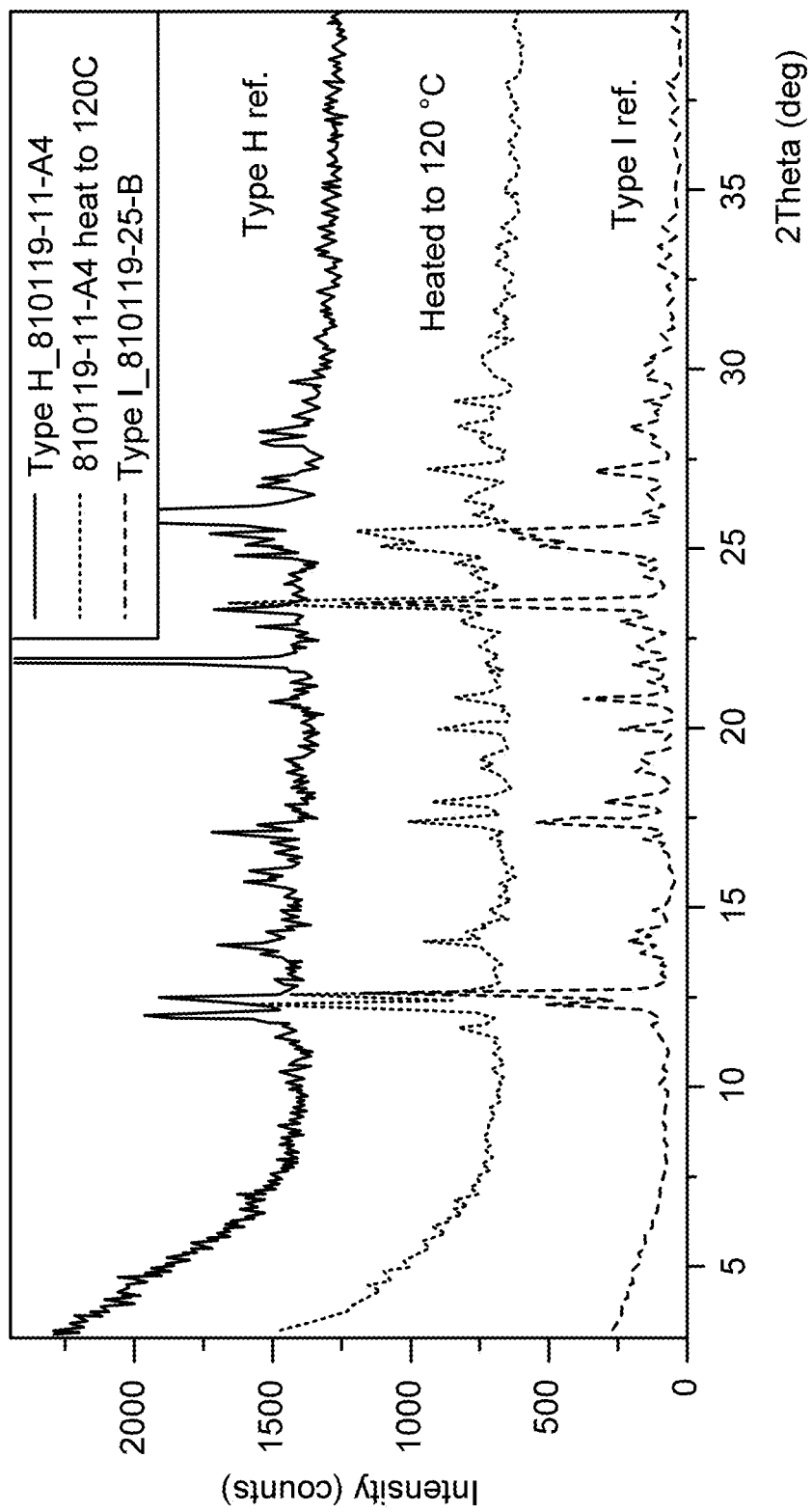
FIG. 54 shows X-ray powder diffraction (XRPD) patterns of crystalline Type H of Formula IX before heating (top), heating to 120° C. (middle), and crystalline Type I reference (bottom). Upon heating, Type H converts to Type I.

Crystalline Type H of Formula IX was obtained via slow evaporation in acetone/MeOH system at RT, and its XRPD is shown in FIG. 51. The HPLC purity and stoichiometry (acid:FB) of Type H (810119-11-A4) were determined to be 98.47 area % and 0.91, respectively. TGA and DSC curves (FIG. 52) showed a weight loss of 4.6% before 120° C. and three endothermic peaks at 90.4, 200.5 and 232.3° C. (peak). As shown in the $^1H$ NMR spectrum (FIG. 53), 0.36 equivalent of MeOH (~3.40 wt %) was detected. Combined with the fact that form change to Type I was observed after Type H was heated to 120° C., cooled to 30° C. under protection of nitrogen (FIG. 54), and exposed to ambient conditions, Form H was speculated to be a MeOH solvate.

Peak values of the XRPD plot shown in FIG. 51 are provided in Table 28, below.

TABLE 28

XRPD peak values for Crystalline Type H of Formula IX

| Position [°2θ] | Relative Intensity [%] |
|---|---|
| 11.8 | 28.73 |
| 12.3 | 21.19 |
| 13.8 | 14.54 |
| 15.7 | 5.38 |
| 16.9 | 16.03 |
| 20.6 | 4.73 |
| 21.7 | 100.00 |
| 23.2 | 17.57 |
| 24.7 | 12.94 |
| 25.7 | 58.09 |
| 26.7 | 6.83 |
| 27.8 | 9.32 |
| 28.1 | 9.00 |

Example 38

The Preparation of Crystalline Type I of Formula IX

Figure 55:
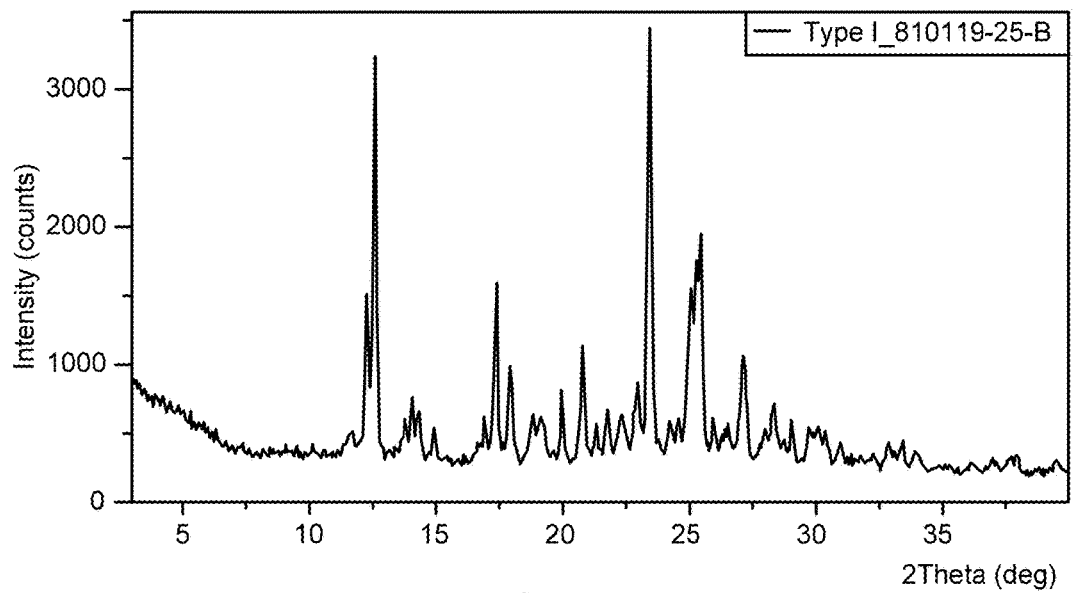
FIG. 55 shows an X-ray powder diffraction (XRPD) pattern of crystalline Type I of Formula IX.
Figure 56:
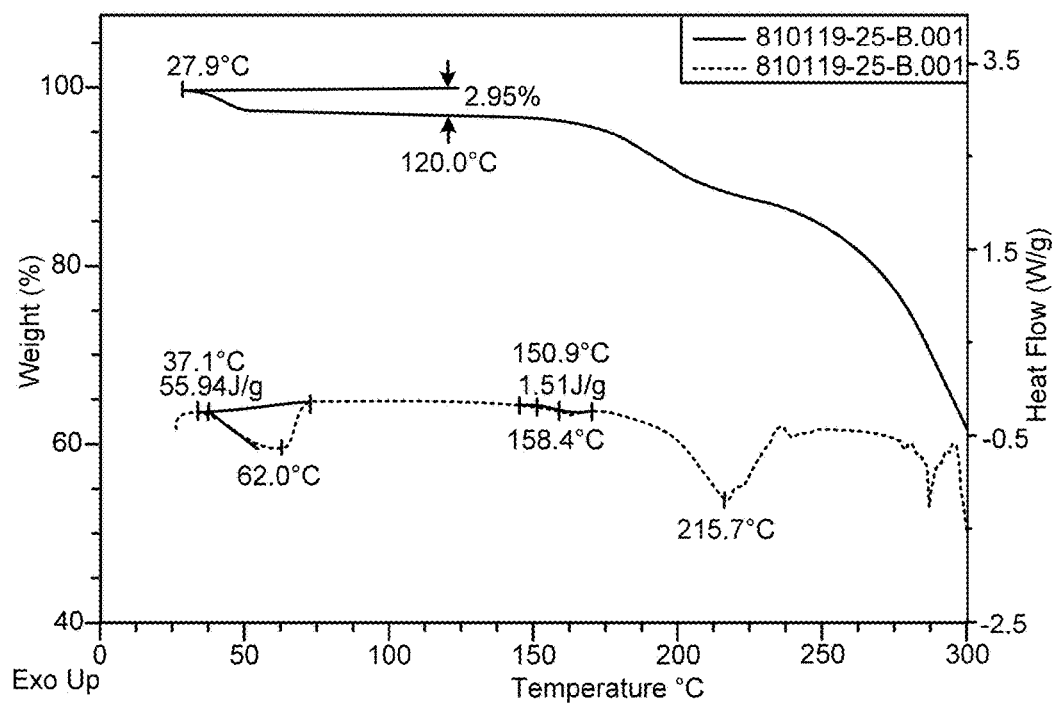
FIG. 56 shows thermo-gravimetric analysis (TGA) and differential scanning calorimetry (DSC) plots of crystalline Type I of Formula IX.

Crystalline Type I of Formula IX was obtained via heating crystalline Type B of Formula IX to 100° C., cooled to 30° C. under protection of nitrogen, and then exposed to air. Its XRPD is shown in FIG. 55. The HPLC purity and stoichiometry (acid:FB) of crystalline Type I of Formula IX were determined to be 97.94 area % and 0.86, respectively. Since crystalline Type I was obtained via solid-state transition of anhydrate Type B and 3.0% weight loss (equivalent to 0.5 molar water) with endothermic peak at 62.0° C. (peak, FIG. 56) was observed, Type I was speculated to be a hydrate.

Peak values of the XRPD plot shown in FIG. 55 are provided in Table 29, below.

TABLE 29

XRPD peak values for Crystalline Type I of Formula IX

| Position [°2θ] | Relative Intensity [%] |
|---|---|
| 11.4 | 4.60 |
| 12.1 | 35.57 |
| 12.4 | 89.18 |
| 13.6 | 8.36 |
| 13.9 | 14.40 |
| 14.2 | 10.59 |
| 14.8 | 6.38 |
| 16.8 | 9.64 |
| 17.2 | 41.23 |
| 17.8 | 21.69 |
| 18.7 | 10.82 |
| 19.1 | 9.61 |
| 19.9 | 15.55 |
| 20.7 | 27.63 |
| 21.2 | 8.33 |
| 21.7 | 12.83 |
| 22.2 | 10.01 |
| 22.8 | 18.37 |
| 23.3 | 100.00 |
| 24.1 | 9.53 |
| 24.9 | 41.18 |
| 25.4 | 52.09 |
| 25.9 | 10.04 |
| 27.0 | 26.02 |
| 28.3 | 14.09 |
| 29.0 | 11.22 |
| 29.6 | 8.99 |

TABLE 29-continued

XRPD peak values for Crystalline Type I of Formula IX

| Position [°2θ] | Relative Intensity [%] |
|---|---|
| 30.0 | 8.40 |
| 30.8 | 5.50 |
| 32.8 | 6.13 |
| 33.3 | 6.37 |
| 33.8 | 4.22 |
| 36.1 | 1.88 |
| 36.9 | 2.91 |
| 37.8 | 2.89 |

Figure 57:
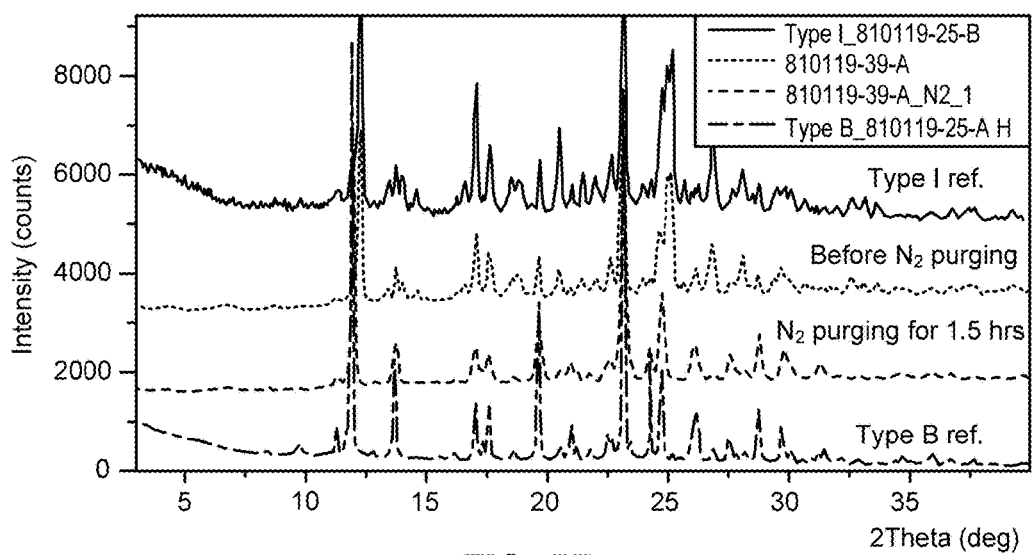
FIG. 57 shows X-ray powder diffraction (XRPD) patterns of crystalline Type I of Formula IX (reference, top), before $N_2$ purging (second from top), after $N_2$ purging for 1.5 hrs (second from bottom), and crystalline Type B reference (bottom). Upon $N_2$ purging, Type I converts to Type B.
Figure 58:
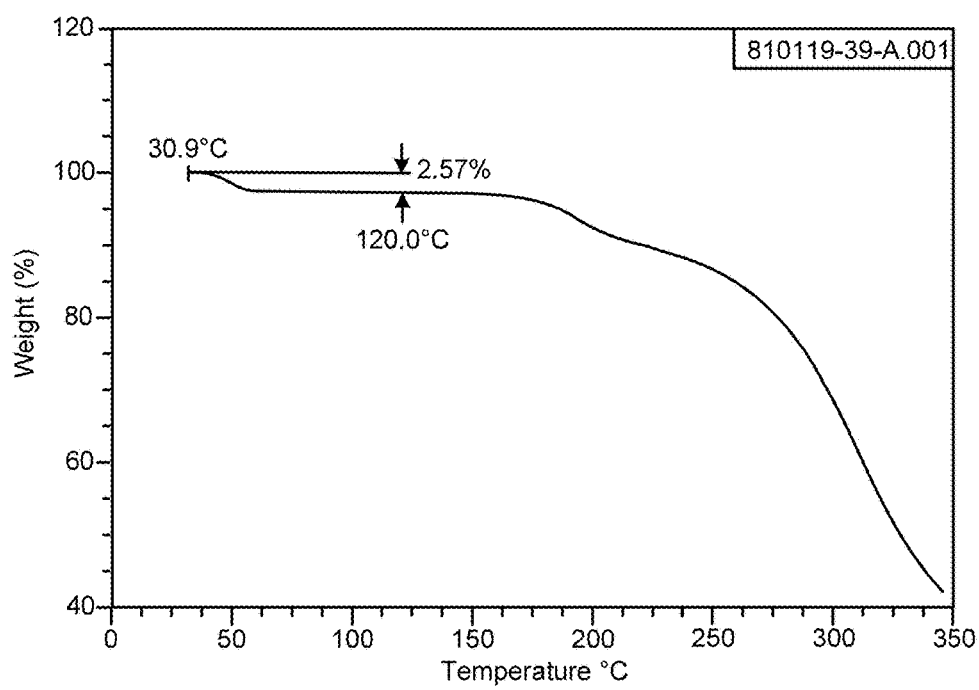
FIG. 58 shows thermo-gravimetric analysis (TGA) plot of crystalline Type I of Formula IX.

To further identify crystalline Type I and investigate its dehydration behavior, in-situ XRPD with $N_2$ flow was performed to observe the dehydrated form of Type I, and KF test was conducted to confirm whether the TGA weight loss was caused by water content or not. As shown in FIG. 57, form change to anhydrate crystalline Type B was observed for crystalline Type I with $N_2$ purging for about 1.5 hr. (30° C./16% RH). As shown in FIG. 58 a weight loss of 2.6% up to 120° C. was observed in crystalline Type I. Based on the KF result, around 3.48% water content was observed in the crystalline Type I sample. Combined with the form change to anhydrate Type B under $N_2$ flow, Type I was identified to be a hydrate.

Example 39

The Preparation of Crystalline Type J of Formula IX

Figure 59:
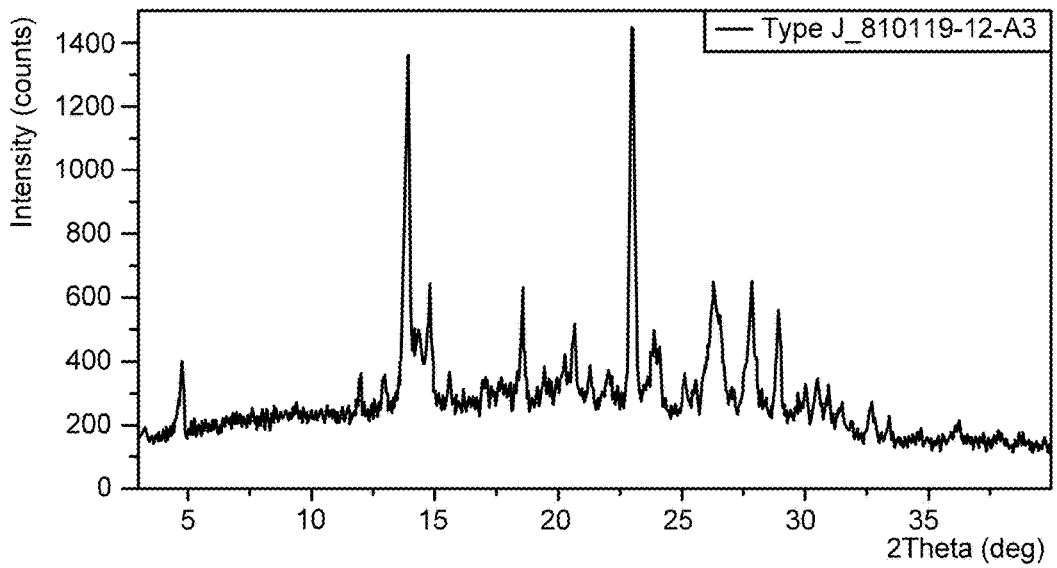
FIG. 59 shows an X-ray powder diffraction (XRPD) pattern of crystalline Type J of Formula IX.
Figure 60:
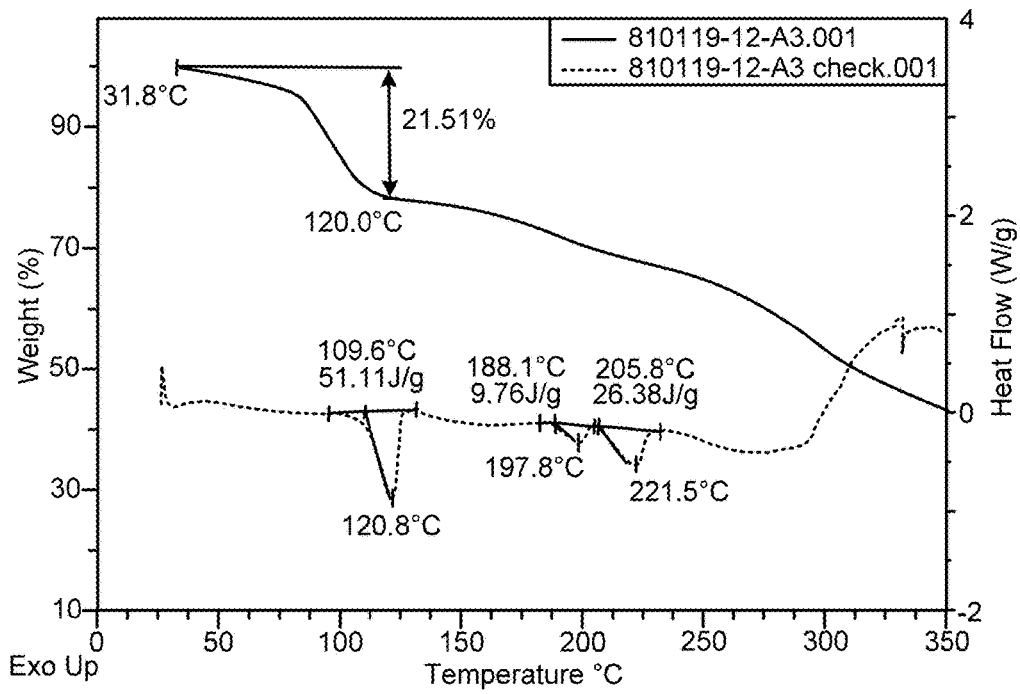
FIG. 60 shows thermo-gravimetric analysis (TGA) and differential scanning calorimetry (DSC) plots of crystalline Type J of Formula IX.
Figure 61:
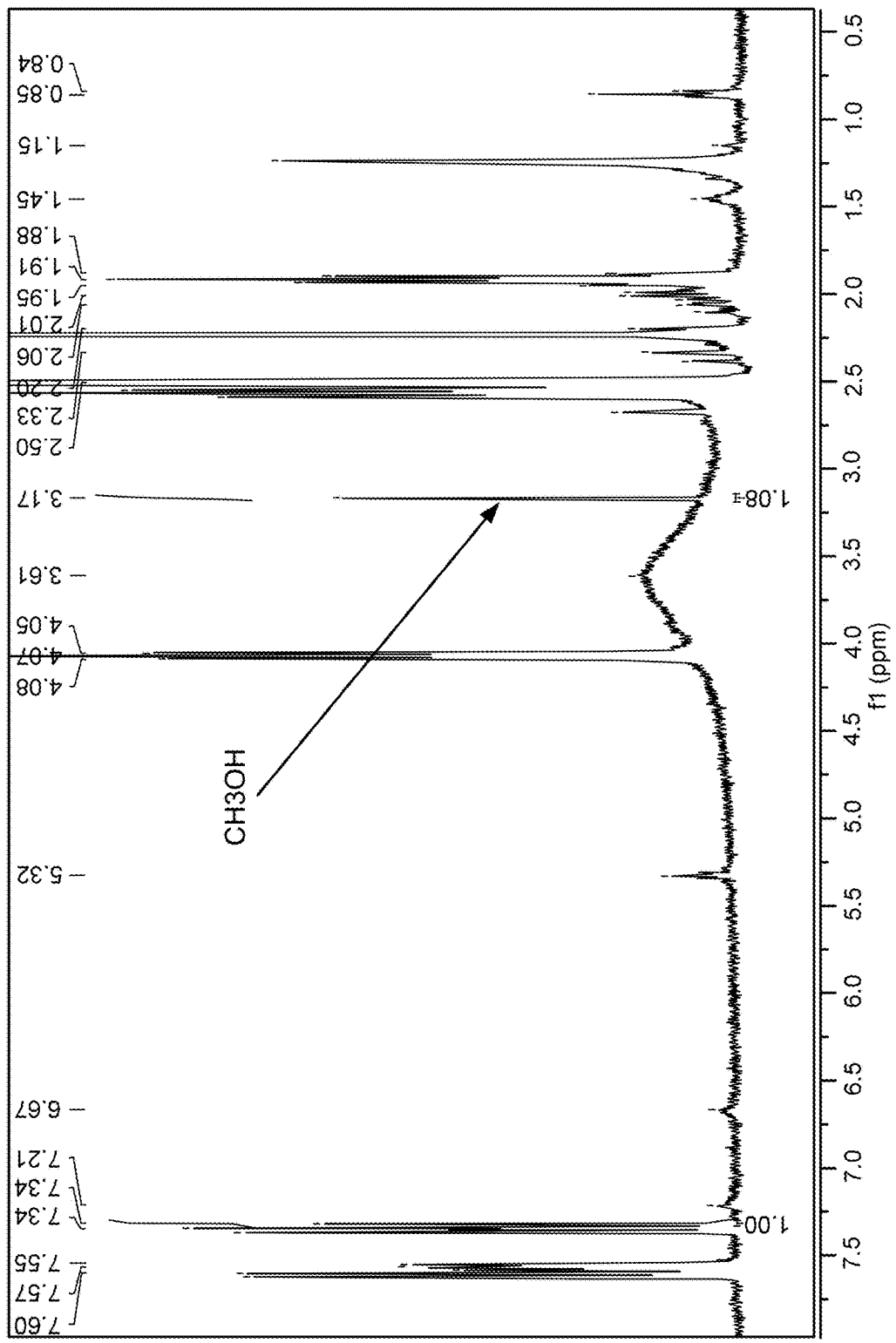
FIG. 61 shows $^1$H NMR spectrum of crystalline Type J of Formula IX.
Figure 62:
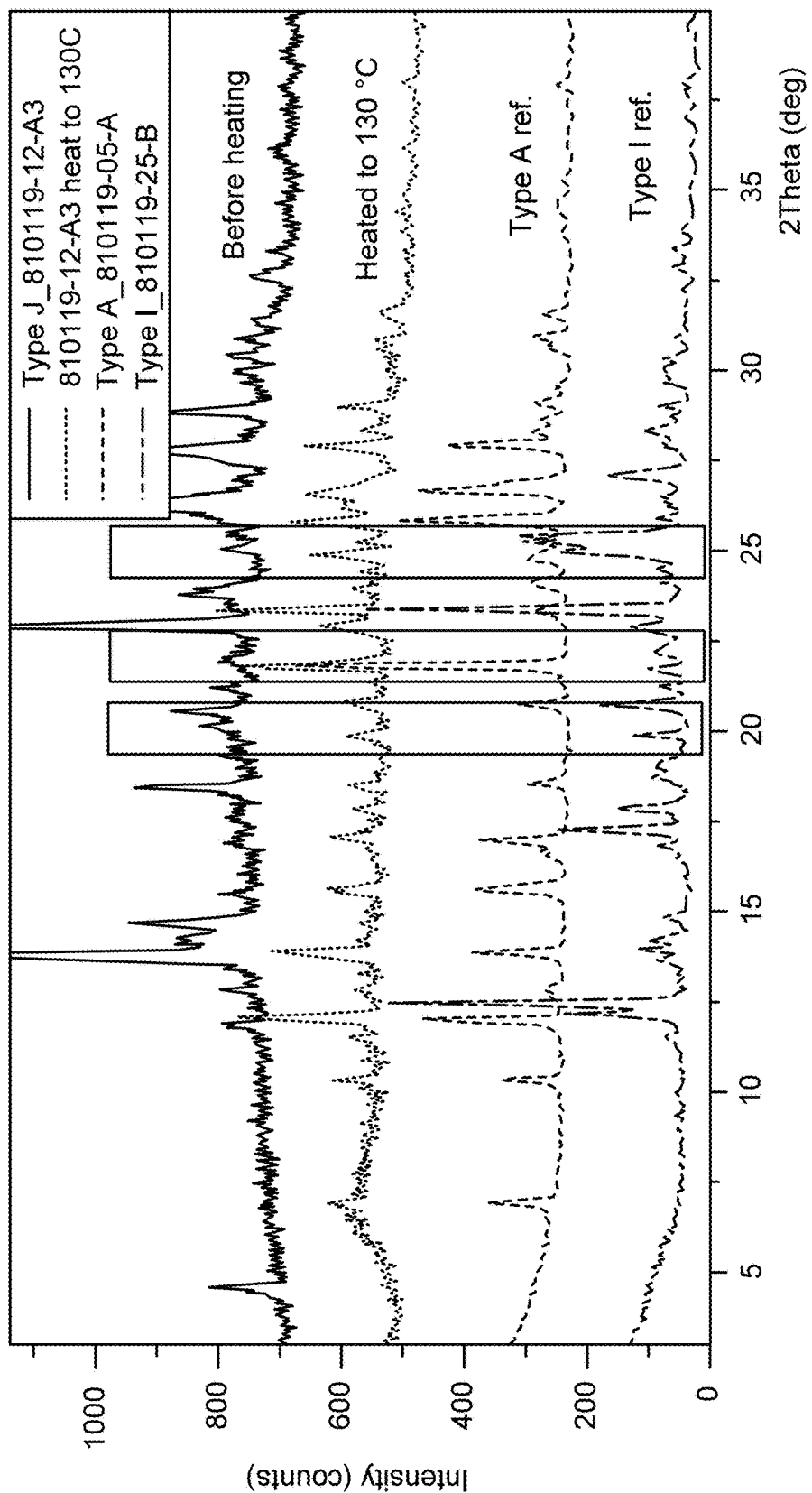
FIG. 62 shows X-ray powder diffraction (XRPD) patterns of crystalline Type J of Formula IX before heating (top), heating to 130° C. (second from top), crystalline Type A reference (second from bottom), and crystalline Type I reference (bottom). Upon heating, Type J converts to a mixture of Type A and Type I.

Crystalline Type J of Formula IX was obtained by slow evaporation followed by vacuum drying at 50° C. in MEK/DMAc system, and its XRPD is shown in FIG. 59. The HPLC purity and stoichiometry (acid:FB) of crystalline Type J of Formula IX was determined to be 91.69 area % and 0.90, respectively. TGA and DSC results in FIG. 60 showed a weight loss of 21.5% up to 120° C. and three endothermic peaks at 120.8, 197.8 and 221.5° C. (peak). As shown in the $^1$H NMR spectrum (FIG. 61), 4.9 equivalent of DMAc (~56.51 wt %) was detected. Combined with the fact that form change to a mixture of crystalline Type I (highlighted) and crystalline Type A was observed after crystalline Type J was heated to 130° C., cooled to 30° C. under protection of nitrogen, and exposed to ambient conditions (FIG. 62), Type J was speculated to be a DMAc solvate.

Peak values of the XRPD plot shown in FIG. 59 are provided in Table 30, below.

TABLE 30

XRPD peak values for Crystalline Type J of Formula IX

| Position [°2θ] | Relative Intensity [%] |
|---|---|
| 4.6 | 18.19 |
| 11.8 | 8.94 |
| 12.8 | 9.10 |
| 13.8 | 87.83 |
| 14.6 | 29.55 |
| 18.4 | 26.65 |
| 20.5 | 18.63 |
| 21.1 | 8.10 |
| 21.9 | 8.04 |
| 22.8 | 100.00 |
| 23.7 | 18.41 |
| 26.2 | 33.09 |
| 27.7 | 35.16 |
| 28.8 | 29.02 |

TABLE 30-continued

XRPD peak values for Crystalline Type J of Formula IX

| Position [°2θ] | Relative Intensity [%] |
|---|---|
| 30.4 | 12.86 |
| 30.8 | 8.86 |
| 31.3 | 6.46 |
| 32.6 | 8.32 |
| 36.0 | 3.83 |

Example 40

The Preparation of Crystalline Type K of Formula IX

Figure 63:
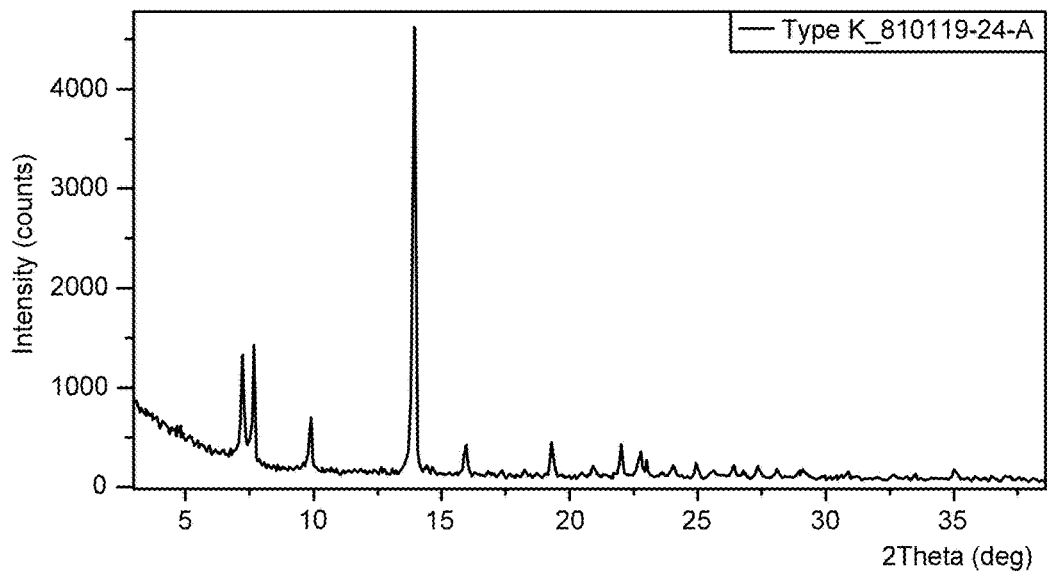
FIG. 63 shows an X-ray powder diffraction (XRPD) pattern of crystalline Type K of Formula IX.
Figure 64:
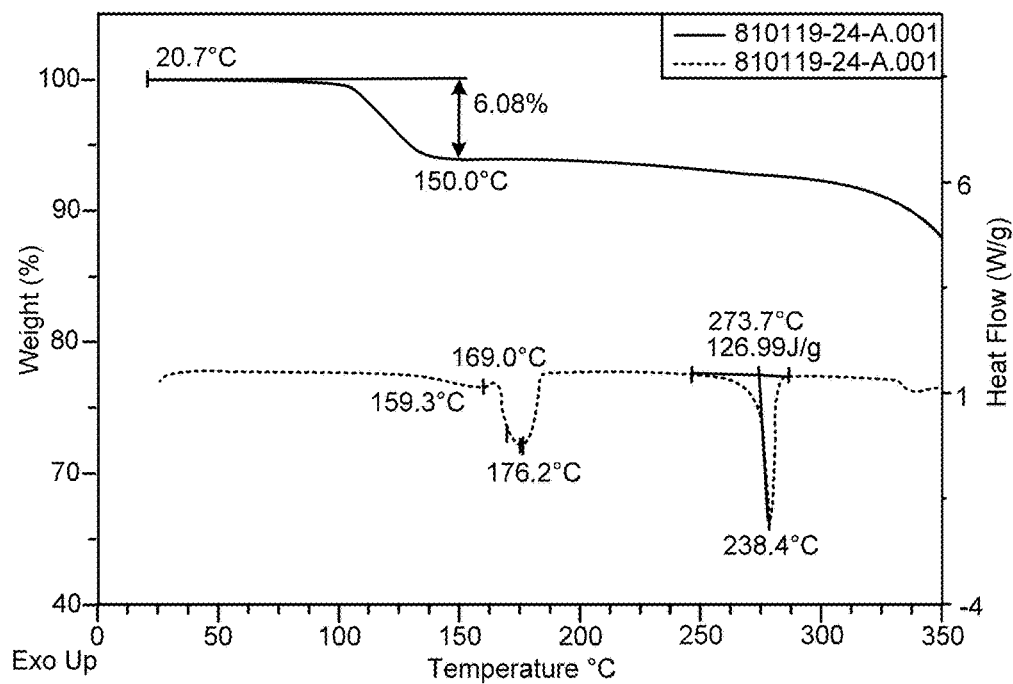
FIG. 64 shows thermo-gravimetric analysis (TGA) and differential scanning calorimetry (DSC) plots of crystalline Type K of Formula IX.

Free base material as prepared in Example 11 was characterized by XRPD (FIG. 63), TGA (FIG. 64), and DSC (FIG. 64). This material was referred to as crystalline Type K of Formula IX. A weight loss of 6.1% up to 150° C. was observed in TGA, and DSC result showed endothermic peaks at 159.3, 176.2 and 278.4° C. (peak). The HPLC purity of crystalline Type K of Formula IX was determined to be 99.12 area %.

Peak values of the XRPD plot shown in FIG. 63 are provided in Table 31, below.

TABLE 31

XRPD peak values for Crystalline Type K of Formula IX

| Position [°2θ] | Relative Intensity [%] |
|---|---|
| 7.1 | 21.72 |
| 7.5 | 20.44 |
| 9.8 | 11.27 |
| 13.9 | 100.00 |
| 15.9 | 6.59 |
| 19.3 | 7.18 |
| 20.9 | 2.30 |
| 21.9 | 7.51 |
| 22.7 | 5.79 |
| 23.0 | 3.40 |
| 24.0 | 2.73 |
| 24.9 | 3.09 |
| 25.5 | 1.35 |
| 27.3 | 2.70 |
| 28.1 | 1.86 |
| 29.1 | 1.70 |
| 35.0 | 1.79 |

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. Crystalline Form Type A of Formula IX as its HCl salt

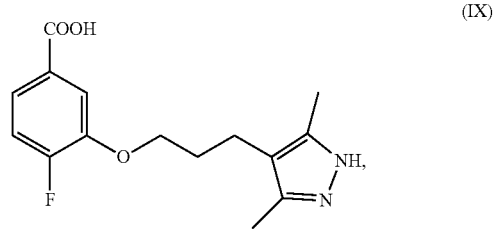 [SMILES: Cc1n[nH]c(C)c1CCCOc1cc(C(=O)O)ccc1F]

(IX)

characterized by an X-ray powder diffraction pattern comprising peaks at 12.0, 21.8, 25.9, 26.7, and 27.9 degrees 2θ (±0.2 degrees 2θ).

2. Crystalline Form Type A of Formula IX as its HCl salt according to claim 1, characterized by an X-ray powder diffraction pattern substantially in accordance with FIG. 31.

3. Crystalline Form Type A of Formula IX as its HCl salt according to claim 1, which is substantially free of other Formula IX crystalline or amorphous forms.

4. Crystalline Form Type A of Formula IX as its HCl salt according to claim 1, further characterized by a weight loss ranging from about 0.7% to about 1.9% upon heating to around 150° C., as measured by thermal gravimetric analysis.

5. Crystalline Form Type A of Formula IX as its HCl salt according to claim 4, wherein the weight loss is about 1.3%.

6. Crystalline Form Type A of Formula IX as its HCl salt according to claim 1, characterized by water uptake of about 1.6% at 25° C./80% relative humidity (RH) after undergoing a dynamic vapor sorption cycle which includes pre-equilibration at 0% RH.

7. Crystalline Form Type A of Formula IX as its HCl salt according to claim 1, characterized by gains of less than 2.5% weight after undergoing a dynamic vapor sorption cycle from about 0% relative humidity (RH) to about 90% RH.

8. Crystalline Form Type A of Formula IX as its HCl salt according to claim 1, having a dynamic vapor sorption profile substantially as shown in FIG. 37.

9. Crystalline Form Type A of Formula IX as its HCl salt according to claim 1, further characterized by a differential scanning calorimetry thermogram comprising endothermic peaks at around 211-214 and 237-239° C.

10. Crystalline Form Type A of Formula IX as its HCl salt according to claim 9, wherein, said differential scanning calorimetry thermogram comprises endothermic peaks around 11.7, 212.6, and 237.3° C.

* * * * *